US012763163B2

(12) United States Patent
Gross et al.

(10) Patent No.: US 12,763,163 B2
(45) Date of Patent: Oct. 13, 2026

(54) CANCER CLASSIFICATION WITH GENOMIC REGION MODELING

(71) Applicant: Grail, Inc., Menlo Park, CA (US)

(72) Inventors: Samuel S. Gross, Sunnyvale, CA (US); Joshua Newman, Mountain View, CA (US); Virgil Nicula, Cupertino, CA (US)

(73) Assignee: Grail, Inc., Menlo Park, CA (US)

( * ) Notice: Subject to any disclaimer, the term of this patent is extended or adjusted under 35 U.S.C. 154(b) by 962 days.

(21) Appl. No.: 17/216,551

(22) Filed: Mar. 29, 2021

(65) Prior Publication Data

US 2021/0313006 A1 Oct. 7, 2021

Related U.S. Application Data

(60) Provisional application No. 63/144,380, filed on Feb. 1, 2021, provisional application No. 63/003,087, filed on Mar. 31, 2020.

(51) Int. Cl.

*G16B 5/20* (2019.01)
*G16B 40/00* (2019.01)
*G16H 70/60* (2018.01)

(52) U.S. Cl.

CPC ............... *G16B 5/20* (2019.02); *G16B 40/00* (2019.02); *G16H 70/60* (2018.01)

(58) Field of Classification Search

CPC ........ G16B 40/20; G16B 20/00; G16B 40/00; G16B 30/00; G16B 20/10; G16B 40/10; G16B 15/00; G16B 20/30; G16B 50/10; G16B 50/30; G16B 45/00; G16B 50/00; C12Q 1/6886; C12Q 2600/154; C12Q 2537/164; C12Q 2600/112; C12Q 2600/118; G16H 50/20; G16H 50/70; G16H 50/30; G16H 10/60; G16H 70/60; G16H 50/50; G16H 70/20; G06N 20/00; G06N 20/20; G06N 3/08; G06N 3/045; G06N 3/04; G01N 2800/7028; G01N 2800/50; G01N 2800/56; G01N 33/574; G06F 18/24; G06F 16/285; G06F 17/18; G06F 18/213; G06F 18/2415

See application file for complete search history.

(56) References Cited

U.S. PATENT DOCUMENTS

| | | | | |
|---|---|---|---|---|
| 11,482,303 | B2 * | 10/2022 | Nicula | G06N 3/045 |
| 2018/0237863 | A1 | 8/2018 | Namsaraev et al. | |
| 2019/0136209 | A1 * | 5/2019 | Yukari | C12N 7/00 |
| 2019/0287649 | A1 * | 9/2019 | Filippova | G16B 30/10 |
| 2019/0287652 | A1 * | 9/2019 | Gross | G16H 50/20 |
| 2019/0316209 | A1 | 10/2019 | Hubbell et al. | |
| 2020/0385813 | A1 | 12/2020 | Venn | |
| 2021/0313006 | A1 * | 10/2021 | Gross | C12Q 1/6886 |
| 2021/0358676 | A1 * | 11/2021 | Wang | H01F 27/341 |
| 2023/0170048 | A1 * | 6/2023 | Maher | G16H 70/60 514/789 |
| 2024/0062849 | A1 * | 2/2024 | Nicula | G16H 50/20 |

FOREIGN PATENT DOCUMENTS

| | | | | |
|---|---|---|---|---|
| WO | WO 2018/081130 A1 | | 5/2018 | |
| WO | WO-2019084559 A1 | * | 5/2019 | C12Q 1/6886 |
| WO | WO 2019/209954 A1 | | 10/2019 | |
| WO | WO 2020/132544 A1 | | 6/2020 | |
| WO | WO 2021/119471 A1 | | 6/2021 | |

OTHER PUBLICATIONS

Tian, Q. et al. A Hybrid Ensemble Approach for Identifying Robust Differentially Methylated Loci in Pan-Cancers. Frontiers in Genetics, vol. 10, article 774, 12 pages, published Sep. 5, 2019. (Year: 2019).*

Mamanova (2010) Target enrichment strategies for next generation sequencing. Nature Methods, vol. 7 No. 2, p. 111-119 and some supplemental material. (Year: 2010).*

Chen (Apr. 2019) Design of a targeted sequencing assay to detect rare mutations in circulating tumor DNA. Genetic Testing and Molecular Biomarkers, vol. 23, No. 4, p. 264-269. (Year: 2019).*

Khwaja, M. et al. (Oct. 5, 2018) A deep autoencoder system for differentiation of cancer types based on DNA methylation state. arXiv : 1810.01243v2, 8 pages. (Year: 2018).*

Li, W. et al. (Jun. 12, 2018) CancerDetector: ultrasensitive and non-invasive cancer detection at the resolution of individual reads using cell-free DNA methylation sequencing data. NAR vol. 46, No. 15, e89, 15 pages and some supplemental material. (Year: 2018).*

Agresti, A., "An Introduction to Categorical Data Analysis," Second Edition, 2007, Chapter 5, John Wiley & Son, New York, pp. 137-172.

Breiman, L., "Random Forests—Random Features," Technical Report 567, Sep. 1999, pp. 1-29.

Duda, "Pattern Classification," Second Edition, John Wiley & Sons, Inc., 2001, pp. 259, 262-265.

Fernandes, K. et al. "Transfer Learning with Partial Observability Applied to Cervical Cancer Screening," Pattern Recognition and Image Analysis: 8th Iberian Conference Proceedings, May 2017, pp. 243-250.

(Continued)

*Primary Examiner* — Mary K Zeman

(74) *Attorney, Agent, or Firm* — Fenwick & West LLP

(57) ABSTRACT

Methods and systems for detecting cancer and/or determining a cancer tissue of origin are disclosed. Fragments are grouped into genomic regions, wherein a region model is trained for each genomic region. Fragments are input into the region models, and the outputs are used to generate a feature vector for cancer classification. In one embodiment, the region models are shallow neural networks configured to generate a score indicating a likelihood that a fragment is derived from a cancer biological sample. The feature vector is determined based on counts of fragments having scores above threshold scores for the various genomic regions. In another embodiment, the regions models are configured to generate a region embedding for an input methylation embedding of a fragment. The region embeddings are pooled by region and then pooled again to generate the feature vector.

15 Claims, 17 Drawing Sheets

(56) References Cited

OTHER PUBLICATIONS

Heitzer, E. et al., "Current and future perspectives of liquid biopsies in genomics-driven oncology," Nature Reviews, vol. 20, Feb. 2019, pp. 71-88.
Klein, E. et al., "Development of a comprehensive cell-free DNA (cfDNA) assay for early detection of multiple tumor types: The Circulating Cell-free Genome Atlas (CCGA) study," 2018 ASCO Annual Meeting, Abstract 12021, Jun. 2018, one page.
Liu, M. et al., "Genome-wide Cell-free DNA (cfDNA) Methylation Signatures and Effect on Tissue of Origin (TOO) Performance," ASCO 2019, Jun. 2019, one page.
Masser, D.R. et al., "Targeted DNA Methylation Analysis by Next-generation Sequencing," J. Vis. Exp. (96), e52488, Feb. 24, 2015, pp. 1-11.
O'Marcaigh, A.S. et al., "Estimating the Predictive Value of a Diagnostic Test," Clinical Pediatrics 32(8), 1993, pp. 485-491.
PCT International Search Report and Written Opinion, PCT Application No. PCT/US2021/024731, Sep. 8, 2021, 23 pages.
PCT Invitation to Pay, PCT Application No. PCT/US2021/024731, Jul. 14, 2021, 18 pages.
U.S. Appl. No. 62/642,480, entitled "Methylation Fragment Anomaly Detection," filed Mar. 13, 2018, Inventors: Samuel S. Gross and Konstantin Davydov.
U.S. Appl. No. 62/847,223, entitled "Model-Based Featurization and Classification," filed May 13, 2019, Inventors: Alexander P. Fields, John F. Beausang, Oliver Claude Venn, and Arash Jamshidi.
U.S. Appl. No. 62/948,129, entitled "Cancer Classification using Patch Convolutional Neural Networks," filed Dec. 13, 2019.
U.S. Appl. No. 62/985,258, filed Mar. 4, 2020.
Vincent, P. et al., "Stacked Denoising Autoencoders: Learning Useful Representations in a Deep Network with a Local Denoising Criterion," Journal of Machine Learning Research 11, Dec. 2010, pp. 3371-3408.
Yoon, B-J., "Hidden Markov Models and their Applications in Biological Sequence Analysis," Current Genomics, vol. 10, 2009, pp. 402-415.
Zheng, C. et al., "Predicting cancer origins with a DNA methylation-based deep neural network model," PLoS One, May 8, 2020, pp. 1-17.
Ziller, M. J. et al., "Coverage recommendations for methylation analysis by whole genome bisulfite sequencing," Nature Methods 12(3), Mar. 2015, pp. 230-232.

* cited by examiner

600

1420

1410

CANCER CLASSIFICATION WITH GENOMIC REGION MODELING

RELATED APPLICATIONS

This application claims the benefit of and priority to U.S. Provisional Application No. 63/003,087 filed on Mar. 31, 2020, and U.S. Provisional Application No. 63/144,380 filed on Feb. 1, 2021, both of which are incorporated by reference in their entireties. All other publications, patents, and patent applications described herein are incorporated by reference in their entireties. In the event of a conflict between a term herein and a term in an incorporated reference, the term herein controls.

BACKGROUND

Field of Art

Deoxyribonucleic acid (DNA) methylation plays an important role in regulating gene expression. Aberrant DNA methylation has been implicated in many disease processes, including cancer. DNA methylation profiling using methylation sequencing (e.g., whole genome bisulfite sequencing (WGBS)) is increasingly recognized as a valuable diagnostic tool for detection, diagnosis, and/or monitoring of cancer. For example, specific patterns of differentially methylated regions and/or allele specific methylation patterns may be useful as molecular markers for non-invasive diagnostics using circulating cell-free (cf) DNA. However, there remains a need in the art for improved methods for analyzing methylation sequencing data from cell-free DNA for the detection, diagnosis, and/or monitoring of diseases, such as cancer.

The present disclosure is directed to addressing one or more of these above-referenced challenges. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

Early detection of a disease state (such as cancer) in subjects is important as it allows for earlier treatment and therefore a greater chance for survival. Sequencing of DNA fragments in a cell-free (cf) DNA sample can be used to identify features that can be used for disease classification. For example, in cancer assessment, cell-free DNA-based features (such as a presence or absence of somatic variant, a methylation status, or other genetic aberrations) from a blood sample can provide insight into whether a subject may have cancer, and further insight on what type of cancer the subject may have and what stage the cancer may have progressed to. Towards that end, this description includes systems and methods for analyzing cell-free DNA sequencing data for determining a subject's likelihood of having a disease. The description can address the shortcomings identified in the background by providing systems and methods of obtaining features for determining a cancer state of a subject.

An analytics system can process a multitude of sequencing data from a plurality of samples (e.g., a plurality of cancer and non-cancer samples) to identify features that are subsequently utilized for cancer classification. With the sequencing data, the analytics system can train and deploy a cancer classifier for generating a cancer prediction for a test sample. The cancer classifier may be a machine-learned model trained with machine-learning algorithms.

The analytics system can implement modeling of each genomic region in the featurization of a sample. Generally, the cancer classification process can implement a plurality of region models, a featurization module, and a cancer classifier. A methylation embedding model may also be implemented and applied to a cfDNA fragment to produce a methylation embedding. Each region model may be applied to a cfDNA fragment to produce a cancer score indicating a likelihood that the cfDNA fragment is derived from a cancer biological sample. Alternatively or additionally, each region model may be applied to a cfDNA fragment (or the methylation embedding thereof) to produce a region embedding. A featurization module can be applied to the outputs of the region models and generate a feature vector for the sample. In embodiments where the region model outputs are cancer scores, the featurization module may produce a feature by counting fragments in each genomic region that surpass a threshold score determined for the genomic region. In embodiments where the region model outputs are region embeddings, the featurization module may pool the region embeddings to generate the feature vector. The pooling may include two pooling steps—a first pooling step to pool region embeddings to generate an aggregate region vector for each genomic region, and a second pooling step to pool aggregate region vectors of the genomic regions into a feature vector.

The methylation embedding model, the region models, the featurization module, and the cancer classifier may be machine-learned models. As such, the analytics system may implement machine-learning algorithms in training each component of the cancer classification process. For example, the methylation embedding model, the region models, the featurization module, and the cancer classifier can be neural networks, decision trees, random forests, regressions, other machine-learning algorithms, etc.

The analytics system can train the components of the cancer classification process with training samples. The training samples may have a known label of cancer or non-cancer. Additionally, the training samples having cancer may have a label of a particular cancer type. The analytics system may train the components independently or concurrently.

During deployment, the analytics system can generate a feature vector for a test sample. The analytics system then inputs the feature vector for the test sample into the cancer classifier which returns a cancer prediction. The cancer prediction may be a binary prediction between cancer and non-cancer, e.g., a likelihood of having cancer. The cancer prediction may be a multiclass prediction between a plurality of cancer types, e.g., a prediction value for each cancer type classified.

Figure 1A:
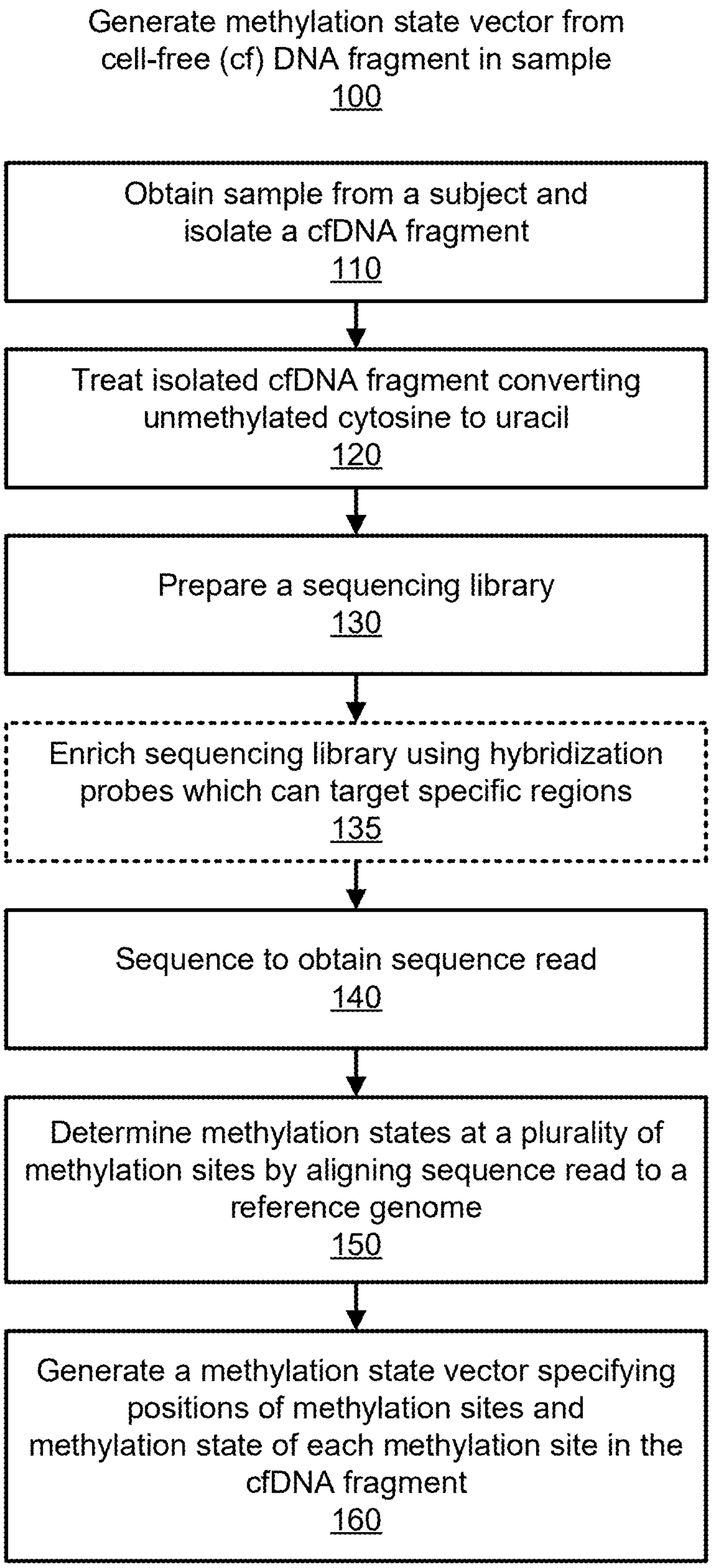
FIG. 1A is an exemplary flowchart describing a process of sequencing a fragment of cell-free (cf) DNA to obtain a methylation state vector, according to one or more embodiments.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

I. Overview

I.A. Overview of Methylation

In accordance with the present description, cfDNA fragments from an individual are treated, for example by converting unmethylated cytosines to uracils, sequenced and the sequence reads compared to a reference genome to identify the methylation states at specific CpG sites within the DNA fragments. Each CpG site may be methylated or unmethylated. Identification of anomalously methylated fragments, in comparison to healthy individuals, may provide insight into a subject's cancer status. DNA methylation anomalies (compared to healthy controls) can cause different effects, which may contribute to cancer. Various challenges arise in the identification of anomalously methylated cfDNA fragments. First off, determining a DNA fragment to be anomalously methylated can hold weight in comparison with a group of control individuals, such that if the control group is small in number, the determination loses confidence due to statistical variability within the smaller size of the control group. Additionally, among a group of control individuals, methylation status can vary which can be difficult to account for when determining a subject's DNA fragments to be anomalously methylated. On another note, methylation of a cytosine at a CpG site can causally influence methylation at a subsequent CpG site. To encapsulate this dependency can be another challenge in itself.

Methylation can typically occur in deoxyribonucleic acid (DNA) when a hydrogen atom on the pyrimidine ring of a cytosine base is converted to a methyl group, forming 5-methylcytosine. In particular, methylation can occur at dinucleotides of cytosine and guanine referred to herein as "CpG sites". In other instances, methylation may occur at a cytosine not part of a CpG site or at another nucleotide that is not cytosine; however, these are rarer occurrences. In this present disclosure, methylation is discussed in reference to CpG sites for the sake of clarity. Anomalous DNA methylation can be identified as hypermethylation or hypomethylation, both of which may be indicative of cancer status. Throughout this disclosure, hypermethylation and hypomethylation can be characterized for a DNA fragment, if the DNA fragment comprises more than a threshold number of CpG sites with more than a threshold percentage of those CpG sites being methylated or unmethylated.

The principles described herein can be equally applicable for the detection of methylation in a non-CpG context, including non-cytosine methylation. In such embodiments, the wet laboratory assay used to detect methylation may vary from those described herein. Further, the methylation state vectors discussed herein may contain elements that are generally sites where methylation has or has not occurred (even if those sites are not CpG sites specifically). With that substitution, the remainder of the processes described herein can be the same, and consequently the inventive concepts described herein can be applicable to those other forms of methylation.

I.B. Definitions

The term "cell free nucleic acid" or "cfNA" refers to nucleic acid fragments that circulate in an individual's body (e.g., blood) and originate from one or more healthy cells and/or from one or more unhealthy cells (e.g., cancer cells). The term "cell free DNA," or "cfDNA" refers to deoxyribonucleic acid fragments that circulate in an individual's body (e.g., blood). Additionally, cfNAs or cfDNA in an individual's body may come from other non-human sources.

The term "genomic nucleic acid," "genomic DNA," or "gDNA" refers to nucleic acid molecules or deoxyribonucleic acid molecules obtained from one or more cells. In various embodiments, gDNA can be extracted from healthy cells (e.g., non-tumor cells) or from tumor cells (e.g., a biopsy sample). In some embodiments, gDNA can be extracted from a cell derived from a blood cell lineage, such as a white blood cell. The term "circulating tumor DNA" or "ctDNA" refers to nucleic acid fragments that originate from tumor cells or other types of cancer cells, and which may be released into a bodily fluid of an individual (e.g., blood, sweat, urine, or saliva) as result of biological processes such as apoptosis or necrosis of dying cells or actively released by viable tumor cells. The term "DNA fragment," "fragment," or "DNA molecule" may generally refer to any deoxyribonucleic acid fragments, i.e., cfDNA, gDNA, ctDNA, etc.

The term "anomalous fragment," "anomalously methylated fragment," or "fragment with an anomalous methylation pattern" refers to a fragment that has anomalous methylation of CpG sites. Anomalous methylation of a fragment may be determined using probabilistic models to identify unexpectedness of observing a fragment's methylation pattern in a control group.

The term "unusual fragment with extreme methylation" or "UFXM" refers to a hypomethylated fragment or a hypermethylated fragment. A hypomethylated fragment and a hypermethylated fragment refers to a fragment with at least some number of CpG sites (e.g., 5) that have over some threshold percentage (e.g., 90%) of methylation or unmethylation, respectively.

As used herein, the term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. "About" can mean a range of ±20%, ±10%, ±5%, or ±1% of a given value. The term "about" or "approximately" can mean within an order of magnitude, within 5-fold, or within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

As used herein, the term "biological sample," "patient sample," or "sample" refers to any sample taken from a subject, which can reflect a biological state associated with the subject, and that includes cell-free DNA. Examples of biological samples include, but are not limited to, blood, whole blood, plasma, serum, urine, cerebrospinal fluid, fecal, saliva, sweat, tears, pleural fluid, pericardial fluid, or peritoneal fluid of the subject. A biological sample can include any tissue or material derived from a living or dead subject. A biological sample can be a cell-free sample. A biological sample can comprise a nucleic acid (e.g., DNA or RNA) or a fragment thereof. The term "nucleic acid" can refer to deoxyribonucleic acid (DNA), ribonucleic acid (RNA) or any hybrid or fragment thereof. The nucleic acid in the sample can be a cell-free nucleic acid. A sample can be a liquid sample or a solid sample (e.g., a cell or tissue sample). A biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. A biological sample can be a stool sample. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). A biological sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis.

As used herein, the term "cancer" or "tumor" refers to an abnormal mass of tissue in which the growth of the mass surpasses and is not coordinated with the growth of normal tissue. A cancer or tumor can be defined as "benign" or "malignant" depending on the following characteristics: degree of cellular differentiation including morphology and functionality, rate of growth, local invasion and metastasis. A "benign" tumor can be well-differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites.

As used herein, the term "cancer condition" refers to a condition of a sample relative to cancer, wherein each potential characteristic and/or measure of the condition refers to a "state" of the cancer condition. For example, a sample can have a cancer condition that is "cancer" or "non-cancer." Alternatively, a cancer condition can be a primary site of origin or a tissue-of-origin, such as breast cancer, lung cancer, prostate cancer, colorectal cancer, renal cancer, uterine cancer, pancreatic cancer, cancer of the esophagus, lymphoma, head/neck cancer, ovarian cancer, hepatobiliary cancer, melanoma, cervical cancer, multiple myeloma, leukemia, thyroid cancer, bladder cancer, and gastric cancer. A cancer condition can be a cancer type or a tumor of a certain cancer type, or a fraction thereof. A cancer condition can also be a survival metric, which can be a predetermined likelihood of survival for a predetermined period of time. Multiple samples from a single subject can have different cancer conditions or the same cancer condition. Multiple subjects can have different cancer conditions or the same cancer condition.

As used herein, Circulating Cell-free Genome Atlas or "CCGA" is defined as an observational clinical study that prospectively collects blood and tissue from newly diagnosed cancer patients as well as blood only from subjects who do not have a cancer diagnosis. The purpose of the study is to develop a pan-cancer classifier that distinguishes cancer from non-cancer and identifies tissue of origin. Example 1 provides further details of the CCGA dataset.

As used herein, the term "false-positive" (FP) refers to a subject that does not have a condition. False-positive can refer to a subject that does not have a tumor, a cancer, a pre-cancerous condition (e.g., a pre-cancerous lesion), a localized or a metastasized cancer, a non-malignant disease, or is otherwise healthy. The term "false-positive" can refer to a subject that does not have a condition, but is identified as having the condition by an assay or method of the present disclosure. As used herein, the term "false-negative" (FN) refers to a subject that has a condition. False-negative can refer to a subject that has a tumor, a cancer, a pre-cancerous condition (e.g., a pre-cancerous lesion), a localized or a metastasized cancer, or a non-malignant disease. The term false-negative can refer to a subject that has a condition but is identified as not having the condition by an assay or method of the present disclosure.

As used herein, the phrase "healthy," refers to a subject possessing good health. A healthy subject can demonstrate an absence of any malignant or non-malignant disease. A "healthy individual" can have other diseases or conditions, unrelated to the condition being assayed, which can normally not be considered "healthy."

As used herein, the term "methylation" refers to a modification of deoxyribonucleic acid (DNA) where a hydrogen atom on the pyrimidine ring of a cytosine base is converted to a methyl group, forming 5-methylcytosine. In particular, methylation tends to occur at dinucleotides of cytosine and guanine referred to herein as "CpG sites." In other instances, methylation may occur at a cytosine not part of a CpG site or at another nucleotide that's not cytosine; however, these are rarer occurrences. Anomalous cfDNA methylation can be identified as hypermethylation or hypomethylation, both of which may be indicative of cancer status. DNA methylation anomalies (compared to healthy controls) can cause different effects, which may contribute to cancer. The principles described herein are equally applicable for the detection of methylation in a CpG context and non-CpG context, including non-cytosine methylation. Further, the methylation state vectors may contain elements that are generally vectors of sites where methylation has or has not occurred (even if those sites are not CpG sites specifically).

As used interchangeably herein, the term "methylation fragment" or "nucleic acid methylation fragment" refers to a sequence of methylation states for each CpG site in a plurality of CpG sites, determined by a methylation sequencing of nucleic acids (e.g., a nucleic acid molecule and/or a nucleic acid fragment). In a methylation fragment, a location and methylation state for each CpG site in the nucleic acid fragment is determined based on the alignment of the sequence reads (e.g., obtained from sequencing of the nucleic acids) to a reference genome. A nucleic acid methylation fragment comprises a methylation state of each CpG site in a plurality of CpG sites (e.g., a methylation state vector), which specifies the location of the nucleic acid fragment in a reference genome (e.g., as specified by the position of the first CpG site in the nucleic acid fragment using a CpG index, or another similar metric) and the number of CpG sites in the nucleic acid fragment. Alignment of a sequence read to a reference genome, based on a methylation sequencing of a nucleic acid molecule, can be performed using a CpG index. As used herein, the term "CpG index" refers to a list of each CpG site in the plurality of CpG sites (e.g., CpG 1, CpG 2, CpG 3, etc.) in a reference genome, such as a human reference genome, which can be in electronic format. The CpG index further comprises a corresponding genomic location, in the corresponding reference genome, for each respective CpG site in the CpG index. Each CpG site in each respective nucleic acid methylation fragment is thus indexed to a specific location in the respective reference genome, which can be determined using the CpG index.

As used herein, the term "true positive" (TP) refers to a subject having a condition. "True positive" can refer to a subject that has a tumor, a cancer, a pre-cancerous condition (e.g., a pre-cancerous lesion), a localized or a metastasized cancer, or a non-malignant disease. "True positive" can refer to a subject having a condition, and is identified as having the condition by an assay or method of the present disclosure. As used herein, the term "true negative" (TN) refers to a subject that does not have a condition or does not have a detectable condition. True negative can refer to a subject that does not have a disease or a detectable disease, such as a tumor, a cancer, a pre-cancerous condition (e.g., a pre-cancerous lesion), a localized or a metastasized cancer, a non-malignant disease, or a subject that is otherwise healthy. True negative can refer to a subject that does not have a condition or does not have a detectable condition, or is identified as not having the condition by an assay or method of the present disclosure.

As used herein, the term "reference genome" refers to any particular known, sequenced or characterized genome, whether partial or complete, of any organism or virus that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). In some embodiments, sequence reads (e.g., single-end or paired-end reads) can be generated from one or both strands of a targeted nucleic acid fragment. The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

As used herein, the terms "sequencing" and the like as used herein refers generally to any and all biochemical processes that may be used to determine the order of biological macromolecules such as nucleic acids or proteins. For example, sequencing data can include all or a portion of the nucleotide bases in a nucleic acid molecule such as a DNA fragment.

As used herein, the term "sequencing depth," is interchangeably used with the term "coverage" and refers to the number of times a locus is covered by a consensus sequence read corresponding to a unique nucleic acid target molecule aligned to the locus; e.g., the sequencing depth is equal to the number of unique nucleic acid target molecules covering the locus. The locus can be as small as a nucleotide, or as large as a chromosome arm, or as large as an entire genome. Sequencing depth can be expressed as "Yx", e.g., 50×, 100×, etc., where "Y" refers to the number of times a locus is covered with a sequence corresponding to a nucleic acid target; e.g., the number of times independent sequence information is obtained covering the particular locus. In some embodiments, the sequencing depth corresponds to the number of genomes that have been sequenced. Sequencing depth can also be applied to multiple loci, or the whole genome, in which case Y can refer to the mean or average number of times a locus or a haploid genome, or a whole genome, respectively, is sequenced. When a mean depth is quoted, the actual depth for different loci included in the dataset can span over a range of values. Ultra-deep sequencing can refer to at least 100× in sequencing depth at a locus.

As used herein, the term "sensitivity" or "true positive rate" (TPR) refers to the number of true positives divided by the sum of the number of true positives and false negatives. Sensitivity can characterize the ability of an assay or method to correctly identify a proportion of the population that truly has a condition. For example, sensitivity can characterize the ability of a method to correctly identify the number of subjects within a population having cancer. In another example, sensitivity can characterize the ability of a method to correctly identify the one or more markers indicative of cancer.

As used herein, the term "specificity" or "true negative rate" (TNR) refers to the number of true negatives divided by the sum of the number of true negatives and false positives. Specificity can characterize the ability of an assay or method to correctly identify a proportion of the population that truly does not have a condition. For example, specificity can characterize the ability of a method to correctly identify the number of subjects within a population not having cancer. In another example, specificity characterizes the ability of a method to correctly identify one or more markers indicative of cancer.

As used herein, the term "subject" refers to any living or non-living organism, including but not limited to a human (e.g., a male human, female human, fetus, pregnant female, child, or the like), a non-human animal, a plant, a bacterium, a fungus or a protist. Any human or non-human animal can serve as a subject, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale, and shark. In some embodiments, a subject is a male or female of any stage (e.g., a man, a woman or a child). A subject from whom a sample is taken, or is treated by any of the methods or compositions described herein can be of any age and can be an adult, infant or child.

As used herein, the term "tissue" can correspond to a group of cells that group together as a functional unit. More than one type of cell can be found in a single tissue. Different types of tissue may consist of different types of cells (e.g., hepatocytes, alveolar cells or blood cells), but also can correspond to tissue from different organisms (mother vs. fetus) or to healthy cells vs. tumor cells. The term "tissue" can generally refer to any group of cells found in the human body (e.g., heart tissue, lung tissue, kidney tissue, nasopharyngeal tissue, oropharyngeal tissue). In some aspects, the term "tissue" or "tissue type" can be used to refer to a tissue from which a cell-free nucleic acid originates. In one example, viral nucleic acid fragments can be derived from blood tissue. In another example, viral nucleic acid fragments can be derived from tumor tissue.

As used herein, the term "genomic" refers to a characteristic of the genome of an organism. Examples of genomic characteristics include those relating to the primary nucleic acid sequence of all or a portion of the genome (e.g., the presence or absence of a nucleotide polymorphism, indel, sequence rearrangement, mutational frequency, etc.), the copy number of one or more particular nucleotide sequences within the genome (e.g., copy number, allele frequency fractions, single chromosome or entire genome ploidy, etc.), the epigenetic status of all or a portion of the genome (e.g., covalent nucleic acid modifications such as methylation, histone modifications, nucleosome positioning, etc.), the expression profile of the organism's genome (e.g., gene expression levels, isotype expression levels, gene expression ratios, etc.).

The terminology used herein is for the purpose of describing particular cases only and is not intended to be limiting. As used herein, the singular forms "a," "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

II. Sample Processing

II.A. Generating Methylation State Vectors for DNA Fragments

FIG. 1A is an exemplary flowchart describing a process 100 of sequencing a fragment of cell-free (cf) DNA to obtain a methylation state vector, according to one or more embodiments. In order to analyze DNA methylation, an analytics system first obtains 110 a sample from an individual comprising a plurality of cfDNA molecules. Generally, samples may be from healthy individuals, subjects known to have or suspected of having cancer, or subjects where no prior information is known. The test sample may be a sample selected from the group consisting of blood, plasma, serum, urine, fecal, and saliva samples. Alternatively, the test sample may comprise a sample selected from the group consisting of whole blood, a blood fraction (e.g., white blood cells (WBCs)), a tissue biopsy, pleural fluid, pericardial fluid, cerebral spinal fluid, and peritoneal fluid. In additional embodiments, the process 100 may be applied to sequence other types of DNA molecules.

From the sample, the analytics system can isolate each cfDNA molecule. The cfDNA molecules can be treated to convert unmethylated cytosines to uracils. In one embodiment, the method uses a bisulfite treatment of the DNA which converts the unmethylated cytosines to uracils without converting the methylated cytosines. For example, a commercial kit such as the EZ DNA Methylation™—Gold, EZ DNA Methylation™—Direct or an EZ DNA Methylation™—Lightning kit (available from Zymo Research Corp (Irvine, CA)) is used for the bisulfite conversion. In another embodiment, the conversion of unmethylated cytosines to uracils is accomplished using an enzymatic reaction. For example, the conversion can use a commercially available kit for conversion of unmethylated cytosines to uracils, such as APOBEC-Seq (NEBiolabs, Ipswich, MA).

From the converted cfDNA molecules, a sequencing library can be prepared 130. During library preparation, unique molecular identifiers (UMI) can be added to the nucleic acid molecules (e.g., DNA molecules) through adapter ligation. The UMIs can be short nucleic acid sequences (e.g., 4-10 base pairs) that are added to ends of DNA fragments (e.g., DNA molecules fragmented by physical shearing, enzymatic digestion, and/or chemical fragmentation) during adapter ligation. UMIs can be degenerate base pairs that serve as a unique tag that can be used to identify sequence reads originating from a specific DNA fragment. During PCR amplification following adapter ligation, the UMIs can be replicated along with the attached DNA fragment. This can provide a way to identify sequence reads that came from the same original fragment in downstream analysis.

Optionally, the sequencing library may be enriched 135 for cfDNA molecules, or genomic regions, that are informative for cancer status using a plurality of hybridization probes. The hybridization probes can be short oligonucleotides capable of hybridizing to particularly specified cfDNA molecules, or targeted regions, and enriching for those fragments or regions for subsequent sequencing and analysis. Hybridization probes may be used to perform a targeted, high-depth analysis of a set of specified CpG sites of interest to the researcher. Hybridization probes can be tiled across one or more target sequences at a coverage of 1×, 2×, 3×, 4×, 5×, 6×, 7×, 8×, 9×, 10×, or more than 10×. For example, hybridization probes tiled at a coverage of 2× comprises overlapping probes such that each portion of the target sequence is hybridized to 2 independent probes. Hybridization probes can be tiled across one or more target sequences at a coverage of less than 1×.

In one embodiment, the hybridization probes are designed to enrich for DNA molecules that have been treated (e.g., using bisulfite) for conversion of unmethylated cytosines to uracils. During enrichment, hybridization probes (also referred to herein as "probes") can be used to target and pull down nucleic acid fragments informative for the presence or absence of cancer (or disease), cancer status, or a cancer classification (e.g., cancer class or tissue of origin). The probes may be designed to anneal (or hybridize) to a target (complementary) strand of DNA. The target strand may be the "positive" strand (e.g., the strand transcribed into mRNA, and subsequently translated into a protein) or the complementary "negative" strand. The probes may range in length from 10s, 100s, or 1000s of base pairs. The probes can be designed based on a methylation site panel. The probes can be designed based on a panel of targeted genes to analyze particular mutations or target regions of the genome (e.g., of the human or another organism) that are suspected to correspond to certain cancers or other types of diseases. Moreover, the probes may cover overlapping portions of a target region.

Once prepared, the sequencing library or a portion thereof can be sequenced to obtain a plurality of sequence reads. The sequence reads may be in a computer-readable, digital format for processing and interpretation by computer software. The sequence reads may be aligned to a reference genome to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene. A sequence read can be comprised of a read pair denoted as $R_1$ and $R_2$. For example, the first read $R_1$ may be sequenced from a first end of a nucleic acid fragment whereas the second read $R_2$ may be sequenced from the second end of the nucleic acid fragment. Therefore, nucleotide base pairs of the first read $R_1$ and second read $R_2$ may be aligned consistently (e.g., in opposite orientations) with nucleotide bases of the reference genome. Alignment position information derived from the read pair $R_1$ and $R_2$ may include a beginning position in the reference genome that corresponds to an end of a first read (e.g., $R_1$) and an end position in the reference genome that corresponds to an end of a second read (e.g., $R_2$). In other words, the beginning position and end position in the reference genome can represent the likely location within the reference genome to which the nucleic acid fragment corresponds. An output file having SAM (sequence alignment map) format or BAM (binary) format may be generated and output for further analysis such as methylation state determination.

From the sequence reads, the analytics system determines 150 a location and methylation state for each CpG site based on alignment to a reference genome. The analytics system generates 160 a methylation state vector for each fragment specifying a location of the fragment in the reference genome (e.g., as specified by the position of the first CpG site in each fragment, or another similar metric), a number of CpG sites in the fragment, and the methylation state of each CpG site in the fragment whether methylated (e.g., denoted as M), unmethylated (e.g., denoted as U), or indeterminate (e.g., denoted as I). Observed states can be states of methylated and unmethylated; whereas, an unobserved state is indeterminate. Indeterminate methylation states may originate from sequencing errors and/or disagreements between methylation states of a DNA fragment's complementary strands. The methylation state vectors may be stored in temporary or persistent computer memory for later use and processing. Further, the analytics system may remove duplicate reads or duplicate methylation state vectors from a single sample. The analytics system may determine that a certain fragment with one or more CpG sites has an indeterminate methylation status over a threshold number or percentage, and may exclude such fragments or selectively include such fragments but build a model accounting for such indeterminate methylation statuses.

Figure 1B:
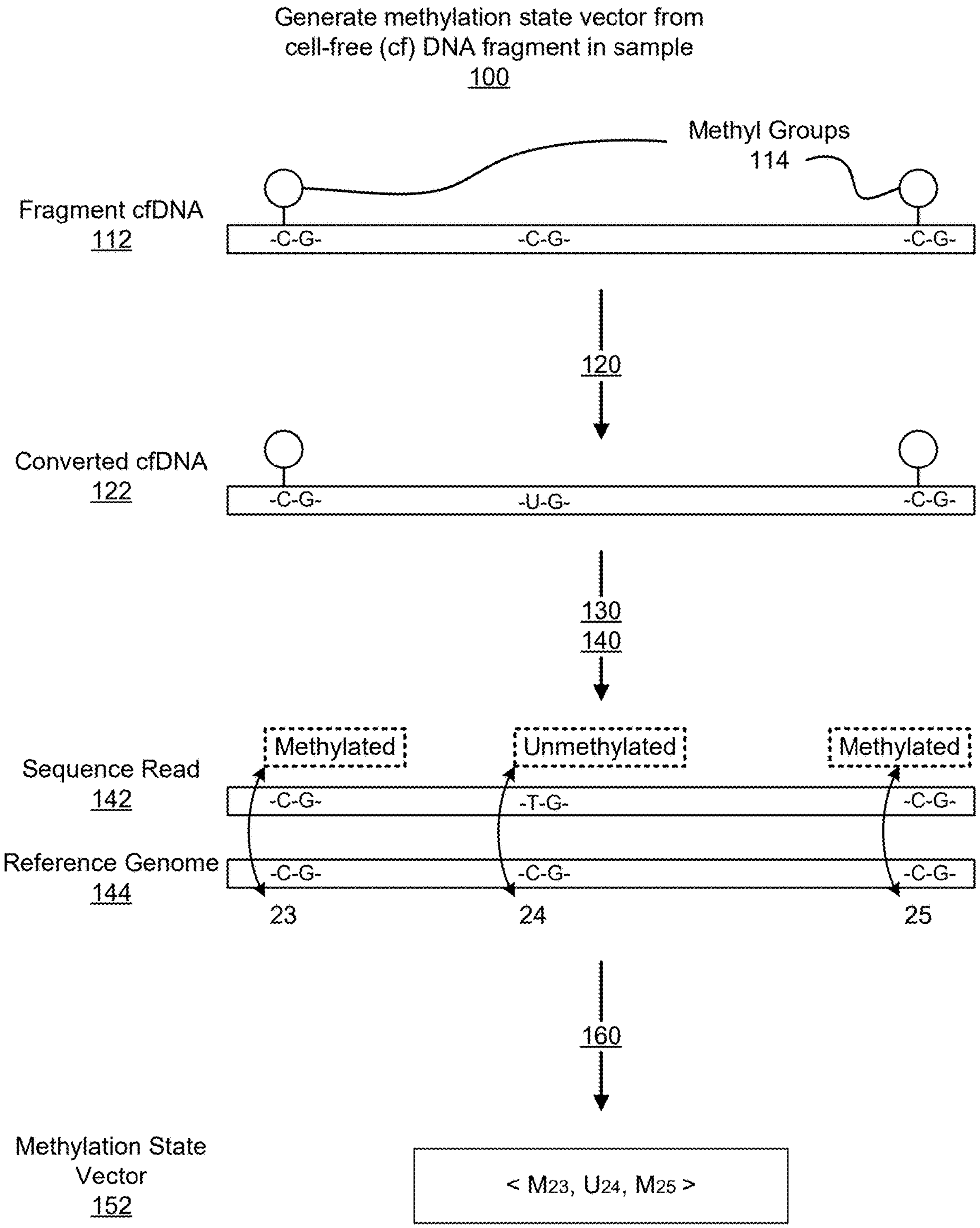
FIG. 1B illustrates the process of FIG. 1A of sequencing a fragment of cell-free (cf) DNA to obtain a methylation state vector, according to one or more embodiments.

FIG. 1B is an illustration of the process 100 of FIG. 1A of sequencing a cfDNA molecule to obtain a methylation state vector, according to one or more embodiments. As an example, the analytics system receives a cfDNA molecule 112 that contains three CpG sites. As shown, the first and third CpG sites of the cfDNA molecule 112 are methylated 114. During the treatment step 120, the cfDNA molecule 112 is converted to generate a converted cfDNA molecule 122. During the treatment 120, the second CpG site which is unmethylated has its cytosine converted to uracil. However, the first and third CpG sites may not be converted.

After conversion, a sequencing library 130 is prepared and sequenced 140 to generate a sequence read 142. The analytics system aligns 150 the sequence read 142 to a reference genome 144. The reference genome 144 provides the context as to what position in a human genome the fragment cfDNA originates from. In this simplified example, the analytics system aligns 150 the sequence read 142 such that the three CpG sites correlate to CpG sites 23, 24, and 25 (arbitrary reference identifiers used for convenience of description). The analytics system can thus generate information both on methylation status of all CpG sites on the cfDNA molecule 112 and the position in the human genome that the CpG sites map to. As shown, the CpG sites on sequence read 142 which are methylated are read as cytosines. In this example, the cytosines appear in the sequence read 142 in the first and third CpG site which allows one to infer that the first and third CpG sites in the original cfDNA molecule are methylated. Whereas, the second CpG site can be read as a thymine (U is converted to T during the sequencing process), and thus, one can infer that the second CpG site is unmethylated in the original cfDNA molecule. With these two pieces of information, the methylation status and location, the analytics system generates 160 a methylation state vector 152 for the fragment cfDNA 112. In this example, the resulting methylation state vector 152 is $<M_{23}, U_{24}, M_{25}>$, wherein M corresponds to a methylated CpG site, U corresponds to an unmethylated CpG site, and the subscript number corresponds to a position of each CpG site in the reference genome.

One or more alternative sequencing methods can be used for obtaining sequence reads from nucleic acids in a biological sample. The one or more sequencing methods can comprise any form of sequencing that can be used to obtain a number of sequence reads measured from nucleic acids (e.g., cell-free nucleic acids), including, but not limited to, high-throughput sequencing systems such as the Roche 454 platform, the Applied Biosystems SOLID platform, the Helicos True Single Molecule DNA sequencing technology, the sequencing-by-hybridization platform from Affymetrix Inc., the single-molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and Nanopore sequencing can also be used to obtain sequence reads from the nucleic acids (e.g., cell-free nucleic acids) in the biological sample. Sequencing-by-synthesis and reversible terminator-based sequencing (e.g., Illumina's Genome Analyzer; Genome Analyzer II; HISEQ 2000; HISEQ 2500 (Illumina, San Diego Calif.)) can be used to obtain sequence reads from the cell-free nucleic acid obtained from a biological sample of a training subject in order to form the genotypic dataset. Millions of cell-free nucleic acid (e.g., DNA) fragments can be sequenced in parallel. In one example of this type of sequencing technology, a flow cell is used that contains an optically transparent slide with eight individual lanes on the surfaces of which are bound oligonucleotide anchors (e.g., adaptor primers). A cell-free nucleic acid sample can include a signal or tag that facilitates detection. The acquisition of sequence reads from the cell-free nucleic acid obtained from the biological sample can include obtaining quantification information of the signal or tag via a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

The one or more sequencing methods can comprise a whole-genome sequencing assay. A whole-genome sequencing assay can comprise a physical assay that generates sequence reads for a whole genome or a substantial portion of the whole genome which can be used to determine large variations such as copy number variations or copy number aberrations. Such a physical assay may employ whole-genome sequencing techniques or whole-exome sequencing techniques. A whole-genome sequencing assay can have an average sequencing depth of at least 1×, 2×, 3×, 4×, 5×, 6×, 7×, 8×, 9×, 10×, at least 20×, at least 30×, or at least 40× across the genome of the test subject. In some embodiments, the sequencing depth is about 30,000×. The one or more sequencing methods can comprise a targeted panel sequencing assay. A targeted panel sequencing assay can have an average sequencing depth of at least 50,000×, at least 55,000×, at least 60,000×, or at least 70,000× sequencing depth for the targeted panel of genes. The targeted panel of genes can comprise between 450 and 500 genes. The targeted panel of genes can comprise a range of 500±5 genes, a range of 500±10 genes, or a range of 500±25 genes.

The one or more sequencing methods can comprise paired-end sequencing. The one or more sequencing methods can generate a plurality of sequence reads. The plurality of sequence reads can have an average length ranging between 10 and 600, between 50 and 400, or between 100 and 300. The one or more sequencing methods can comprise a methylation sequencing assay. The methylation sequencing can be i) whole-genome methylation sequencing or ii) targeted DNA methylation sequencing using a plurality of nucleic acid probes. For example, the methylation sequencing is whole-genome bisulfite sequencing (e.g., WGBS). The methylation sequencing can be a targeted DNA methylation sequencing using a plurality of nucleic acid probes targeting the most informative regions of the methylome, a unique methylation database and prior prototype whole-genome and targeted sequencing assays.

The methylation sequencing can detect one or more 5-methylcytosine (5mC) and/or 5-hydroxymethylcytosine (5hmC) in respective nucleic acid methylation fragments. The methylation sequencing can comprise conversion of one or more unmethylated cytosines or one or more methylated cytosines, in respective nucleic acid methylation fragments, to a corresponding one or more uracils. The one or more uracils can be detected during the methylation sequencing as one or more corresponding thymines. The conversion of one or more unmethylated cytosines or one or more methylated cytosines can comprise a chemical conversion, an enzymatic conversion, or combinations thereof.

For example, bisulfite conversion involves converting cytosine to uracil while leaving methylated cytosines (e.g., 5-methylcytosine or 5-mC) intact. In some DNA, about 95% of cytosines may not methylated in the DNA, and the resulting DNA fragments may include many uracils which are represented by thymines. Enzymatic conversion processes may be used to treat the nucleic acids prior to sequencing, which can be performed in various ways. One example of a bisulfite-free conversion comprises a bisulfite-free and base-resolution sequencing method, TET-assisted pyridine borane sequencing (TAPS), for non-destructive and direct detection of 5-methylcytosine and 5-hydroxymethylcytosine without affecting unmodified cytosines. The methylation state of a CpG site in the corresponding plurality of CpG sites in the respective nucleic acid methylation fragment can be methylated when the CpG site is determined by the methylation sequencing to be methylated, and unmethylated when the CpG site is determined by the methylation sequencing to not be methylated.

A methylation sequencing assay (e.g., WGBS and/or targeted methylation sequencing) can have an average sequencing depth including but not limited to up to about 1,000×, 2,000×, 3,000×, 5,000×, 10,000×, 15,000×, 20,000×, or 30,000×. The methylation sequencing can have a sequencing depth that is greater than 30,000×, e.g., at least 40,000× or 50,000×. A whole-genome bisulfite sequencing method can have an average sequencing depth of between 20× and 50×, and a targeted methylation sequencing method has an average effective depth of between 100× and 1000×, where effective depth can be the equivalent whole-genome bisulfite sequencing coverage for obtaining the same number of sequence reads obtained by targeted methylation sequencing.

For further details regarding methylation sequencing (e.g., WGBS and/or targeted methylation sequencing), see, e.g., U.S. patent application Ser. No. 16/352,602, entitled "Anomalous Fragment Detection and Classification," filed Mar. 13, 2019, and U.S. patent application Ser. No. 16/719,902, entitled "Systems and Methods for Estimating Cell Source Fractions Using Methylation Information," filed Dec. 18, 2019, each of which is hereby incorporated by reference. Other methods for methylation sequencing, including those disclosed herein and/or any modifications, substitutions, or combinations thereof, can be used to obtain fragment methylation patterns. A methylation sequencing can be used to identify one or more methylation state vectors, as described, for example, in U.S. patent application Ser. No. 16/352,602, entitled "Anomalous Fragment Detection and Classification," filed Mar. 13, 2019, or in accordance with any of the techniques disclosed in U.S. Provisional Patent Application No. 62/847,223, entitled "Model-Based Featurization and Classification," filed May 13, 2019, now U.S. Provisional patent application Ser. No. 15/931,022, entitled "Model-Based Featurization and Classification," filed May 13, 2020, each of which is hereby incorporated by reference.

The methylation sequencing of nucleic acids and the resulting one or more methylation state vectors can be used to obtain a plurality of nucleic acid methylation fragments. Each corresponding plurality of nucleic acid methylation fragments (e.g., for each respective genotypic dataset) can comprise more than 100 nucleic acid methylation fragments. An average number of nucleic acid methylation fragments across each corresponding plurality of nucleic acid methylation fragments can comprise 1000 or more nucleic acid methylation fragments, 5000 or more nucleic acid methylation fragments, 10,000 or more nucleic acid methylation fragments, 20,000 or more nucleic acid methylation fragments, or 30,000 or more nucleic acid methylation fragments. An average number of nucleic acid methylation fragments across each corresponding plurality of nucleic acid methylation fragments can be between 10,000 nucleic acid methylation fragments and 50,000 nucleic acid methylation fragments. The corresponding plurality of nucleic acid methylation fragments can comprise one thousand or more, ten thousand or more, 100 thousand or more, one million or more, ten million or more, 100 million or more, 500 million or more, one billion or more, two billion or more, three billion or more, four billion or more, five billion or more, six billion or more, seven billion or more, eight billion or more, nine billion or more, or 10 billion or more nucleic acid methylation fragments. An average length of a corresponding plurality of nucleic acid methylation fragments can be between 140 and 280 nucleotides.

Further details regarding methods for sequencing nucleic acids and methylation sequencing data are disclosed in U.S. Patent Application No. 62/985,258, titled "Systems and Methods for Cancer Condition Determination Using Autoencoders," filed Mar. 4, 2020, which is hereby incorporated herein by reference in its entirety.

II.B. Identifying Anomalous Fragments

The analytics system can determine anomalous fragments for a sample using the sample's methylation state vectors. For each fragment in a sample, the analytics system can determine whether the fragment is an anomalous fragment using the methylation state vector corresponding to the fragment. In some embodiments, the analytics system calculates a p-value score for each methylation state vector describing a probability of observing that methylation state vector or other methylation state vectors even less probable in the healthy control group. The process for calculating a p-value score is further discussed below in Section II.B.i. P-Value Filtering. The analytics system may determine fragments with a methylation state vector having below a threshold p-value score as anomalous fragments. In some embodiments, the analytics system further labels fragments with at least some number of CpG sites that have over some threshold percentage of methylation or unmethylation as hypermethylated and hypomethylated fragments, respectively. A hypermethylated fragment or a hypomethylated fragment may also be referred to as an unusual fragment with extreme methylation (UFXM). In some embodiments, the analytics system may implement various other probabilistic models for determining anomalous fragments. Examples of other probabilistic models include a mixture model, a deep probabilistic model, etc. In some embodiments, the analytics system may use any combination of the processes described below for identifying anomalous fragments. With the identified anomalous fragments, the analytics system may filter the set of methylation state vectors for a sample for use in other processes, e.g., for use in training and deploying a cancer classifier.

II.B.i. P-Value Filtering

Figure 2A:
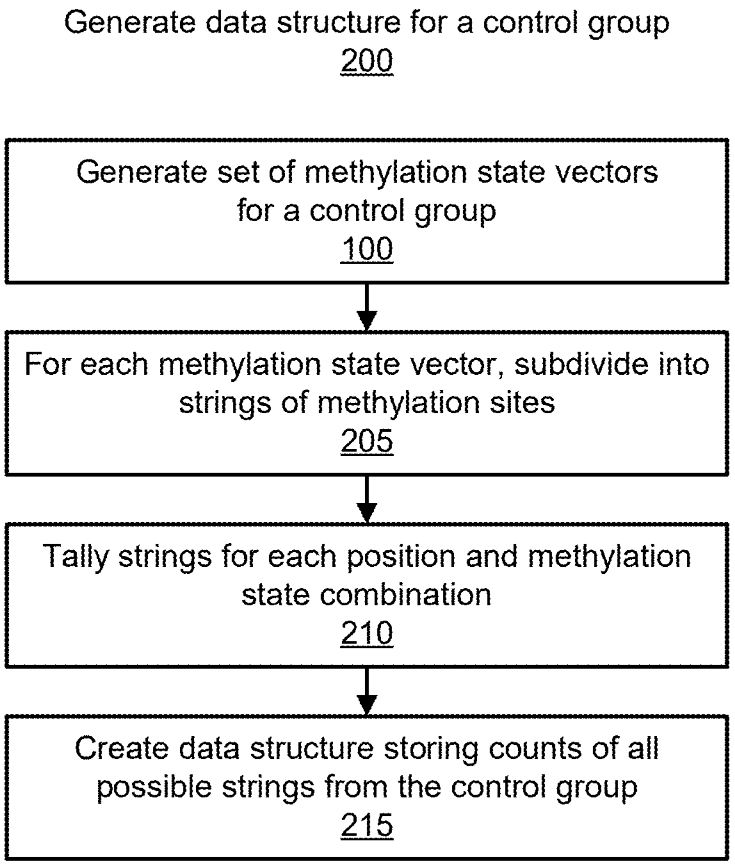
FIGS. 2A & 2B are exemplary flowcharts describing a process of determining anomalously methylated fragments from a sample, according to one or more embodiments.
Figure 2B:
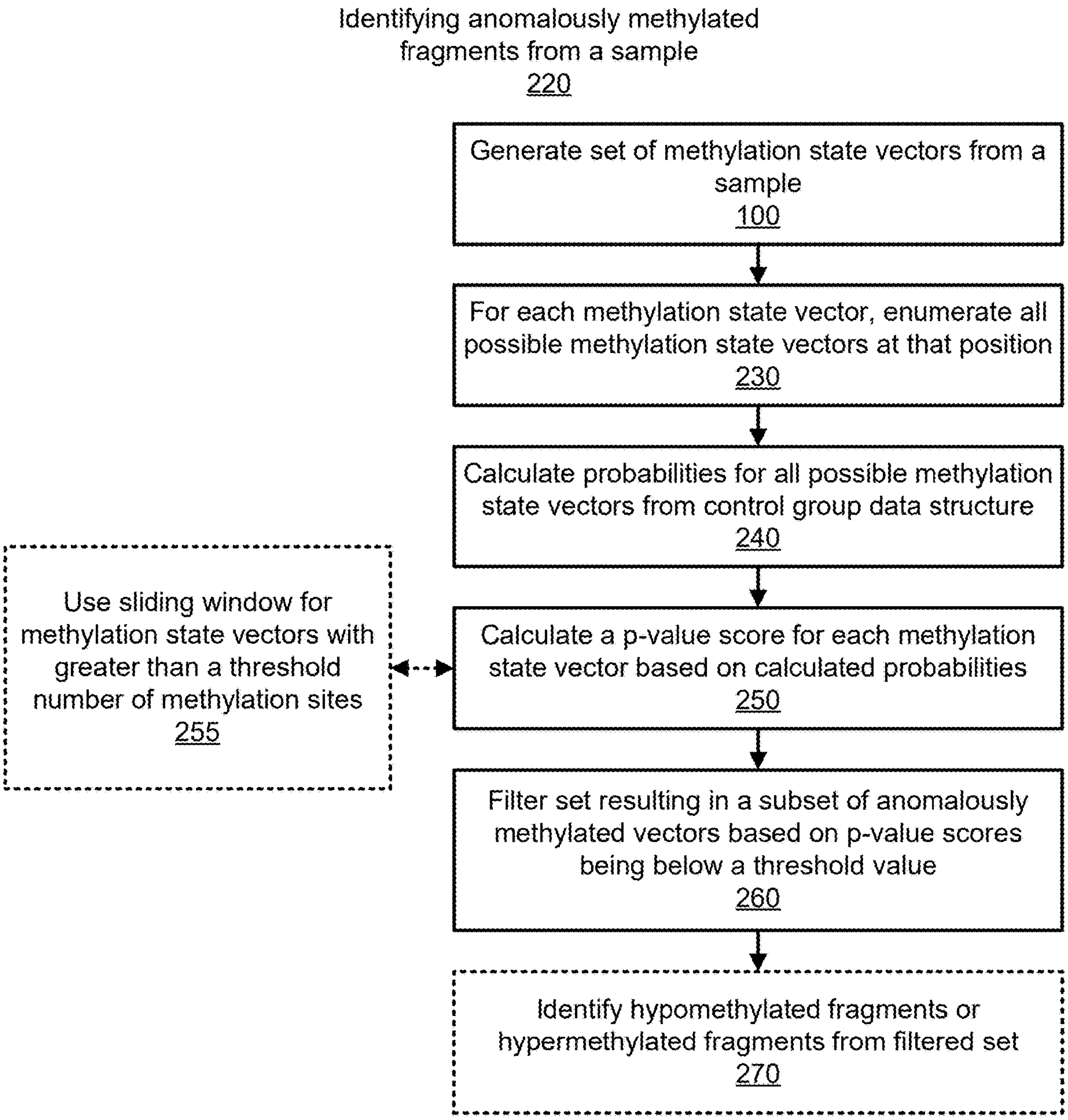

In some embodiments, the analytics system calculates a p-value score for each methylation state vector compared to methylation state vectors from fragments in a healthy control group. The p-value score can describe a probability of observing the methylation status matching that methylation state vector or other methylation state vectors even less probable in the healthy control group. In order to determine a DNA fragment to be anomalously methylated, the analytics system can use a healthy control group with a majority of fragments that are normally methylated. When conducting this probabilistic analysis for determining anomalous fragments, the determination can hold weight in comparison with the group of control subjects that make up the healthy control group. To ensure robustness in the healthy control group, the analytics system may select some threshold number of healthy individuals to source samples including DNA fragments. FIG. 2A describes the method of generating a data structure for a healthy control group with which the analytics system may calculate p-value scores. FIG. 2B describes the method of calculating a p-value score with the generated data structure.

FIG. 2A is a flowchart describing a process 200 of generating a data structure for a healthy control group, according to an embodiment. To create a healthy control group data structure, the analytics system can receive a plurality of DNA fragments (e.g., cfDNA) from a plurality of healthy individuals. A methylation state vector can be identified for each fragment, for example via the process 100.

With each fragment's methylation state vector, the analytics system can subdivide 205 the methylation state vector into strings of CpG sites. In some embodiments, the analytics system subdivides 205 the methylation state vector such that the resulting strings are all less than a given length. For example, a methylation state vector of length 11 may be subdivided into strings of length less than or equal to 3 would result in 9 strings of length 3, 10 strings of length 2, and 11 strings of length 1. In another example, a methylation state vector of length 7 being subdivided into strings of length less than or equal to 4 can result in 4 strings of length 4, 5 strings of length 3, 6 strings of length 2, and 7 strings of length 1. If a methylation state vector is shorter than or the same length as the specified string length, then the methylation state vector may be converted into a single string containing all of the CpG sites of the vector.

The analytics system tallies 210 the strings by counting, for each possible CpG site and possibility of methylation states in the vector, the number of strings present in the control group having the specified CpG site as the first CpG site in the string and having that possibility of methylation states. For example, at a given CpG site and considering string lengths of 3, there are 2^3 or 8 possible string configurations. At that given CpG site, for each of the 8 possible string configurations, the analytics system tallies 210 how many occurrences of each methylation state vector possibility come up in the control group. Continuing this example, this may involve tallying the following quantities: <$M_x$, $M_{x+1}$, $M_{x+2}$>, <$M_x$, $M_{x+1}$, $U_{x+2}$>, . . . , <$U_x$, $U_{x+1}$, $U_{x+2}$> for each starting CpG site x in the reference genome. The analytics system creates 215 the data structure storing the tallied counts for each starting CpG site and string possibility.

There are several benefits to setting an upper limit on string length. First, depending on the maximum length for a string, the size of the data structure created by the analytics system can dramatically increase in size. For instance, maximum string length of 4 means that every CpG site has at the very least 2^4 numbers to tally for strings of length 4. Increasing the maximum string length to 5 means that every CpG site has an additional 2^4 or 16 numbers to tally, doubling the numbers to tally (and computer memory required) compared to the prior string length. Reducing string size can help keep the data structure creation and performance (e.g., use for later accessing as described below), in terms of computational and storage, reasonable. Second, a statistical consideration to limiting the maximum string length can be to avoid overfitting downstream models that use the string counts. If long strings of CpG sites do not, biologically, have a strong effect on the outcome (e.g., predictions of anomalousness that predictive of the presence of cancer), calculating probabilities based on large strings of CpG sites can be problematic as it uses a significant amount of data that may not be available, and thus can be too sparse for a model to perform appropriately. For example, calculating a probability of anomalousness/cancer conditioned on the prior 100 CpG sites can use counts of strings in the data structure of length 100, ideally some matching exactly the prior 100 methylation states. If sparse counts of strings of length 100 are available, there can be insufficient data to determine whether a given string of length of 100 in a test sample is anomalous or not.

FIG. 2B is a flowchart describing a process 220 for identifying anomalously methylated fragments from an individual, according to an embodiment. In process 220, the analytics system generates 100 methylation state vectors from cfDNA fragments of the subject. The analytics system can handle each methylation state vector as follows.

For a given methylation state vector, the analytics system enumerates 230 all possibilities of methylation state vectors having the same starting CpG site and same length (i.e., set of CpG sites) in the methylation state vector. As each methylation state is generally either methylated or unmethylated, there can be effectively two possible states at each CpG site, and thus the count of distinct possibilities of methylation state vectors can depend on a power of 2, such that a methylation state vector of length n would be associated with $2^n$ possibilities of methylation state vectors. With methylation state vectors inclusive of indeterminate states for one or more CpG sites, the analytics system may enumerate 230 possibilities of methylation state vectors considering only CpG sites that have observed states.

The analytics system calculates 240 the probability of observing each possibility of methylation state vector for the identified starting CpG site and methylation state vector length by accessing the healthy control group data structure. In some embodiments, calculating the probability of observing a given possibility uses a Markov chain probability to model the joint probability calculation. The Markov model can be trained, at least in part, based upon evaluation of a methylation state of each CpG site in the corresponding plurality of CpG sites of the respective fragment (e.g., nucleic acid methylation fragment) across those nucleic acid methylation fragments in a healthy noncancer cohort dataset that have the corresponding plurality of CpG sites. For example, a Markov model (e.g., a Hidden Markov Model or HMM) is used to determine the probability that a sequence of methylation states (comprising, e.g., "M" or "U") can be observed for a nucleic acid methylation fragment in a plurality of nucleic acid methylation fragments, given a set of probabilities that determine, for each state in the sequence, the likelihood of observing the next state in the sequence. The set of probabilities can be obtained by training the HMM. Such training can involve computing statistical parameters (e.g., the probability that a first state will transition to a second state (the transition probability) and/or the probability that a given methylation state can be observed for a respective CpG site (the emission probability)), given an initial training dataset of observed methylation state sequences (e.g., methylation patterns). HMMs can be trained using supervised training (e.g., using samples where the underlying sequence as well as the observed states are known) and/or unsupervised training (e.g., Viterbi learning, maximum likelihood estimation, expectation-maximization training, and/or Baum-Welch training). In other embodiments, calculation methods other than Markov chain probabilities are used to determine the probability of observing each possibility of methylation state vector. For example, such calculation method can include a learned representation. The p-value threshold can be between 0.01 and 0.10, or between 0.03 and 0.06. The p-value threshold can be 0.05. The p-value threshold can be less than 0.01, less than 0.001, or less than 0.0001.

The analytics system calculates 250 a p-value score for the methylation state vector using the calculated probabilities for each possibility. In some embodiments, this includes identifying the calculated probability corresponding to the possibility that matches the methylation state vector in question. Specifically, this can be the possibility having the same set of CpG sites, or similarly the same starting CpG site and length as the methylation state vector. The analytics system can sum the calculated probabilities of any possibilities having probabilities less than or equal to the identified probability to generate the p-value score.

This p-value can represent the probability of observing the methylation state vector of the fragment or other methylation state vectors even less probable in the healthy control group. A low p-value score can, thereby, generally correspond to a methylation state vector which is rare in a healthy individual, and which causes the fragment to be labeled anomalously methylated, relative to the healthy control group. A high p-value score can generally relate to a methylation state vector is expected to be present, in a relative sense, in a healthy individual. If the healthy control group is a non-cancerous group, for example, a low p-value can indicate that the fragment is anomalous methylated relative to the non-cancer group, and therefore possibly indicative of the presence of cancer in the test subject.

As above, the analytics system can calculate p-value scores for each of a plurality of methylation state vectors, each representing a cfDNA fragment in the test sample. To identify which of the fragments are anomalously methylated, the analytics system may filter 260 the set of methylation state vectors based on their p-value scores. In some embodiments, filtering is performed by comparing the p-values scores against a threshold and keeping only those fragments below the threshold. This threshold p-value score can be on the order of 0.1, 0.01, 0.001, 0.0001, or similar.

According to example results from the process 220, the analytics system can yield a median (range) of 2,800 (1,500-12,000) fragments with anomalous methylation patterns for participants without cancer in training, and a median (range) of 3,000 (1,200-220,000) fragments with anomalous methylation patterns for participants with cancer in training. These filtered sets of fragments with anomalous methylation patterns may be used for the downstream analyses as described below in Section III.

In some embodiments, the analytics system uses 255 a sliding window to determine possibilities of methylation state vectors and calculate p-values. Rather than enumerating possibilities and calculating p-values for entire methylation state vectors, the analytics system can enumerate possibilities and calculates p-values for only a window of sequential CpG sites, where the window is shorter in length (of CpG sites) than at least some fragments (otherwise, the window would serve no purpose). The window length may be static, user determined, dynamic, or otherwise selected.

In calculating p-values for a methylation state vector larger than the window, the window can identify the sequential set of CpG sites from the vector within the window starting from the first CpG site in the vector. The analytic system can calculate a p-value score for the window including the first CpG site. The analytics system can then "slide" the window to the second CpG site in the vector, and calculate another p-value score for the second window. Thus, for a window size l and methylation vector length m, each methylation state vector can generate m−l+1 p-value scores. After completing the p-value calculations for each portion of the vector, the lowest p-value score from all sliding windows can be taken as the overall p-value score for the methylation state vector. In some embodiments, the analytics system aggregates the p-value scores for the methylation state vectors to generate an overall p-value score.

Using the sliding window can help to reduce the number of enumerated possibilities of methylation state vectors and their corresponding probability calculations that would otherwise need to be performed. To give a realistic example, it can be possible for fragments to have upwards of 54 CpG sites. Instead of computing probabilities for 2ˆ54 (~1.8×10ˆ16) possibilities to generate a single p-score, the analytics system can instead use a window of size 5 (for example) which results in 50 p-value calculations for each of the 50 windows of the methylation state vector for that fragment. Each of the 50 calculations can enumerate 2ˆ5 (32) possibilities of methylation state vectors, which total results in 50×2ˆ5 (1.6×10ˆ3) probability calculations. This can result in a vast reduction of calculations to be performed, with no meaningful hit to the accurate identification of anomalous fragments.

In embodiments with indeterminate states, the analytics system may calculate a p-value score summing out CpG sites with indeterminates states in a fragment's methylation state vector. The analytics system can identify all possibilities that have consensus with the all methylation states of the methylation state vector excluding the indeterminate states. The analytics system may assign the probability to the methylation state vector as a sum of the probabilities of the identified possibilities. As an example, the analytics system can calculate a probability of a methylation state vector of $<M_1, I_2, U_3>$ as a sum of the probabilities for the possibilities of methylation state vectors of $<M_1, M_2, U_3>$ and $<M_1, U_2, U_3>$ since methylation states for CpG sites 1 and 3 are observed and in consensus with the fragment's methylation states at CpG sites 1 and 3. This method of summing out CpG sites with indeterminate states can use calculations of probabilities of possibilities up to 2ˆi, wherein i denotes the number of indeterminate states in the methylation state vector. In additional embodiments, a dynamic programming algorithm may be implemented to calculate the probability of a methylation state vector with one or more indeterminate states. Advantageously, the dynamic programming algorithm can operate in linear computational time.

In some embodiments, the computational burden of calculating probabilities and/or p-value scores may be further reduced by caching at least some calculations. For example, the analytic system may cache in transitory or persistent memory calculations of probabilities for possibilities of methylation state vectors (or windows thereof). If other fragments have the same CpG sites, caching the possibility probabilities can allow for efficient calculation of p-score values without needing to re-calculate the underlying possibility probabilities. Equivalently, the analytics system may calculate p-value scores for each of the possibilities of methylation state vectors associated with a set of CpG sites from vector (or window thereof). The analytics system may cache the p-value scores for use in determining the p-value scores of other fragments including the same CpG sites. Generally, the p-value scores of possibilities of methylation state vectors having the same CpG sites may be used to determine the p-value score of a different one of the possibilities from the same set of CpG sites.

One or more nucleic acid methylation fragments can be filtered prior to training region models or cancer classifier. Filtering nucleic acid methylation fragments can comprise removing, from the corresponding plurality of nucleic acid methylation fragments, each respective nucleic acid methylation fragment that fails to satisfy one or more selection criteria (e.g., below or above one selection criteria). The one or more selection criteria can comprise a p-value threshold. The output p-value of the respective nucleic acid methylation fragment can be determined, at least in part, based upon a comparison of the corresponding methylation pattern of the respective nucleic acid methylation fragment to a corresponding distribution of methylation patterns of those nucleic acid methylation fragments in a healthy noncancer cohort dataset that have the corresponding plurality of CpG sites of the respective nucleic acid methylation fragment.

Filtering a plurality of nucleic acid methylation fragments can comprise removing each respective nucleic acid methylation fragment that fails to satisfy a p-value threshold. The filter can be applied to the methylation pattern of each respective nucleic acid methylation fragment using the methylation patterns observed across the first plurality of nucleic acid methylation fragments. Each respective methylation pattern of each respective nucleic acid methylation fragment (e.g., Fragment One, . . . , Fragment N) can comprise a corresponding one or more methylation sites (e.g., CpG sites) identified with a methylation site identifier and a corresponding methylation pattern, represented as a sequence of 1's and 0's, where each "1" represents a methylated CpG site in the one or more CpG sites and each "0" represents an unmethylated CpG site in the one or more CpG sites. The methylation patterns observed across the first plurality of nucleic acid methylation fragments can be used to build a methylation state distribution for the CpG site states collectively represented by the first plurality of nucleic acid methylation fragments (e.g., CpG site A, CpG site B, . . . , CpG site ZZZ). Further details regarding processing of nucleic acid methylation fragments are disclosed in U.S. Patent Application No. 62/985,258, titled "Systems and Methods for Cancer Condition Determination Using Autoencoders," filed Mar. 4, 2020, which is hereby incorporated herein by reference in its entirety.

The respective nucleic acid methylation fragment may fail to satisfy a selection criterion in the one or more selection criteria when the respective nucleic acid methylation fragment has an anomalous methylation score that is less than an anomalous methylation score threshold. In this situation, the anomalous methylation score can be determined by a mixture model. For example, a mixture model can detect an anomalous methylation pattern in a nucleic acid methylation fragment by determining the likelihood of a methylation state vector (e.g., a methylation pattern) for the respective nucleic acid methylation fragment based on the number of possible methylation state vectors of the same length and at the same corresponding genomic location. This can be executed by generating a plurality of possible methylation states for vectors of a specified length at each genomic location in a reference genome. Using the plurality of possible methylation states, the number of total possible methylation states and subsequently the probability of each predicted methylation state at the genomic location can be determined. The likelihood of a sample nucleic acid methylation fragment corresponding to a genomic location within the reference genome can then be determined by matching the sample nucleic acid methylation fragment to a predicted (e.g., possible) methylation state and retrieving the calculated probability of the predicted methylation state. An anomalous methylation score can then be calculated based on the probability of the sample nucleic acid methylation fragment.

The respective nucleic acid methylation fragment can fail to satisfy a selection criterion in the one or more selection criteria when the respective nucleic acid methylation fragment has less than a threshold number of residues. The threshold number of residues can be between 10 and 50, between 50 and 100, between 100 and 150, or more than 150. The threshold number of residues can be a fixed value between 20 and 90. The respective nucleic acid methylation fragment may fail to satisfy a selection criterion in the one or more selection criteria when the respective nucleic acid methylation fragment has less than a threshold number of CpG sites. The threshold number of CpG sites can be 4, 5, 6, 7, 8, 9, or 10. The respective nucleic acid methylation fragment can fail to satisfy a selection criterion in the one or more selection criteria when a genomic start position and a genomic end position of the respective nucleic acid methylation fragment indicates that the respective nucleic acid methylation fragment represents less than a threshold number of nucleotides in a human genome reference sequence.

The filtering can remove a nucleic acid methylation fragment in the corresponding plurality of nucleic acid methylation fragments that has the same corresponding methylation pattern and the same corresponding genomic start position and genomic end position as another nucleic acid methylation fragment in the corresponding plurality of nucleic acid methylation fragments. This filtering step can remove redundant fragments that are exact duplicates, including, in some instances, PCR duplicates. The filtering can remove a nucleic acid methylation fragment that has the same corresponding genomic start position and genomic end position and less than a threshold number of different methylation states as another nucleic acid methylation fragment in the corresponding plurality of nucleic acid methylation fragments. The threshold number of different methylation states used for retention of a nucleic acid methylation fragment can be 1, 2, 3, 4, 5, or more than 5. For example, a first nucleic acid methylation fragment having the same corresponding genomic start and end position as a second nucleic acid methylation fragment but having at least 1, at least 2, at least 3, at least 4, or at least 5 different methylation states at a respective CpG site (e.g., aligned to a reference genome) is retained. As another example, a first nucleic acid methylation fragment having the same methylation state vector (e.g., methylation pattern) but different corresponding genomic start and end positions as a second nucleic acid methylation fragment is also retained.

The filtering can remove assay artifacts in the plurality of nucleic acid methylation fragments. The removal of assay artifacts can comprise removing sequence reads obtained from sequenced hybridization probes and/or sequence reads obtained from sequences that failed to undergo conversion during bisulfite conversion. The filtering can remove contaminants (e.g., due to sequencing, nucleic acid isolation, and/or sample preparation).

The filtering can remove a subset of methylation fragments from the plurality of methylation fragments based on mutual information filtering of the respective methylation fragments against the cancer state across the plurality of training subjects. For example, mutual information can provide a measure of the mutual dependence between two conditions of interest sampled simultaneously. Mutual information can be determined by selecting an independent set of CpG sites (e.g., within all or a portion of a nucleic acid methylation fragment) from one or more datasets and comparing the probability of the methylation states for the set of CpG sites between two sample groups (e.g., subsets and/or groups of genotypic datasets, biological samples, and/or subjects). A mutual information score can denote the probability of the methylation pattern for a first condition versus a second condition at the respective region in the respective frame of the sliding window, thus indicating the discriminative power of the respective region. A mutual information score can be similarly calculated for each region in each frame of the sliding window as it progresses across the selected sets of CpG sites and/or the selected genomic regions. Further details regarding mutual information filtering are disclosed in U.S. Provisional Patent Application 62/948,129, titled "Cancer Classification using Patch Convolutional Neural Networks," filed Dec. 13, 2019, which is hereby incorporated herein by reference in its entirety.

II.B.ii. Hypermethylated Fragments and Hypomethylated Fragments

In some embodiments, the analytics system determines anomalous fragments as fragments with over a threshold number of CpG sites and either with over a threshold percentage of the CpG sites methylated or with over a threshold percentage of CpG sites unmethylated; the analytics system identifies such fragments as hypermethylated fragments or hypomethylated fragments. Example thresholds for length of fragments (or CpG sites) include more than 3, 4, 5, 6, 7, 8, 9, 10, etc. Example percentage thresholds of methylation or unmethylation include more than 80%, 85%, 90%, or 95%, or any other percentage within the range of 50%-100%.

II.C. Example Analytics System

Figure 9A:
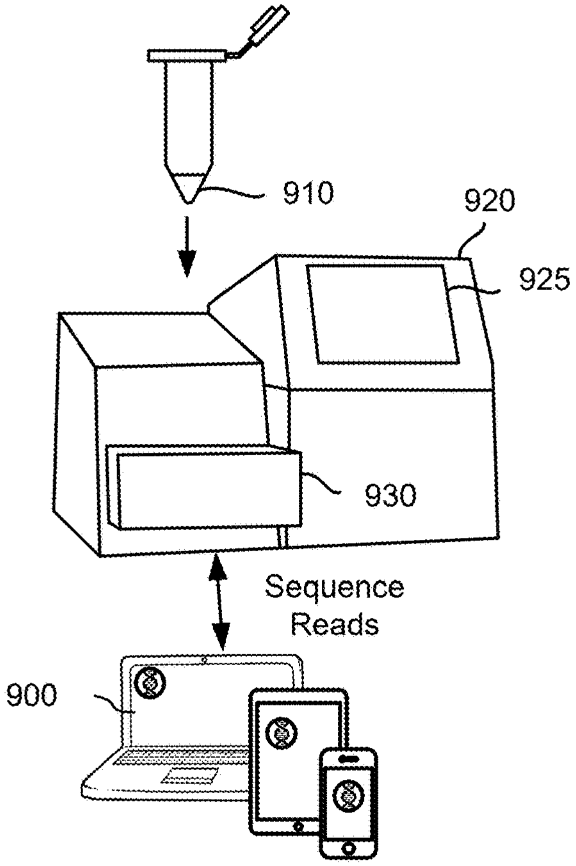
FIG. 9A is an exemplary flowchart of devices for sequencing nucleic acid samples according to one or more embodiments.

FIG. 9A is a flowchart of devices for sequencing nucleic acid samples according to one embodiment. This illustrative flowchart includes devices such as a sequencer 920 and an analytics system 900. The sequencer 920 and the analytics system 900 may work in tandem to perform one or more steps in any of the process described herein this disclosure.

In various embodiments, the sequencer 920 receives an enriched nucleic acid sample 910. As shown in FIG. 9A, the sequencer 920 can include a graphical user interface 925 that enables user interactions with particular tasks (e.g., initiate sequencing or terminate sequencing) as well as one more loading stations 930 for loading a sequencing cartridge including the enriched fragment samples and/or for loading necessary buffers for performing the sequencing assays. Therefore, once a user of the sequencer 920 has provided the necessary reagents and sequencing cartridge to the loading station 930 of the sequencer 920, the user can initiate sequencing by interacting with the graphical user interface 925 of the sequencer 920. Once initiated, the sequencer 920 performs the sequencing and outputs the sequence reads of the enriched fragments from the nucleic acid sample 910.

In some embodiments, the sequencer 920 is communicatively coupled with the analytics system 900. The analytics system 900 includes some number of computing devices used for processing the sequence reads for various applications such as assessing methylation status at one or more CpG sites, variant calling or quality control. The sequencer 920 may provide the sequence reads in a BAM file format to the analytics system 900. The analytics system 900 can be communicatively coupled to the sequencer 920 through a wireless, wired, or a combination of wireless and wired communication technologies. Generally, the analytics system 900 is configured with a processor and non-transitory computer-readable storage medium storing computer instructions that, when executed by the processor, cause the processor to process the sequence reads or to perform one or more steps of any of the methods or processes disclosed herein.

In some embodiments, the sequence reads may be aligned to a reference genome to determine alignment position information, e.g., via step 140 of the process 100 in FIG. 1A. Alignment position may generally describe a beginning position and an end position of a region in the reference genome that corresponds to a beginning nucleotide based and an end nucleotide base of a given sequence read. Corresponding to methylation sequencing, the alignment position information may be generalized to indicate a first CpG site and a last CpG site included in the sequence read according to the alignment to the reference genome. The alignment position information may further indicate methylation statuses and locations of all CpG sites in a given sequence read. A region in the reference genome may be associated with a gene or a segment of a gene; as such, the analytics system 900 may label a sequence read with one or more genes that align to the sequence read. In one embodiment, fragment length (or size) is be determined from the beginning and end positions.

In various embodiments, for example when a paired-end sequencing process is used, a sequence read is comprised of a read pair denoted as R_1 and R_2. For example, the first read R_1 may be sequenced from a first end of a double-stranded DNA (dsDNA) molecule whereas the second read R_2 may be sequenced from the second end of the double-stranded DNA (dsDNA). Therefore, nucleotide base pairs of the first read R_1 and second read R_2 may be aligned consistently (e.g., in opposite orientations) with nucleotide bases of the reference genome. Alignment position information derived from the read pair R_1 and R_2 may include a beginning position in the reference genome that corresponds to an end of a first read (e.g., R_1) and an end position in the reference genome that corresponds to an end of a second read (e.g., R_2). In other words, the beginning position and end position in the reference genome can represent the likely location within the reference genome to which the nucleic acid fragment corresponds. An output file having SAM (sequence alignment map) format or BAM (binary) format may be generated and output for further analysis.

Figure 9B:
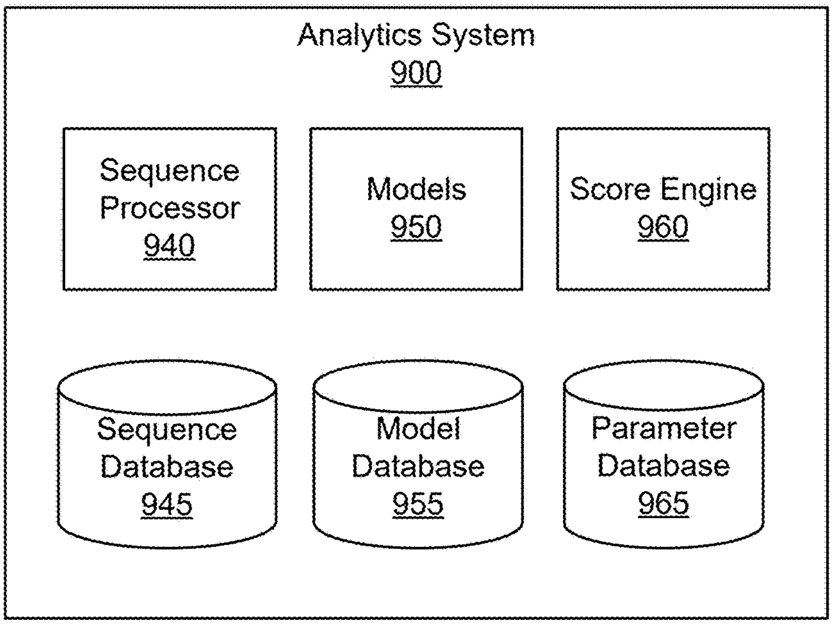
FIG. 9B is an exemplary block diagram of an analytics system, according to one or more embodiments.

Referring now to FIG. 9B, FIG. 9B is a block diagram of an analytics system 900 for processing DNA samples according to one embodiment. The analytics system implements one or more computing devices for use in analyzing DNA samples. The analytics system 900 includes a sequence processor 940, sequence database 945, model database 955, models 950, parameter database 965, and score engine 960. In some embodiments, the analytics system 900 performs some or all of the processes 100 of FIG. 1A and 200 of FIG. 2.

The sequence processor 940 generates methylation state vectors for fragments from a sample. At each CpG site on a fragment, the sequence processor 940 generates a methylation state vector for each fragment specifying a location of the fragment in the reference genome, a number of CpG sites in the fragment, and the methylation state of each CpG site in the fragment whether methylated, unmethylated, or indeterminate via the process 100 of FIG. 1A. The sequence processor 940 may store methylation state vectors for fragments in the sequence database 945. Data in the sequence database 945 may be organized such that the methylation state vectors from a sample are associated to one another.

Further, multiple different models 950 may be stored in the model database 955 or retrieved for use with test samples. In one example, a model is a trained cancer classifier for determining a cancer prediction for a test sample using a feature vector derived from anomalous fragments. The training and use of the cancer classifier will be further discussed in conjunction with Section III. Cancer Classifier for Determining Cancer. The analytics system 900 may train the one or more models 950 and store various trained parameters in the parameter database 965. The analytics system 900 stores the models 950 along with functions in the model database 955.

During inference, the score engine 960 uses the one or more models 950 to return outputs. The score engine 960 accesses the models 950 in the model database 955 along with trained parameters from the parameter database 965. According to each model, the score engine receives an appropriate input for the model and calculates an output based on the received input, the parameters, and a function of each model relating the input and the output. In some use cases, the score engine 960 further calculates metrics correlating to a confidence in the calculated outputs from the model. In other use cases, the score engine 960 calculates other intermediary values for use in the model.

III. Cancer Classification with Genomic Region Modeling

III.A. Overview

Cancer classification can be a process that determines a cancer prediction for a particular test sample based on DNA fragments in the test sample. The cancer prediction may be a binary prediction between cancer and non-cancer and/or a multiclass prediction between a plurality of cancer types. For example, the binary prediction may be a label of cancer or non-cancer or a likelihood of cancer. As an example, the multiclass prediction may provide a likelihood for each of a plurality of cancer types, or may provide one or more cancer types associated with above-threshold or greatest likelihoods.

Figure 3:
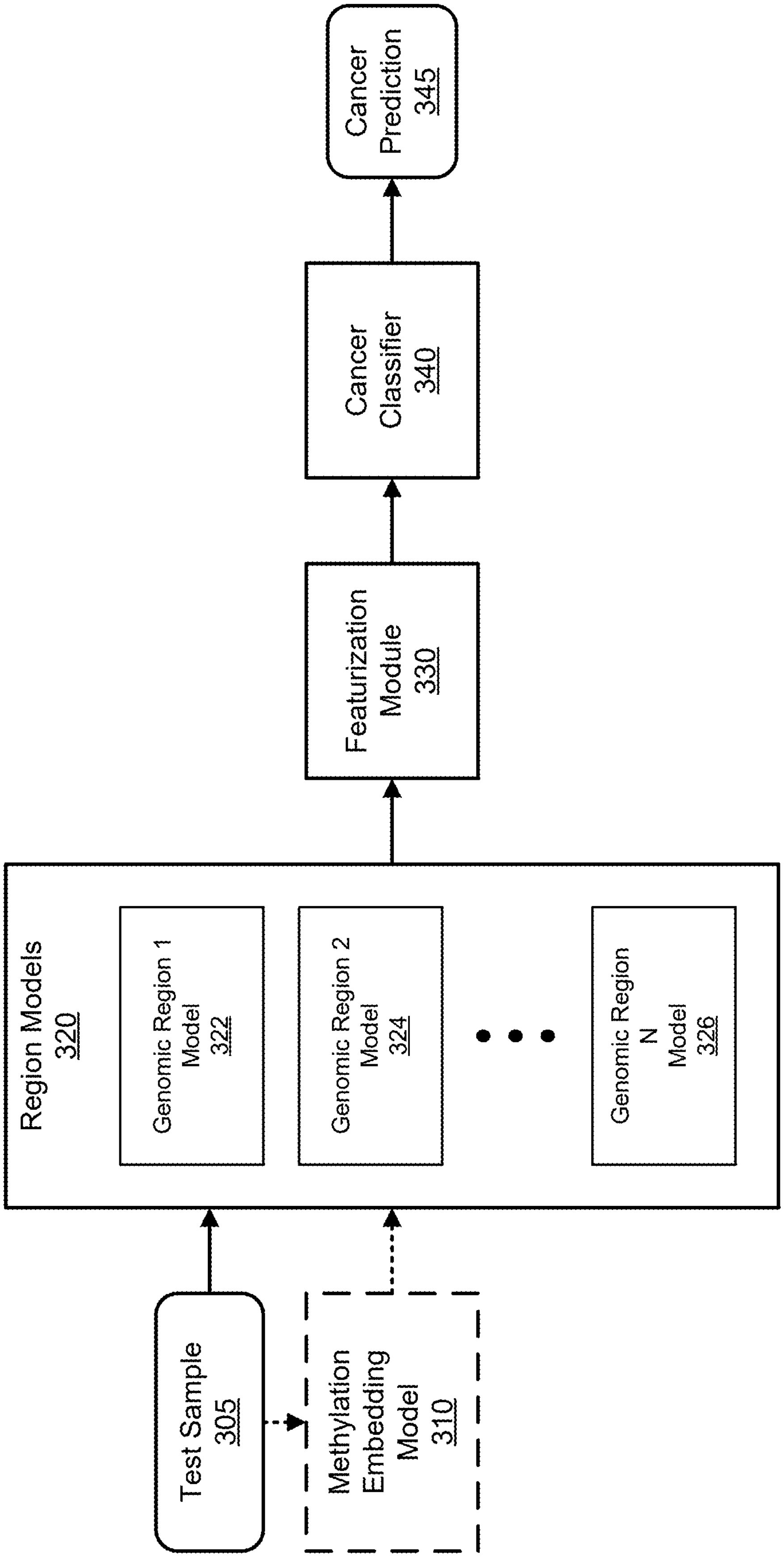
FIG. 3 is an exemplary flowchart of a cancer classification process, according to one or more embodiments.

FIG. 3 illustrates the cancer classification process. A test sample 305 comprises a plurality of DNA fragments (e.g., methylation fragments). The DNA fragments may be determined to be anomalous fragments via the process 220 in FIG. 2B, or more specifically hypermethylated and hypomethylated fragments as determined via the step 270 of the process 220. The DNA fragments may be input into a methylation embedding model 310 that outputs a methylation embedding for each DNA fragment. The DNA fragments (or the methylation embedding for each DNA fragment) can be provided to a plurality of region models 320 which includes a region model trained for each genomic region targeted by the assay. Each region model can be configured to input DNA fragments in a genomic region or the methylation embeddings of such fragments. For example, DNA fragments in Genomic Region 1 are input into Genomic Region 1 model 322, DNA fragments in Genomic Region 2 are input into Genomic Region 2 model 324, . . . , DNA fragments in Genomic Region N are input into Genomic Region N model 326. Each genomic region model may output a cancer score or a region embedding for an input DNA fragment. A featurization module 330 generates a test feature vector for the test sample 305 based on the outputs of the region models 320. Size of each genomic region and the total number of genomic regions may be adjusted to optimize classification performance. In some embodiments, there are at least 1,000, at least 2,000, at least 3,000, at least 4,000, at least 5,000, at least 6,000, at least 7,000, at least 8,000, at least 9,000, at least 10,000 genomic regions, at least 20,000 genomic regions, at least 30,000 genomic region, at least 40,000 genomic regions, at least 50,000 genomic regions, at least 60,000 genomic regions, at least 70,000 genomic regions, at least 80,000 genomic regions, or at least 100,000 genomic regions. In some embodiments, each genomic region is no greater than 50, no greater than 60, no greater than 70, no greater than 80, no greater than 90, or no greater than 100 CpG sites. In some such embodiments, each genomic region in the plurality of regions comprises at least 1, at least 2, at least 3, at least 4, at least 5, at least 6, at least 7, at least 8, at least 9, at least 10, at least 20, at least 30, or more than 30 CpG sites. In some embodiments, each genomic region comprises one or more contiguous CpG sites. Genomic regions can be selected based on the proximity of CpG sites within a genomic region. For example, genomic regions are selected based on a threshold density of CpG sites within a genomic region of a predetermined length.

There may be more than 10,000 CpG sites, more than 25,000 CpG sites, more than 50,000 CpG sites, more than 100,000 CpG sites, more than 250,000 CpG sites, more than 500,000 CpG sites, more than 1,000,000 CpG sites, more than 2,000,000 CpG sites, more than 3,000,000 CpG sites, or more than 5,000,000 CpG sites across the plurality of genomic regions. A first genomic region and a second genomic region can comprise the same number of CpG sites. In some alternative embodiments, a first genomic region can comprise a first number of CpG sites and a second genomic region can comprise a second number of CpG sites that are different than the first number of CpG sites.

Each genomic region can be selected from a portion of a reference genome (e.g., a human reference genome). Each genomic region can represent between 500 base pairs and 10,000 base pairs of a human genome reference sequence. Each genomic region in the plurality of genomic regions can represent between 500 base pairs and 2,000 base pairs of a human genome reference sequence. Each genomic region in the plurality of genomic regions can comprise 1000 base pairs. A first genomic region can be a first length in base pairs and a second genomic region can be a second length in base pairs that is different from the first length in base pairs. In some embodiments, each genomic region in the plurality of genomic regions can be the same length in base pairs. Each genomic region in the plurality of genomic regions can represent a different portion of a human genome reference sequence. Each genomic in the plurality of genomic regions can correspond to all or a portion of a target in a targeted methylation sequencing panel. Each genomic region in the plurality of genomic regions can correspond to one target in a targeted methylation sequencing panel. Furthermore, a target in a targeted methylation sequencing panel can comprise one or more genomic regions.

One or more nucleic acid methylation fragments can align to (e.g., maps to) a genomic region. The number of nucleic acid methylation fragments that aligns to a genomic region is at least 5, at least 10, at least 20, at least 30, at least 40, at least 50, at least 60, at least 70, at least 80, at least 90, at least 100, at least 150, at least 200, at least 500, at least 1000, at least 2000, at least 5000, at least 10,000, at least 100,000, at least one million, or more. Each plurality of nucleic acid methylation fragments can comprise nucleic acid methylation fragments spanning all or a portion of a reference genome, such that subsets of each plurality of nucleic acid methylation fragments can be binned into one or more genomic regions representing a corresponding one or more portions of a reference genome. Likewise, one or more subsets of nucleic acid methylation fragments can be binned into a single genomic region, where each subset of nucleic acid methylation fragments corresponds to a respective genotypic dataset corresponding to a respective training subject. A nucleic acid methylation fragment can be binned into a genomic region if the sequence of the nucleic acid methylation fragment is wholly contained within the sequence spanned by the genomic region. In some alternative embodiments, a nucleic acid methylation fragment is binned into a genomic region if at least a threshold proportion of the sequence of the nucleic acid methylation fragment is contained within the sequence spanned by the genomic region. In some embodiments, a nucleic acid methylation fragment is binned into a genomic region if the sequence spanned by the genomic region is larger than the length of the nucleic acid methylation fragment.

The cancer classifier 340 is configured to input the test feature vector and return a cancer prediction 345. The cancer prediction may be a binary prediction between presence and absence of cancer or a multiclass prediction between a plurality of cancer types. The cancer classifier 340 comprises a plurality of classification parameters and a function representing a relation between the feature vector as input and the cancer prediction as output determined by the function operating on the input feature vector with the classification parameters.

Prior to deployment, the methylation embedding model 310, the region models 320, the featurization module 330, the cancer classifier 340, or any combination thereof can be trained.

III.B. Training

The analytics system can train the methylation embedding model 310, the region models 320, the featurization module 330, the cancer classifier 340, or any combination thereof with a plurality of training samples each having a set of anomalous fragments and a label of a cancer type. The plurality of training samples can include any combination of samples from healthy individuals with a general label of "non-cancer," samples from subjects with a general label of "cancer" or a specific label (e.g., "breast cancer," "lung cancer," etc.). The training samples from subjects for one cancer type may be termed a cohort for that cancer type or a cancer type cohort.

The methylation embedding model 310, the region models 320, the featurization module 330, and the cancer classifier 340 may be trained independently or concurrently with other components. Components of the cancer classification process include any model described in FIG. 3, including the methylation embedding model 310, the region models 320, the featurization module 330, and the cancer classifier 340. Independently training a component of the cancer classification process can refer to adjusting weights of a first component without adjusting weights of a second component while feeding training data through the first component. Training components independently permits training of the components synchronously, or at the same time independent of the other. Concurrently training two components refers to adjusting weights of the two components whilst feeding training data through both components. For example, when training all the various components concurrently, the analytics system feeds training samples through each component (i.e., from start to finish) and adjusts weights of each component to minimize a loss function between the known labels for the training samples and the predicted labels for the training samples. The analytics system may implement iterative batch training which subdivides the training samples into batches to pass through the components. The number of epochs used in training can be the number of passes of each training sample through the components.

III.B.i Methylation Embedding Module

The methylation embedding model 310 is trained to generate a methylation embedding for an input DNA fragment. A methylation embedding can be a mathematical vector that captures the methylation signature of a DNA fragment. The DNA fragment or its methylation state vector can describe at least a methylation status of each CpG site covered by the DNA fragment. Generally, the methylation embedding model 310 can reduce dimensionality of the fragment space into an embedding space. For example, the fragment space may span over a million CpG sites, while the embedding space may span up to 100 dimensions. The methylation embedding model 310 can be capable of projecting all fragments in the fragment space into the embedding space. Some approaches can include Principal Component Analysis (PCA), t-distributed stochastic neighbor embedding, autoencoder, linear discriminant analysis, other dimensionality reduction techniques, or other embedding techniques. The methylation embedding model may implement machine-learning algorithms, such as a neural network algorithm, a support vector machine algorithm, a decision tree algorithm, a multinomial logistic regression algorithm, a linear regression algorithm, or some other machine learning algorithm. The methylation embedding model 310 may be trained independently or concurrently with other components.

In autoencoding embodiments, the methylation embedding model 310 has an encoder configured to project the input DNA fragment (or its methylation state vector) into a methylation embedding and a decoder configured to decode the DNA fragment (or its methylation state vector) from the methylation embedding. The encoder and decoder can be concurrently trained by inputting DNA fragments (or their methylation state vectors) through the encoder and decoder and adjusting weights to minimize a loss function between the decoded fragment and the original input fragment (or the decoded methylation state vector and the original input methylation state vector). Once sufficiently trained, e.g., insuring loss below a threshold, the encoder can serve as the methylation embedding model 310 configured to generate a methylation embedding for an input DNA fragment (or its methylation state vector).

Benefits of the methylation embedding model 310 include shared weights over the genomic regions. As the methylation embedding model 310 can project fragments from all the genomic regions spanning across the entire fragment space, weights and parameters of the methylation embedding model 310 are shared over the genomic regions. For example, a fragment in one genomic region and a fragment in another genomic region are fed through the same methylation embedding model 310 which generates a methylation embedding for each fragment with the same weights and parameters of the methylation embedding model 310. The methylation embedding model 310 can retain information across the genomic regions given the weights shared across the genomic regions. When training the methylation embedding model 310 independently, there can be the added benefit of being able to save on training time given the ability to train components concurrently.

III.B.ii Region Models

A genomic region model can be trained for each genomic region. The genomic region model can input a DNA fragment or a methylation embedding thereof and output a cancer score or a region embedding that are used in generating a feature vector for classification. Each genomic region model may implement a neural network algorithm, a support vector machine algorithm, a decision tree algorithm, a multinomial logistic regression algorithm, a linear regression algorithm, or some other machine learning algorithm.

In some embodiments where each genomic region model implements a neural network algorithm, each genomic region comprises no more than one hidden layer, no more than two hidden layers, or no more than three hidden layers. Each hidden layer may have no more than 8 nodes (or units, neurons), no more than 9 nodes, no more than 10 nodes, no more than 11 nodes, no more than 12 nodes, no more than 16 nodes, no more than 20 nodes, no more than 24 nodes, no more than 28 nodes, or no more than 32 nodes. Architectures of genomic regions may differ. For example, a first genomic region model may have a different number of hidden layers as a second genomic region. In another example, a third genomic region model may have a different number of nodes in its hidden layer than a fourth genomic region model. The region models may be trained independently from one another or concurrently.

Figure 4A:
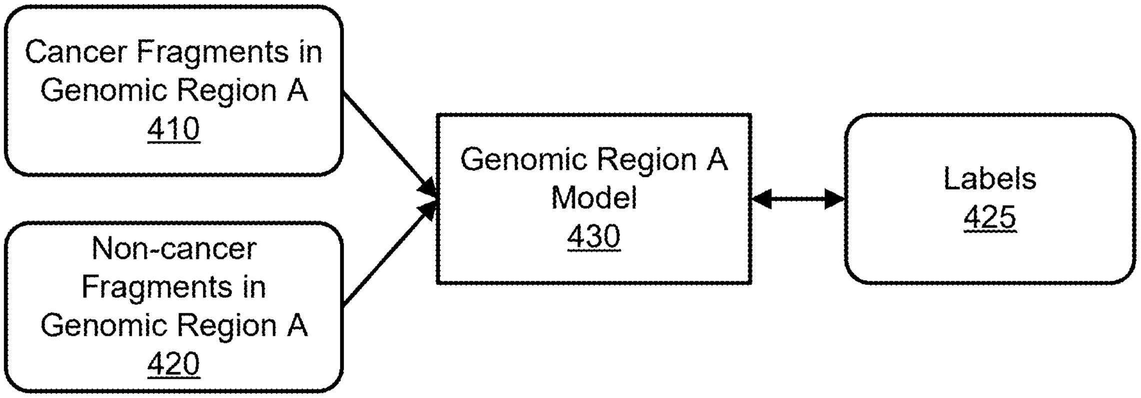
FIG. 4A is an exemplary flowchart describing a process of independently training a genomic region model, according to one or more embodiments.

FIG. 4A is an exemplary flowchart describing a process of independently training a genomic region model, according to one or more embodiments. The analytics system can identify fragments in Genomic Region A from training samples. Cancer fragments 410 in Genomic Region A are taken from cancer training samples and assigned a label of cancer. Non-cancer fragments 420 in Genomic Region A are taken from non-cancer training samples and assigned a label of non-cancer. The analytics system feeds the cancer fragments 410 and the non-cancer fragments through the Genomic Region A model 430 and adjust weights to minimize a loss function between the known labels 425 and predicted labels by the Genomic Region A model 430.

In another embodiment, a genomic region model may be trained with a fragment classifier. In such an embodiment, the genomic region model is configured to output a region embedding. Fragments or their methylation embeddings are fed through the genomic region model which outputs a region embedding that is fed into a fragment classifier that outputs a label of cancer. The analytics system trains the genomic region model and the fragment classifier by adjusting weights of the genomic region model and the fragment classifier to minimize a loss function between the known labels of the fragments and the predicted labels of the fragment. During deployment, the trained genomic region model is configured to input a fragment or its methylation embedding and to output a region embedding.

Training the genomic region models independently can be advantageous in that each genomic region model, being of a relatively small size, can be quickly trained and trained concurrently as each genomic region model is independent from the others. These advantages can translate to decreased expenses for computing resources and faster training times.

Figure 4B:
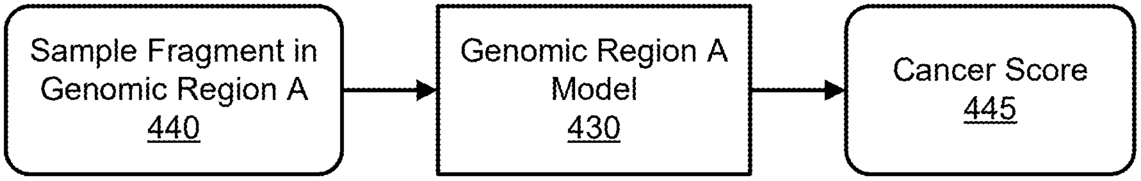
FIG. 4B is an exemplary flowchart describing a process of deploying a genomic region model, according to one or more embodiments.

FIG. 4B is an exemplary flowchart describing a process of deploying a genomic region model, according to an embodiment. A sample fragment 440 in Genomic Region A is input into the Genomic Region A model 430, and the Genomic Region A model 430 outputs a cancer score 445. The cancer score 445 may be a binary prediction between cancer and non-cancer, i.e., a likelihood that the sample fragment 440 was derived from an individual with cancer. The cancer score 445 may, alternatively, be a multiclass prediction between a plurality of cancer types, i.e., a likelihood that the sample fragment 440 was derived from an individual of each cancer type (e.g., 70% likelihood from an individual with breast cancer, 20% likelihood from an individual with colorectal cancer, 10% likelihood from an individual absent cancer). The genomic region model can output any prediction, such as a probability of a condition of interest. If the genomic region model is a single-class classification model, the output can be a likelihood of an input dataset (e.g., of a biological sample and/or subject) having a condition (e.g., a label or class). If the genomic region model is a multi-class classification model, multiple prediction values can be generated, with each prediction value indicating the likelihood of an input dataset for each condition of interest.

The genomic region model (e.g., a neural network) can comprise a corresponding plurality of weights. The genomic region model can score nucleic acid methylation fragments that map to the respective genomic region thereby obtaining a corresponding plurality of training scores. The training can update a corresponding value of each weight in the corresponding plurality of weights in the genomic region model based on a comparison of the corresponding plurality of training scores to the corresponding label for the cancer state of the training subjects originating the nucleic acid methylation fragments.

Each genomic region model can comprise a corresponding plurality of inputs, where each input is for a methylation state in the genomic region. Each genomic region model can further comprise a corresponding first hidden layer comprising a corresponding plurality of hidden neurons, where each hidden neuron in the corresponding plurality of hidden neurons (i) is fully connected to each input in the plurality of inputs, (ii) is associated with a first activation function type, and (iii) is associated with a weight for the genomic region model. Each genomic region model can further comprise one or more corresponding outputs, where each respective output (i) directly or indirectly receives, as input, an output of each hidden neuron in the corresponding plurality of hidden neurons, and (ii) is associated with a second activation function type.

Each hidden unit can be associated with an activation function that performs a function on the input data (e.g., a linear or non-linear function). The activation function can introduce nonlinearity into the data such that the neural network is trained on representations of the original data, and can subsequently "fit" or generate additional representations of new (e.g., previously unseen) data. Each hidden unit can further be associated with a one of the aforementioned weights that contributes to the output of the neural network, determined based on the activation function. The hidden units can be initialized with arbitrary weights (e.g., randomized weights). The hidden units can be initialized with a predetermined set of weights.

Each genomic region model can be a fully connected neural network. For example, a fully connected neural network comprises a first hidden layer comprising a corresponding plurality of hidden neurons, where each hidden neuron is connected to every neuron in the previous layer. Each genomic region model can be a partially connected neural network. For example, a partially connected neural network comprises a first hidden layer comprising a corresponding plurality of hidden neurons, where one or more hidden neurons are not connected to every neuron in the previous layer. Each hidden neuron can be associated with a corresponding weight in the corresponding plurality of weights for the corresponding genomic region model. One or more hidden neurons may not be associated with a corresponding weight for the corresponding genomic region model. The corresponding plurality of weights can further comprise a plurality of bias values.

The first activation function type can comprise tanh, sigmoid, softmax, Gaussian, Boltzmann-weighted averaging, absolute value, linear, rectified linear unit (ReLU), bounded rectified linear, soft rectified linear, parameterized rectified linear, average, max, min, sign, square, square root, multiquadric, inverse quadratic, inverse multiquadric, polyharmonic spline, or thin-plate spline. The second activation function type can be the same as the first activation function type. In some embodiments, the second activation function type can be different from the first activation function type.

A first genomic region model can have a different number of neurons in the first hidden layer than a second genomic region model (e.g., different neural networks for different regions can be different sizes). The number of hidden neurons in a genomic region model can be independently determined for the genomic region. The number of hidden neurons can be experimentally determined and/or optimized based on the performance of the genomic region model. For example, the performance of each genomic region model depends on the size of the genomic region model (e.g., the number of hidden units and/or layers) relative to the amount of available data for each genomic region model. A first genomic region model can have a different number of layers than a second genomic region model (e.g., different neural networks for different regions can have different numbers of layers). The corresponding plurality of hidden neurons can comprise between two neurons and forty-eight neurons, or between four neurons and twenty-four neurons. In some embodiments, a number of hidden layers in each corresponding trained neural network in the plurality of trained neural networks can comprise between two and five hidden layers.

The genomic region model can be a shallow neural network. A shallow neural network can be a neural network with few hidden layers. Such neural network architectures can improve the efficiency of neural network training and conserve computational power due to the reduced number of layers involved in the training. A number of hidden layers in each genomic region model can be between two and five hidden layers, or more than five layers. Each genomic region in the plurality of genomic regions can be represented by a single genomic region model. In some alternative embodiments, each genomic region in the plurality of genomic regions can be represented by a plurality of genomic region models. Each genomic region can be represented by between two and five genomic region models, and a value of a first corresponding weight in the corresponding first hidden layer can be different in each of the between two and five genomic region model. In some embodiments, each genomic region model can be represented by between two and five genomic region models, and a value of each corresponding weight in the first hidden layer can be independent in each of the between two and five genomic region model. The number of genomic region models can be independently determined for each respective genomic region. The number of genomic region models can be experimentally determined and/or optimized based on the performance of the corresponding trained neural network.

A genomic region model (e.g., a shallow neural network) can comprise an input layer that accepts inputs and an output layer that generates an output (e.g., a prediction value). The output can comprise a score (e.g., a probability or a likelihood) that an input (e.g., a fragment and/or a dataset) belongs to one or more predetermined classes (e.g., labels). The output can be determined by the genomic region model using a softmax or logistic regression algorithm. The output can be generated for each nucleic acid methylation fragment. The training of the genomic region model can use as input a dataset comprising a plurality of nucleic acid methylation fragments and/or methylation state vectors, after any processing and/or filtering of the dataset as described in the present disclosure. A genomic region model (e.g., trained and/or untrained) can use as input a dataset that is a subset of a plurality of nucleic acid methylation fragments. For example, the genomic region model uses as input a subset of nucleic acid methylation fragments, where for each nucleic acid methylation fragment in the subset of nucleic acid methylation fragments, all or a portion of the sequence of the respective nucleic acid methylation fragment is contained within the sequence spanned by the respective genomic region. Thus, the input for each genomic region model can be a different subset of nucleic acid methylation fragments.

The input used for training the genomic region model can be a transformation of a genomic dataset (e.g., by one-hot encoding). For example, the methylation state of each CpG site in the plurality of CpG sites for a respective nucleic acid methylation fragment is one-hot encoded in a two-dimensional vector that is applied to the genomic region model that corresponds to the respective genomic region. One-hot encoding can encode the methylation state for each CpG site in the methylation state vector of each nucleic acid methylation fragment. A first dimension (e.g., vector) can encode the methylated CpG sites, where the presence of a methylated CpG site is encoded as a "1" and the absence of a methylated CpG site is encoded as a "0". A second dimension (e.g., vector) can encode the unmethylated CpG sites, where the presence of an unmethylated CpG site is encoded as a "1" and the absence of an unmethylated CpG site is encoded as a "0". A CpG site that is neither methylated nor unmethylated (e.g., where methylation state is an alternate or unknown state) can be one-hot encoded as "0" and "0" in both the first and the second dimension. Missing CpG sites may not be assigned a value. One-hot encoding can be sparse in large genomic regions. Thus, a genomic region model can use as input a multi-dimensional dataset that is generated using one-hot encoding of a plurality of nucleic acid methylation fragments.

A genomic region model can use as input an incomplete or partial methylation state vector for a nucleic acid methylation fragment (e.g., where a portion of the nucleic acid sequence of the respective nucleic acid methylation fragment is contained within the genomic sequence spanned by the genomic region). For example, a nucleic acid methylation fragment comprises a portion of the CpG sites in a respective genomic region, the nucleic acid methylation fragment does not span the entire length of the genomic region, and/or the nucleic acid sequence of the nucleic acid methylation fragment is not wholly contained within the sequence spanned by the genomic region. In some such instances, any portion of the methylation state vector of the respective nucleic acid methylation fragment that maps to the respective genomic region can be nevertheless provided as input for the genomic region model, and any portion of the methylation state vector of the respective nucleic acid methylation fragment that extends beyond the sequence spanned by the respective genomic region can truncated, for the purposes of generating an input dataset for the genomic region model.

The one or more genomic region models can output a probability that the training subject has the cancer state, or a probability that the training subject has a corresponding cancer type. The cancer state can comprise presence of cancer, and the probability that the training subject has the cancer state is a probability that a training subject has cancer (e.g., presence or absence of cancer). The plurality of genomic region models can output 1, 2, 3, 4, 5, 6, 7, 8, 9, 10, 11, 12, 13, 14, 15, 16, 17, 18, 19, 20, or more than 20 classes. The one or more classes (e.g., cancer states and/or types)

determined by one or more genomic region model can be the same one or more classes (e.g., cancer states and/or types) across each genomic region in the plurality of genomic regions. Details of cancer types are described elsewhere herein.

Training a genomic region model (e.g., neural network) can comprise updating the weights through backpropagation (e.g., gradient descent). For backpropagation, the output of an untrained model (e.g., the prediction value generated by a neural network) can be generated using a set of arbitrarily selected initial weights. The output can then be compared with the original input (e.g., the corresponding label for the cancer state of the training subject from which the nucleic acid methylation fragment is obtained) by evaluating an error function to compute an error (e.g., using a loss function). The weights can then be updated such that the error is minimized (e.g., according to the loss function). The error can be computed using an error function (e.g., a loss function). The loss function can be mean square error, quadratic loss, mean absolute error, mean bias error, hinge, multi-class support vector machine, and/or cross-entropy. Training the genomic region model can comprise computing an error in accordance with a gradient descent algorithm and/or a minimization function. The error function can be used to update one or more weights in a genomic region model by adjusting the value of the one or more weights by an amount proportional to the calculated loss, thereby training the genomic region model. The amount by which the weights are adjusted can be metered by a predetermined learning rate that dictates the degree or severity to which weights are updated (e.g., smaller or larger adjustments). The learning rate can be a hyperparameter that can be selected by a practitioner.

The training can use a regularization on the corresponding weight of each hidden neuron in the corresponding plurality of hidden neurons. For example, a regularization is performed by adding a penalty to the loss function, where the penalty is proportional to the values of the weights in the trained or untrained neural network. Regularization can reduce the complexity of the model by adding a penalty to one or more weights to decrease the importance of the respective hidden neurons associated with those weights. Such practice can result in a more generalized model and reduce overfitting of the data. The regularization can include an L1 or L2 penalty. The regularization can comprise spatial regularization (e.g., determined based on a priori and/or experimental knowledge of methylation patterns in one or more genomic regions and/or a reference genome) or dropout regularization. The regularization can comprise penalties that are independently optimized for each genomic region.

Training the genomic region model can comprise at least 1, at least 2, at least 3, at least 4, at least 5, at least 6, at least 7, at least 8, at least 9, at least 10, at least 20, at least 30, at least 40, at least 50, at least 100, at least 500, at least 1000, at least 10,000, at least 50,000, at least 100,000, at least 200,000, at least 500,000, or at least 1 million evaluations of an error function. Training the genomic region model can comprise at least 1, at least 2, at least 3, at least 4, at least 5, at least 6, at least 7, at least 8, at least 9, at least 10, at least 20, at least 30, at least 40, at least 50, at least 100, at least 500, at least 1000, at least 10,000, at least 50,000, at least 100,000, at least 200,000, at least 500,000, or at least 1 million updatings of one or more weights based on the at least 1, at least 2, at least 3, at least 4, at least 5, at least 6, at least 7, at least 8, at least 9, at least 10, at least 20, at least 30, at least 40, at least 50, at least 100, at least 500, at least 1000, at least 10,000, at least 50,000, at least 100,000, at least 200,000, at least 500,000, or at least 1 million evaluations of an error function.

Training the genomic region model can comprise a minimum performance requirement. For example, training the genomic region model can comprise evaluating whether the error calculated satisfies an error threshold and/or a minimum performance requirement based on a validation training. The error threshold can comprise when the error is less than 20 percent, less than 18 percent, less than 15 percent, less than 10 percent, less than 5 percent, or less than 3 percent. The validation training can comprise a K-fold cross-validation. In this situation, a training dataset (e.g., one or more genomic data for one or more training subjects) can be divided into K bins. For each fold of training, one bin in the plurality of K bins can be left out of the training dataset and the neural network can be trained on the remaining K−1 bins. Performance of the trained or partially trained genomic region model can then be evaluated on the $K^{th}$ bin that is removed from the training. This process can be repeated K times, until each bin has been used once for validation. In some embodiments, K is 1, 2, 3, 4, 5, 6, 7, 8, 9, 10, 11, 12, 13, 14, 15, 16, 17, 18, 19, 20, or more than 20. In some embodiments, K is between 3 and 10. In some embodiments, training can be performed using K-fold cross-validation with shuffling. In this situation, K-fold cross-validation can be repeated by shuffling the training dataset (e.g., one or more genotypic datasets for a respective one or more training subjects) and performing a second K-fold cross-validation training. The shuffling can be performed so that each bin in the plurality of K bins in the second K-fold cross-validation is populated with a different (e.g., shuffled) subset of training data. In some embodiments, the training comprises shuffling the training dataset 1, 2, 3, 4, 5, 6, 7, 8, 9, 10, or more than 10 times. K-fold cross-validation can be further used to select and/or optimize parameters (e.g., number of hidden neurons and/or number of hidden layers) and/or hyperparameters (e.g., learning rate, penalties, etc.) for one or more genomic region model. In some embodiments, hyperparameters are predetermined and/or selected by a user or practitioner.

Other parameters and architectures can be used for training can include using stochastic gradient descent, multilayer perceptron, Tensorflow, variations in shallow neural network initialization (e.g., truncated normal), modifications in fragment fitting per genomic region (e.g., optimization of fragment size, fragment number, and/or fragment probability calibration), specificity thresholds for tail features (e.g., 100% specificity, +/−1 standard deviation, etc.), cluster computing (e.g., bigslice), cluster downsizing, alternative feature selection (e.g., genomic region-level binary classification and/or sample-level multi-class classification), alternative biological sample types (e.g., tissue and/or liquid biopsy samples), data augmentation, sample weighting, batch normalization, alternative loss functions (e.g., Huber), and/or calibration of genomic region-level models (e.g., for number of fragments, coverage, etc.).

In some embodiments, the methylation sequencing of nucleic acids in the biological sample obtained from the respective training subject is methylation sequencing of cell-free nucleic acids in the biological sample, and the method further comprises training the genomic region, at least in part, using methylation data for nucleic acid methylation fragments obtained from one or more tumor samples representative of the cancer state. For example, in some embodiments, output generated by a corresponding neural network trained using methylation data obtained from tumor samples can be used to compare the performance of the plurality of neural networks trained using methylation data obtained from cell-free nucleic acids (e.g., liquid biopsy samples). In some such embodiments, output generated by a corresponding neural network trained using methylation data obtained from tumor samples and output generated by a plurality of neural networks trained using methylation data obtained from cell-free nucleic acids can be used in tumor-matched classification assays.

III.B.iii Featurization Module

The featurization module 330 is trained to generate a feature vector for a sample (test or training) according to outputs by the region models 320. As noted above, outputs by the genomic regions models may be a cancer score for each DNA fragment or a region embedding for each DNA fragment. The featurization module may implement machine-learning algorithms, such as a neural network algorithm, a support vector machine algorithm, a decision tree algorithm, a multinomial logistic regression algorithm, a linear regression algorithm, or some other machine learning algorithm.

In embodiments where the region models output cancer scores for input DNA fragments, the featurization module 330 is trained to count fragments from each genomic region above a threshold score. Using cancer fragments derived from cancer samples and non-cancer fragments derived from non-cancer samples in a given genomic region, the analytics system may generate a distribution of cancer scores by inputting the cancer fragments and the non-cancer fragments into the genomic region model for the given genomic region. The analytics system may select a threshold score from the distribution based on a false positive budget or according to some other statistical calculation budget (e.g., false negative budget, true positive budget, etc.). The false positive budget can be a percentage of non-cancer fragments predicted to be cancer based on the threshold score. For example, the analytics system selects a threshold score of 0.10 for a particular region model which falls under the false positive budget of 70%, i.e., with the threshold score of 0.10, 70% of the non-cancer fragments can be included in the tally. The analytics system may determine a threshold score for counting fragments specific to each genomic region. After counting fragments with cancer scores above the threshold scores for the genomic regions, the result can be a feature vector wherein each feature is the count of fragments for each genomic region. With multiclass cancer scores determined for a fragment, the analytics system may generate features by counting fragments having a ratio between pairwise scores above a threshold, e.g., determining whether a log likelihood ratio between a first cancer type and a second cancer type surpasses a threshold for the pair of cancer types. The count of respective nucleic acid methylation fragments that satisfy a condition (e.g., a threshold score) can range between 0 and the total number of nucleic acid methylation fragments that map to the respective genomic region.

The featurization module 330 may also normalize counts based on sequencing depth of a fragment. For example, the feature is a ratio of the count of nucleic acid methylation fragments that satisfy the condition (e.g., having cancer) over the count of nucleic acid methylation fragments that fail to satisfy the condition. In some alternative embodiments, the feature is a ratio of the count of nucleic acid methylation fragments that satisfy the condition over the total number of nucleic acid methylation fragments that map to the respective genomic region. In some embodiments, the feature is a ratio of the count of nucleic acid methylation fragments that satisfy the condition for a first cancer state over the count of nucleic acid methylation fragments that satisfy the condition for a second cancer state.

For region models output cancer scores for input DNA fragments, generating feature vector (or feature) may comprise obtaining a respective feature of the genomic region for the respective training subject by using the respective genomic region model to score respective nucleic acid methylation fragments in the plurality of nucleic acid methylation fragments corresponding to the respective training subject that map to the respective genomic region for the cancer state, thereby obtaining a plurality of scores for feature generation.

The respective genomic region model can provide a unary output (e.g., probability of a cancer state). The respective feature of the genomic region provided by region models and/or featurization module can be a count of respective nucleic acid methylation fragments in the plurality of nucleic acid methylation fragments corresponding to the respective training subject that map to the respective genomic region for the cancer state that satisfy the condition:

$$\log\left(\frac{P(\text{cancer state})}{P(noncancer\ \text{state})}\right) > \text{threshold}.$$

where P(cancer state) is a probability that the respective nucleic acid methylation fragment is associated with the cancer state provided by the genomic region model that corresponds to the respective genomic region upon inputting the respective nucleic acid methylation fragment into the genomic region model. Further, P(noncancer state)=1−P (cancer state). Here, the threshold can be an application-dependent fixed value. In some embodiments, the corresponding genomic region model computes P(cancer state) and P(noncancer state) is calculated as 1−P(cancer state).

For example, for each respective nucleic acid methylation fragment in the plurality of nucleic acid methylation fragments corresponding to the respective training subject that map to the respective genomic region, the corresponding genomic region model computes a prediction value that is the probability that the fragment has a cancer state (e.g., cancer). Thus, the respective nucleic acid methylation fragment can be scored using the genomic region model, where the score outputted by the genomic region model comprises the probability that the fragment has the cancer state and/or a calculation based on the probability that the fragment has the cancer state (e.g., $$\text{(e.g., } \log\left(\frac{P(\text{cancer state})}{P(noncancer\ \text{state})}\right)\text{).}$$

In the featurization module, the respective nucleic acid methylation fragment can be subsequently tallied if the resulting score satisfies the condition defined above (e.g., a fixed value threshold). Then, for each respective genomic region in the plurality of genomic regions, the respective feature for the genomic region can be the tallied count of all the nucleic acid methylation fragments that map to the respective genomic region that satisfy the condition.

Each feature in the plurality of features (e.g., a count of nucleic acid methylation fragments that map to a respective genomic region and satisfy a condition) can indicate the degree of signal for a particular cancer state. For example, a feature represents the extent to which a genomic region is associated with a cancer condition of interest, based on the methylation patterns of the nucleic acid methylation fragments that map to that genomic region. Viewed another way, in some instances, the plurality of features represent the spatial distribution of nucleic acid methylation fragments associated with a cancer state, across the plurality of genomic regions in a human reference genome. A plurality of features for a corresponding plurality of genomic regions can be in the form of a feature vector (e.g., a vector of counts). The feature vector can be used to determine the cancer state of the subject (e.g., as input to a downstream supervised model).

The threshold can be positive or negative. The threshold can be between 0.1 and 1, between 1 and 5, between 5 and 10, between 10 and 50, between 50 and 100, or greater than 100. In some embodiments, the threshold is between −0.1 and −1, between −1 and −5, between −5 and −10, between −10 and −50, between −50 and −100, or less than −100. In some embodiments, the threshold is zero.

In some alternative embodiments, the corresponding genomic region model can provide a binary and/or a multiclass output (e.g., probabilities of a first cancer state and a second cancer state). For example, the respective feature of the genomic region for the respective training subject is a count of respective nucleic acid methylation fragments in the plurality of nucleic acid methylation fragments corresponding to the respective training subject that map to the respective genomic region for the cancer state that satisfy the condition:

$$\log\left(\frac{P(\text{first cancer state})}{P(\text{second cancer state})}\right) > \text{threshold}.$$

Here, P(first cancer state) is a first probability that the respective nucleic acid methylation fragment is associated with the first cancer state, where the first probability is provided by the corresponding genomic region model that corresponds to the respective genomic region upon inputting the respective nucleic acid methylation fragment into the corresponding genomic region model. Further, P(second cancer state) is a second probability that the respective nucleic acid methylation fragment is associated with the second cancer state, where the second probability is provided by the corresponding genomic region model that corresponds to the respective genomic region upon inputting the respective nucleic acid methylation fragment into the corresponding genomic region model. The value "threshold" can be a fixed application-dependent value.

The corresponding genomic region model can compute a separate probability for each cancer state in a plurality of cancer states as well as the noncancer state upon inputting the respective nucleic acid methylation fragment into the corresponding trained neural network. The cancer state can be any one of a presence or absence of cancer, type of cancer, stage of cancer, and/or tissue of origin as disclosed herein. The non-cancer state can be any one of a presence or absence of cancer, type of cancer, stage of cancer, and/or tissue of origin as disclosed herein that is different from the cancer state. A separate probability can be calculated for any one of the plurality of possible cancer states and/or non-cancer states (e.g., a presence or absence of cancer, type of cancer, stage of cancer, and/or tissue of origin). A separate probability can be calculated for 1, 2, 3, 4, 5, 6, 7, 8, 9, 10, 11, 12, 13, 14, 15, 16, 17, 18, 19, 20, or more than 20 possible cancer states.

The performing feature identification (e.g., generating a feature) can use those respective nucleic acid methylation fragments for feature identification that, when evaluated by the region models and/or featurization module, have a collective specificity across the plurality of training subjects that exceeds a specificity threshold value (e.g., feature identification comprises a specificity requirement). The specificity threshold value can be a value between 0.9500 and 0.99999. In some embodiments, the specificity threshold value is 0.999, 0.9999, or 0.99999.

The performing feature identification can be performed using a multi-genomic region. The multi-genomic region can comprise a subset of the plurality of genomic regions, and the performing feature identification can make use of a multi-genomic region model that accepts, as input, an output of each genomic region model corresponding to a genomic region in the subset of the plurality of genomic regions in order to obtain a respective feature of each genomic region in the subset of the plurality of genomic regions for the respective training subject or a single feature for the subset of the plurality of genomic regions.

The multi-genomic region model can be an independent model that is trained independently from the training of the plurality of corresponding single-region models (e.g., a single region model can be one genomic region model). In some such embodiments, the multi-genomic region model accepts, as input, one or more features identified using the plurality of corresponding single-region models for the respective plurality of genomic regions, and one or more corresponding labels for the cancer states of the respective training subjects.

The multi-genomic region model can be trained concurrently with the training of the plurality of corresponding single-region models for the respective plurality of genomic regions. In some such embodiments, the multi-genomic region model does not accept output from the plurality of corresponding single-region models as input, but rather is trained "end-to-end" using the plurality of genomic dataset from each training subject of the plurality of training subjects, and one or more corresponding labels for the cancer states of the respective training subjects. Generally, such "end-to-end" training may not rely on the intermediate output of the single-region models to train the multi-genomic model, but rather rely on the labels of each patient sample to determine the classification of the patient, as a whole, based on the respective plurality of genomic regions. Details of one example of the "end-to-end" training are described elsewhere herein. Features identified using any of the methods disclosed herein can be used for target panel optimization (e.g., selection of genomic regions with high cancer signal) to train a downstream cancer classifier.

In embodiments where the region models output region embeddings for input DNA fragments, the featurization module 330 is trained to generate the feature vector by pooling the region embeddings of the DNA fragments. The overall pooling of region embeddings of the DNA fragments to generate the feature vector may comprise one or more pooling steps. In one example, there may be two pooling steps. A first pooling step can determine an aggregate region vector for each genomic region by pooling the region embeddings of DNA fragments in each genomic region. Understandably, if a sample has no DNA fragments in a given region, the aggregate region vector can be a zero vector. A second pooling step can determine the feature vector by pooling the aggregate region vectors across the genomic regions. Each pooling step can include performing an average pooling operation, a max pooling operation, another weighted geometric pooling operation, another pooling operation, or some combination thereof. Each pooling step may be defined by a kernel size, i.e., referring to the size of the pooling window for each dimension of the input tensor, and a stride, i.e., referring to the size of the sliding window for each dimension of the input tensor. In one example, a global pooling operation at the second pooling step has the kernel size and the stride equal to the number of genomic regions (or the number of fragments in a genomic region). In other implementations, the kernel size can be any of the following: 1, 2, 3, 4, 5, 6, 7, 8, 9, 10, 12, 14, 16, 18, and 20; whereas the stride can be any of the following: 1, 2, 3, 4, 5, 6, 7, 8, 9, 10, 12, 14, 16, 18, and 20. For example, the first pooling step of determining an aggregate region vector for each genomic region comprises performing an average pooling of the region embeddings of DNA fragments, effectively averaging the region embeddings. With max pooling, each entry in the aggregate region vector can be the corresponding maximum value at that entry position across the region embeddings for DNA fragments in the genomic region. The analytics system may also adjust weights in the pooling operations, e.g., when training the featurization module 330 concurrently the region models 320 and/or the cancer classifier 340.

III.B.iv Cancer Classifier

With the feature vectors of the training samples, the analytics system may train the cancer classifier 340.

The analytics system may train the cancer classifier 340 for binary classification to distinguish between cancer and non-cancer based on the feature vectors of the training samples. In this manner, the analytics system can use training samples that include both non-cancer samples from healthy individuals and cancer samples from subjects. Each training sample may have one of the two labels "cancer" or "non-cancer." In this embodiment, the class classifier 340 outputs a cancer prediction indicating the likelihood of the presence or absence of cancer.

The analytics system may train the cancer classifier 340 for multiclass classification to distinguish between many cancer types (also referred to as tissue of origin (TOO) labels). Cancer types can include one or more cancers and may include a non-cancer type (may also include any additional other diseases or genetic disorders, etc.). To do so, the analytics system can use the cancer type cohorts and may also include or not include a non-cancer type cohort. In this multi-cancer embodiment, the cancer classifier 340 is trained to determine a cancer prediction (or, more specifically, a TOO prediction) that comprises a prediction value for each of the cancer types being classified for. The prediction values may correspond to a likelihood that a given training sample (and during inference, a test sample) has each of the cancer types. In one implementation, the prediction values are scored between 0 and 100, wherein the cumulation of the prediction values equals 100. For example, the cancer classifier returns a cancer prediction including a prediction value for breast cancer, lung cancer, and non-cancer. For example, the classifier can return a cancer prediction that a test sample is 65% likelihood of breast cancer, 25% likelihood of lung cancer, and 10% likelihood of non-cancer. The analytics system may further evaluate the prediction values to generate a prediction of a presence of one or more cancers in the sample, also may be referred to as a TOO prediction indicating one or more TOO labels, e.g., a first TOO label with the highest prediction value, a second TOO label with the second highest prediction value, etc. Continuing with the example above and given the percentages, in this example the system may determine that the sample has breast cancer given that breast cancer has the highest likelihood.

In general, the analytics system can train the cancer classifier 340 by inputting sets of training samples with their feature vectors into the cancer classifier 340 and adjusting classification parameters so that a function of the classifier accurately relates the training feature vectors to their corresponding label. The analytics system may group the training samples into sets of one or more training samples for iterative batch training of the cancer classifier. After inputting all sets of training samples including their training feature vectors and adjusting the classification parameters, the cancer classifier 340 can be sufficiently trained to label test samples according to their feature vector within some margin of error. The analytics system may train the cancer classifier 340 according to any one of a number of methods. As an example, the binary cancer classifier may be a L2-regularized logistic regression classifier that is trained using a log-loss function. As another example, the multi-cancer classifier may be a multinomial logistic regression. In practice either type of cancer classifier 340 may be trained using other techniques. These techniques can be numerous including potential use of kernel methods, decision trees, random forest classifier, a mixture model, an autoencoder model, machine learning algorithms such as multilayer neural networks, etc.

The cancer classifier 340 may also comprise a first stage binary classifier and a second stage multiclass classifier. The first stage binary classifier can return a binary prediction for a test sample. The binary prediction may be whether the test subject likely has or likely does not have cancer. In other implementations, the cancer prediction includes prediction values that describe likelihood of cancer and likelihood of non-cancer. For example, the cancer prediction has a cancer prediction value of 85% and the non-cancer prediction value of 15%. The analytics system may determine the test subject to likely have cancer. In response to determining a likelihood of cancer above a threshold, the second stage multiclass classifier can return a multiclass cancer prediction for the test sample. The multiclass classifier can receive the test feature vector and returns a cancer prediction of a cancer type of the plurality of cancer types. For example, the multiclass cancer classifier provides a cancer prediction specifying that the test subject is most likely to have ovarian cancer. In another implementation, the multiclass cancer classifier provides a prediction value for each cancer type of the plurality of cancer types. For example, a cancer prediction may include a breast cancer type prediction value of 40%, a colorectal cancer type prediction value of 15%, and a liver cancer prediction value of 45%.

The cancer classifier can comprise a logistic regression, a neural network algorithm, a support vector machine algorithm, a Naive Bayes algorithm, a nearest neighbor algorithm, a boosted trees algorithm, a random forest algorithm, a decision tree algorithm, a multinomial logistic regression algorithm, a linear model, a linear regression algorithm, a 2-stage stochastic gradient descent (SGD) model, or a deep neural network (e.g., a deep-and-wide sample-level classifier). The cancer classifier can be trained to predict a cancer state based on a corresponding feature for a respective genomic region. The cancer classifier can be trained to predict a cancer state based on a plurality of corresponding features for a respective plurality of genomic regions.

The cancer classifier can accept as input a vector (or a feature vector), where the vector is associated with a respective training subject in the plurality of training subjects and each element of the vector is a respective feature of a different genomic region in the plurality of genomic regions computed via the region models and/or featurization module using respective nucleic acid methylation fragments in the plurality of nucleic acid methylation fragments corresponding to the respective training subject that map to the different genomic region. For example, the input can be a feature vector obtained using one or more corresponding genomic region models and/or the featurization module for a respective one or more genomic regions. The feature vector can be a vector of counts, ratios, and/or one-hot encoded genomic regions indicating genomic regions associated with cancer.

The training of the cancer classifier can be performed based on the feature vector provided as input from the featurization module, and a corresponding label for the cancer state of each respective training subject in the plurality of training subjects. The training of the cancer classifier can be performed independent of the training of the region models and/or featurization module. In some such embodiments, the plurality of weights for each corresponding genomic region model for each respective genomic region is fixed such that the training of the cancer classifier does not result in an updating of the plurality of weights for the corresponding genomic region model.

In some embodiments, the region models training, the featurization module training, and the cancer classifier training are performed in a combined training that jointly trains the plurality of genomic region models, featurization module, and the cancer classifier. In some such embodiments, one or more weights in the plurality of weights for each corresponding genomic region model is not fixed such that the combined training updates one or more weights in the plurality of weights for the corresponding genomic region model. In some such embodiments, the combined training is performed "end-to-end" for multi-genomic region model.

A combination of region models, multi-genomic region model and a downstream cancer classifier can be used to generate outputs with greater complexity. For example, region models, a multi-genomic region model and/or a downstream supervised model can be used to predict higher-order (e.g., sample-level and/or subject-level), multi-class classifications, based on the plurality of features identified using the region-level models across the plurality of genomic regions. Region-level binary classification can therefore perform an initial identification and selection of, e.g., the proportion of anomalous nucleic acid methylation fragments that map to a respective genomic region. By identifying genomic regions comprising high signal for the condition of interest (e.g., by providing a count of anomalous nucleic acid methylation fragments with a high probability of association), the sensitivity and accuracy of such higher-order classifications can be improved. A first plurality of training subjects can be used to train the plurality of genomic region models and/or the multi-region model, and a second plurality of training subjects, different from the first plurality of training subjects, can be used to train the downstream cancer classifier.

III.C. Deployment of Cancer Classification

Figure 5:
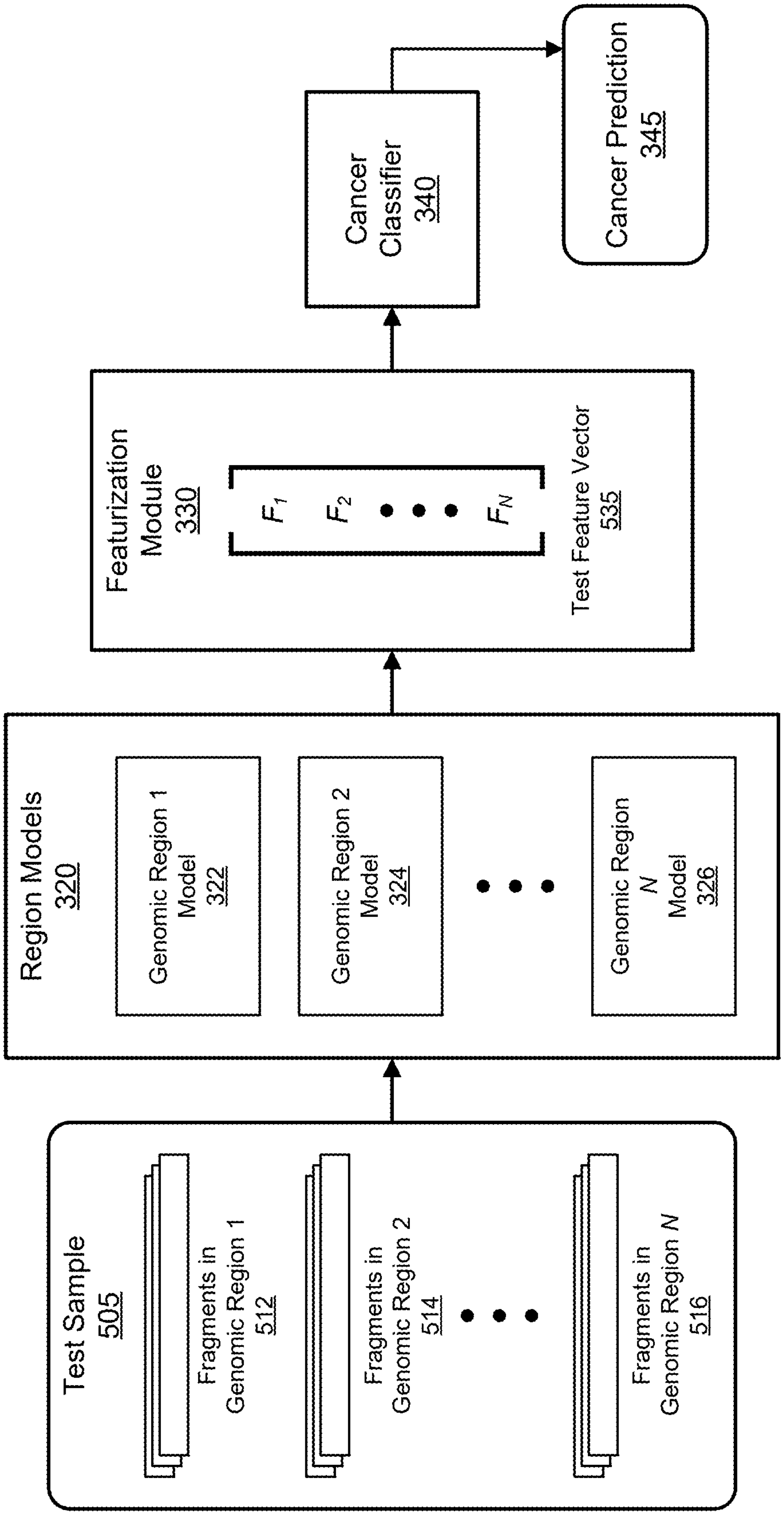
FIG. 5 is an exemplary flowchart illustrating cancer classification of a test sample according to the first architecture, according to one or more embodiments.

FIG. 5 is a flowchart illustrating cancer classification of a test sample according to a first architecture, according to an embodiment. The analytics system can obtain a test sample 505 of an unknown cancer status comprising a plurality of DNA fragments. The analytics system may process the test sample 505, e.g., with any combination of the processes 100 and 220 to determine a set of anomalously methylated fragments. The analytics system can group the fragments by genomic regions, resulting in fragments 512 in Genomic Region 1, fragments 514 in Genomic Region 2, and continuing up to fragments 516 in Genomic Region N, where N represents the total number of genomic regions.

The analytics system can input the fragments of the test sample 505 into the region models 320 to determine a cancer score for each fragment. For example, fragments 512 in Genomic Region 1 are input into Genomic Region 1 model 322; fragments 514 in Genomic Region 2 are input into Genomic Region 2 model 324; continuing up to fragments 516 in Genomic Region N input into Genomic Region N model 326. Each region model may be a neural network, e.g., independently trained from the others. The region models can output a cancer score for each fragment. The cancer score can be a binary score between cancer and non-cancer, e.g., a likelihood of cancer, or a multiclass score between a plurality of cancer types, e.g., a likelihood of each cancer type. For example, Genomic Region 1 model 322 outputs a cancer score for each fragment of fragments 512 in Genomic Region 1; Genomic Region 2 model 324 outputs a cancer score for each fragment of fragments 514 in Genomic Region 2; continuing to Genomic Region N model 326 outputting a cancer score for each fragment of fragments 516 in Genomic Region N.

The analytics system can generate a test feature vector 535 with the featurization module 330 based on the cancer scores for the fragments of the test sample 505. The analytics system can count the number of fragments 512 in Genomic Region 1 having cancer scores above a threshold score for Genomic Region 1. The analytics system can similarly count the number of fragments of fragments 514 in Genomic Region 2 having cancer scores above a threshold score for Genomic Region 2. The analytics system can continue so on and so forth with remaining genomic regions, up to counting the number of fragments 516 in Genomic Region N having cancer scores above a threshold score for Genomic Region N. The counts can correspond to the features in the test feature vector 535, e.g., $F_1$ is based on the counts for Genomic Region 1, $F_2$ is based on the counts for Genomic Region 2, and similarly for remaining genomic regions, up to $F_N$ being based on counts for Genomic Region N. The counts may be further normalized, e.g., according to sequencing depth for the test sample 505, wherein the features are the normalized counts.

The analytics system can input the test feature vector 535 into the cancer classifier 340 to return a cancer prediction 345. As mentioned above, the cancer prediction 345 may be a binary prediction and/or a multiclass prediction.

Figure 6:
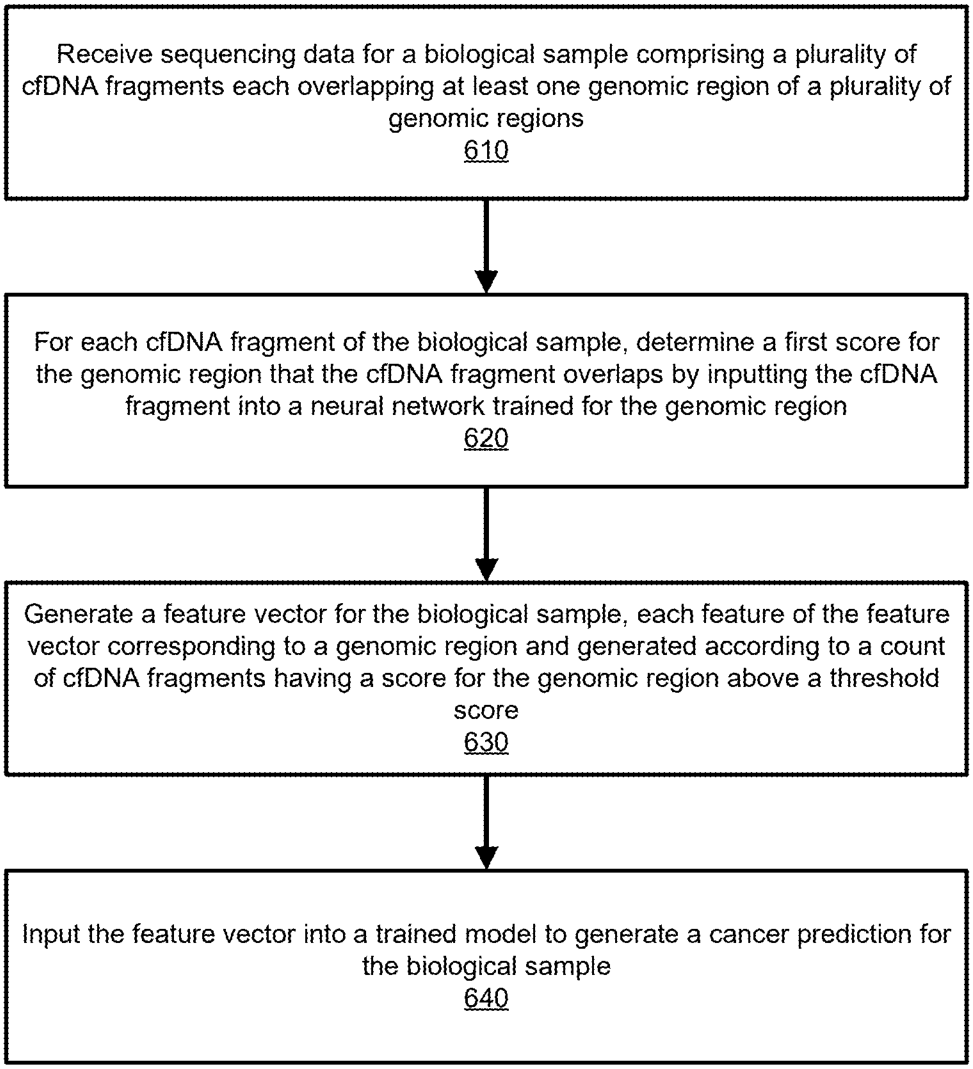
FIG. 6 is an exemplary flowchart describing the process of cancer classification shown in FIG. 5, according to one or more embodiments.

FIG. 6 is a flowchart describing the process 600 of cancer classification described in FIG. 5, according to an embodiment. Although the following description is in perspective of the analytics system, the following description can be performed by any combination of the components (e.g., the methylation embedding model 310, the region models 320, the featurization module 330, and the cancer classifier 340 of FIG. 3) described herein this disclosure.

The analytics system receives 610 sequencing data for a biological sample comprising a plurality of cfDNA fragments. Each cfDNA fragment overlapping at least one genomic region of a plurality of genomic regions. In some cases, a cfDNA fragment may span across two or more genomic regions, wherein the analytics system may place the cfDNA fragment into each of the genomic regions or may place the cfDNA fragment into the genomic region that it mostly overlaps.

The analytics system, for each cfDNA fragment of the biological sample, determines 620 a first score for the genomic region that the cfDNA fragment overlap. The first score for a genomic region can be determined by inputting the cfDNA fragment into a neural network trained for the genomic region, e.g., as described above in FIG. 4A. The neural network can be configured to generate the first score, as a binary prediction, representative of a likelihood that the cfDNA fragment is derived from a cancer biological sample. The neural network may also be configured to generate a first score corresponding to a likelihood that the cfDNA fragment is derived from a cancer biological sample of a first cancer type and a second score corresponding to a likelihood that the cfDNA is derived from a cancer biological sample of a second cancer type. A first neural network for a first genomic region may be variably sized to a second neural network for a second genomic region. For example, the first neural network may have a different number of hidden layers than the second neural network. In another example, the two neural networks both have one hidden layer, but the first neural network has a different number of nodes in its hidden layer than the second neural network.

The analytics system generates 630 a feature vector for the biological sample. Each feature of the feature vector can correspond to a genomic region and be generated according to a count of cfDNA fragments having a score for the genomic region above a threshold score. Each threshold score may be determined for each genomic region according to a false positive budget (or another statistical measure). The analytics system may normalize the counts according to sequencing depth for the biological sample.

The analytics system inputs 640 the feature vector into a trained model to generate a cancer prediction for the biological sample. The trained model may be the cancer classifier 340 described above in FIG. 3. The cancer prediction may be a binary prediction between cancer and non-cancer and/or a multiclass prediction between a plurality of cancer types.

Figure 7:
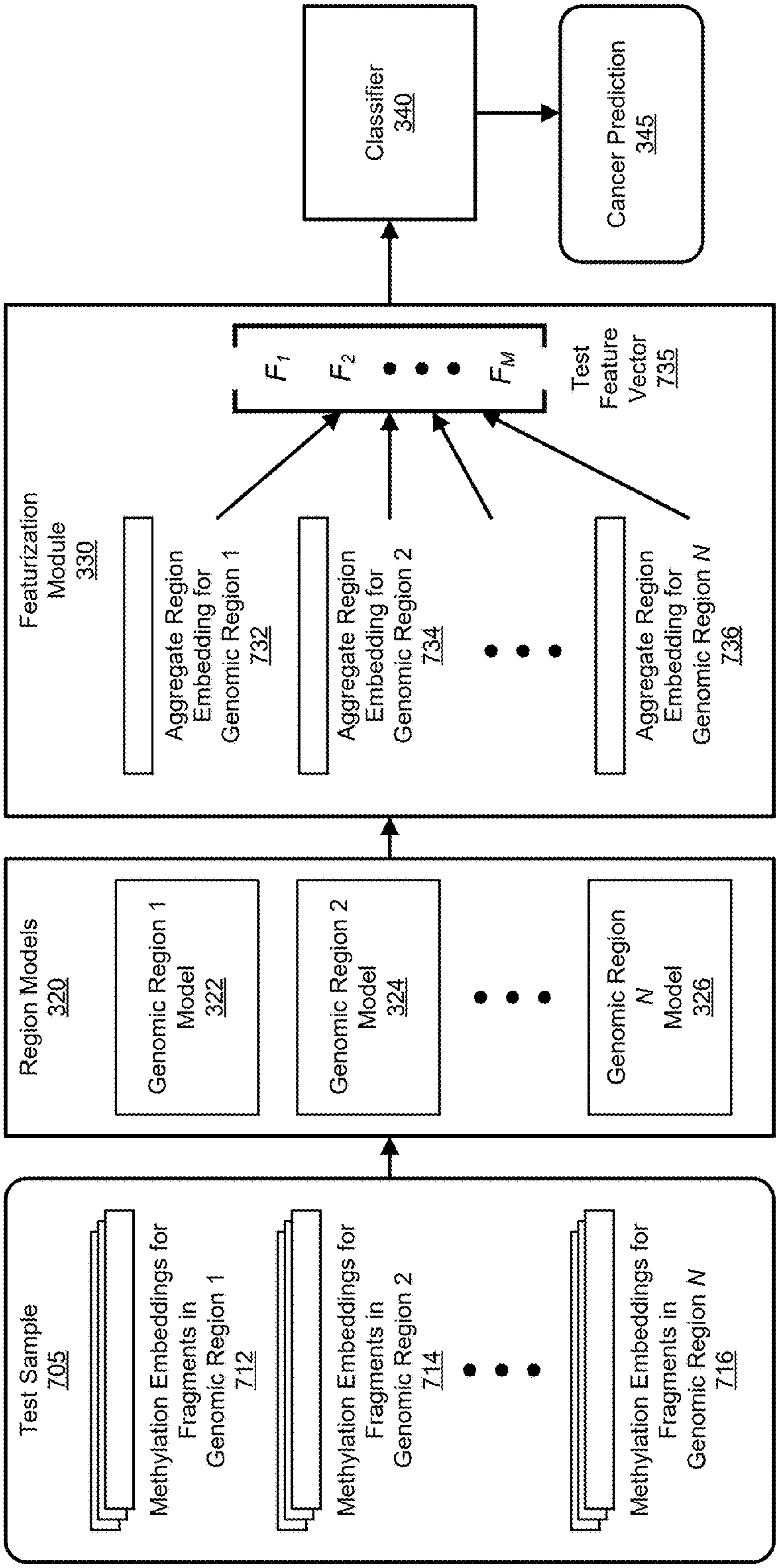
FIG. 7 is an exemplary flowchart illustrating cancer classification of a test sample according to the second architecture, according to one or more embodiments.

FIG. 7 is a flowchart illustrating cancer classification of a test sample according to a second architecture, according to an embodiment. The analytics system can obtain a test sample 705 of an unknown cancer status comprising a plurality of DNA fragments. The analytics system may process the test sample 705, e.g., with any combination of the processes 100 and 220 to determine a set of anomalously methylated fragments. The analytics system can determine a methylation embedding for each fragment by inputting the cfDNA fragment into the methylation embedding model 310. The analytics system can group the fragments by genomic regions, resulting in methylation embeddings 712 for fragments in Genomic Region 1, methylation embeddings 714 for fragments in Genomic Region 2, and continuing up to methylation embeddings 716 for fragments in Genomic Region N, where N represents the total number of genomic regions.

The analytics system can input the methylation embeddings into the region models 320 to determine a region embedding for each methylation embedding. For example, methylation embeddings 712 are input into Genomic Region 1 model 322 yielding region embeddings for the methylation embeddings 712; methylation embeddings 714 are input into Genomic Region 2 model 324 yielding region embeddings for the methylation embeddings 714; and continuing up to methylation embeddings 716 input into Genomic Region N model 326 yielding region embeddings for the methylation embeddings 716. Each region model may be a trained independently from other components or concurrently with other components.

The analytics system can feed the region embeddings output by the region models 320 to the featurization module 330 to generate a test feature vector for the test sample 705. The featurization module 330 may pool the region embeddings output by the region models 320 to generate the test feature vector. The featurization module 330 may pool the region embeddings in two pooling steps. In a first pooling step, the featurization module 330 can pool region embeddings for each genomic region into an aggregate region embedding. For example, the featurization module 330 pools the region embeddings determined for methylation embeddings 712 into an aggregate region embedding 732 for Genomic Region 1; likewise pools the region embeddings for Genomic Region 2 into an aggregate region embedding 734 for Genomic Region 2; and continuing up to pooling region embeddings for Genomic Region N into an aggregate region embedding 736 for Genomic Region N. In a second pooling step, the featurization module 330 pools the aggregate region embeddings (e.g., aggregate region embeddings 732, 734, and up to 736) into the test feature vector 735. In the figure, the test feature vector 735 comprises features $F_1$, $F_2$, . . . $F_M$, wherein M is the total number of features in the test feature vector. The variable M (number of features) may or may not be equal to the variable N (number of genomic regions).

The analytics system can input the test feature vector 735 into the cancer classifier 340 to return a cancer prediction 345. As mentioned above, the cancer prediction 345 may be a binary prediction and/or a multiclass prediction.

Figure 8:
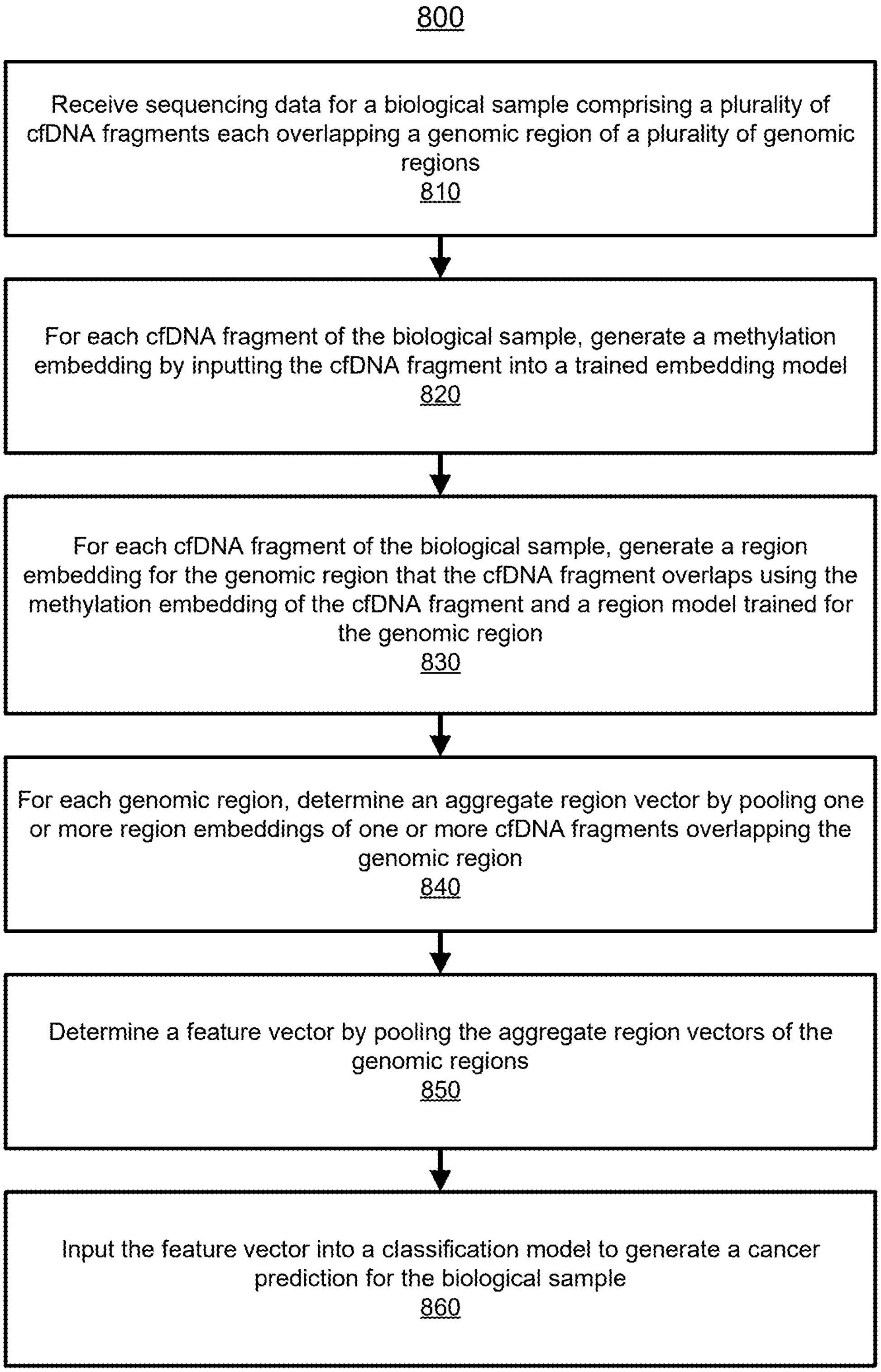
FIG. 8 is an exemplary flowchart describing the process of cancer classification shown in FIG. 7, according to one or more embodiments.

FIG. 8 is a flowchart describing the process 800 of cancer classification described in FIG. 7, according to an embodiment. Although the following description is in perspective of the analytics system, the following description can be performed by any combination of the components (e.g., the methylation embedding model 310, the region models 320, the featurization module 330, and the cancer classifier 340 of FIG. 3) described herein this disclosure.

The analytics system receives 810 sequencing data for a biological sample comprising a plurality of cfDNA fragments. Each cfDNA fragment can overlap at least one genomic region of a plurality of genomic regions. In some cases, a cfDNA fragment may span across two or more genomic regions, wherein the analytics system may place the cfDNA fragment into each of the genomic regions or may place the cfDNA fragment into the genomic region that it mostly overlaps.

The analytics system, for each cfDNA fragment of the biological sample, generates 820 a methylation embedding by inputting the cfDNA fragment into a trained embedding model, e.g., as described above in FIG. 3. The embedding model can be configured to generate a methylation embedding based on an input cfDNA fragment.

The analytics system, for each cfDNA fragment of the biological sample, generates 830 a region embedding for the genomic region that the cfDNA overlaps. The region embedding for a genomic region can be determined by inputting the methylation embedding of the cfDNA fragment into a region model trained for the genomic region that the cfDNA fragment overlaps. As such, each region model can be configured to generate a region embedding based on an input methylation embedding of a cfDNA fragment that overlaps the genomic region. The region models may be concurrently trained with other components of the cancer classification process.

The analytics system, for each genomic region, determines 840 an aggregate region vector by pooling one or more region embeddings of one or more cfDNA fragments overlapping the genomic region. Pooling of region embeddings may comprise performing a max pooling operation, an average pooling operation, some other geometric pooling operation, or some combination thereof. The aggregate region vector may or may not be of the same length as the region embeddings that are pooled together.

The analytics system, for each genomic region, determines 850 a feature vector by pooling the aggregate region vectors of the genomic regions. Pooling of the aggregate region vectors may comprise performing a max pooling operation, an average pooling operation, some other geometric pooling operation, or some combination thereof. The feature vector for the biological sample may or may not be of the same length as the aggregate region vectors that are pooled together. In one example, the feature vector is of a length equal the number of genomic regions considered.

The analytics system inputs 840 the feature vector into a trained model to generate a cancer prediction for the biological sample. The trained model may be the cancer classifier 340 described above in FIG. 3. The cancer prediction may be a binary prediction between cancer and non-cancer and/or a multiclass prediction between a plurality of cancer types.

In some embodiments, classifying a test subject can comprise obtaining a plurality of test nucleic acid methylation fragments. The respective test nucleic acid methylation fragment in the corresponding plurality of test nucleic acid methylation fragments can comprise a corresponding methylation pattern comprising a methylation state of each CpG site in a corresponding plurality of CpG sites of the respective test nucleic acid methylation fragment. The plurality of test nucleic acid methylation fragments can be determined by methylation sequencing of nucleic acids in a biological sample obtained from the test subject. Classifying a test subject can further comprise performing test feature identification via region models and featurization module for each respective genomic region in the plurality of genomic regions. Test feature identification can be performed by obtaining a respective test feature of the genomic region for the test subject by using the region models and featurization module to score respective test nucleic acid methylation fragments for the cancer state and generate a feature vector based on the cancer state, thereby obtaining a plurality of test features that includes a test feature for each genomic region in the plurality of genomic regions. Classifying a test subject can further comprise applying the plurality of test features to the cancer classifier to determine whether the test subject has the cancer state. The plurality genomic region models and featurization module can be used to identify a plurality of genomic region-level features from a training dataset for training a cancer classifier, and the using the cancer classifier to classify a test subject is performed by applying a plurality of features from a test dataset to the cancer classifier.

Any of the systems and methods disclosed herein can be used to obtain and/or process the biological samples and/or nucleic acid methylation fragments obtained from the test subject. Any of the systems and methods disclosed herein can be used to train the region models (e.g., shallow neural network), obtain features via featurization module, and/or train the cancer classifier used for determining whether the test subject has the cancer state.

IV. Applications

In some embodiments, the methods, analytic systems and/or classifier of the present invention can be used to detect the presence of cancer, monitor cancer progression or recurrence, monitor therapeutic response or effectiveness, determine a presence or monitor minimum residual disease (MRD), or any combination thereof. For example, as described herein, a classifier can be used to generate a probability score (e.g., from 0 to 100) describing a likelihood that a test feature vector is from a subject with cancer. In some embodiments, the probability score is compared to a threshold probability to determine whether or not the subject has cancer. In other embodiments, the likelihood or probability score can be assessed at multiple different time points (e.g., before or after treatment) to monitor disease progression or to monitor treatment effectiveness (e.g., therapeutic efficacy). In still other embodiments, the likelihood or probability score can be used to make or influence a clinical decision (e.g., diagnosis of cancer, treatment selection, assessment of treatment effectiveness, etc.). For example, in one embodiment, if the probability score exceeds a threshold, a physician can prescribe an appropriate treatment.

IV.A. Early Detection of Cancer

In some embodiments, the methods and/or classifier of the present invention are used to detect the presence or absence of cancer in a subject suspected of having cancer. For example, a classifier (e.g., as described above in Section III and exampled in Section V) can be used to determine a cancer prediction describing a likelihood that a test feature vector is from a subject that has cancer.

In one embodiment, a cancer prediction is a likelihood (e.g., scored between 0 and 100) for whether the test sample has cancer (i.e. binary classification). Thus, the analytics system may determine a threshold for determining whether a test subject has cancer. For example, a cancer prediction of greater than or equal to 60 can indicate that the subject has cancer. In still other embodiments, a cancer prediction greater than or equal to 65, greater than or equal to 70, greater than or equal to 75, greater than or equal to 80, greater than or equal to 85, greater than or equal to 90, or greater than or equal to 95 indicates that the subject has cancer. In other embodiments, the cancer prediction can indicate the severity of disease. For example, a cancer prediction of 80 may indicate a more severe form, or later stage, of cancer compared to a cancer prediction below 80 (e.g., a probability score of 70). Similarly, an increase in the cancer prediction over time (e.g., determined by classifying test feature vectors from multiple samples from the same subject taken at two or more time points) can indicate disease progression or a decrease in the cancer prediction over time can indicate successful treatment.

In another embodiment, a cancer prediction comprises many prediction values, wherein each of a plurality of cancer types being classified (i.e. multiclass classification) for has a prediction value (e.g., scored between 0 and 100). The prediction values may correspond to a likelihood that a given training sample (and during inference, training sample) has each of the cancer types. The analytics system may identify the cancer type that has the highest prediction value and indicate that the test subject likely has that cancer type. In other embodiments, the analytics system further compares the highest prediction value to a threshold value (e.g., 50, 55, 60, 65, 70, 75, 80, 85, etc.) to determine that the test subject likely has that cancer type. In other embodiments, a prediction value can also indicate the severity of disease. For example, a prediction value greater than 80 may indicate a more severe form, or later stage, of cancer compared to a prediction value of 60. Similarly, an increase in the prediction value over time (e.g., determined by classifying test feature vectors from multiple samples from the same subject taken at two or more time points) can indicate disease progression or a decrease in the prediction value over time can indicate successful treatment.

According to aspects of the invention, the methods and systems of the present invention can be trained to detect or classify multiple cancer indications. For example, the methods, systems and classifiers of the present invention can be used to detect the presence of one or more, two or more, three or more, five or more, ten or more, fifteen or more, or twenty or more different types of cancer.

Examples of cancers that can be detected using the methods, systems and classifiers of the present invention include carcinoma, lymphoma, blastoma, sarcoma, and leukemia or lymphoid malignancies. More particular examples of such cancers include, but are not limited to, squamous cell cancer (e.g., epithelial squamous cell cancer), skin carcinoma, melanoma, lung cancer, including small-cell lung cancer, non-small cell lung cancer ("NSCLC"), adenocarcinoma of the lung and squamous carcinoma of the lung, cancer of the peritoneum, gastric or stomach cancer including gastrointestinal cancer, pancreatic cancer (e.g., pancreatic ductal adenocarcinoma), cervical cancer, ovarian cancer (e.g., high grade serous ovarian carcinoma), liver cancer (e.g., hepatocellular carcinoma (HCC)), hepatoma, hepatic carcinoma, bladder cancer (e.g., urothelial bladder cancer), testicular (germ cell tumor) cancer, breast cancer (e.g., HER2 positive, HER2 negative, and triple negative breast cancer), brain cancer (e.g., astrocytoma, glioma (e.g., glioblastoma)), colon cancer, rectal cancer, colorectal cancer, endometrial or uterine carcinoma, salivary gland carcinoma, kidney or renal cancer (e.g., renal cell carcinoma, nephroblastoma or Wilms' tumor), prostate cancer, vulval cancer, thyroid cancer, anal carcinoma, penile carcinoma, head and neck cancer, esophageal carcinoma, and nasopharyngeal carcinoma (NPC). Additional examples of cancers include, without limitation, retinoblastoma, thecoma, arrhenoblastoma, hematological malignancies, including but not limited to non-Hodgkin's lymphoma (NHL), multiple myeloma and acute hematological malignancies, endometriosis, fibrosarcoma, choriocarcinoma, laryngeal carcinomas, Kaposi's sarcoma, Schwannoma, oligodendroglioma, neuroblastomas, rhabdomyosarcoma, osteogenic sarcoma, leiomyosarcoma, and urinary tract carcinomas.

In some embodiments, the cancer is one or more of anorectal cancer, bladder cancer, breast cancer, cervical cancer, colorectal cancer, esophageal cancer, gastric cancer, head & neck cancer, hepatobiliary cancer, leukemia, lung cancer, lymphoma, melanoma, multiple myeloma, ovarian cancer, pancreatic cancer, prostate cancer, renal cancer, thyroid cancer, uterine cancer, or any combination thereof.

In some embodiments, the one or more cancer can be a "high-signal" cancer (defined as cancers with greater than 50% 5-year cancer-specific mortality), such as anorectal, colorectal, esophageal, head & neck, hepatobiliary, lung, ovarian, and pancreatic cancers, as well as lymphoma and multiple myeloma. High-signal cancers tend to be more aggressive and typically have an above-average cell-free nucleic acid concentration in test samples obtained from a patient.

IV.B. Cancer and Treatment Monitoring

In some embodiments, the cancer prediction can be assessed at multiple different time points (e.g., or before or after treatment) to monitor disease progression or to monitor treatment effectiveness (e.g., therapeutic efficacy). For example, the present invention include methods that involve obtaining a first sample (e.g., a first plasma cfDNA sample) from a cancer patient at a first time point, determining a first cancer prediction therefrom (as described herein), obtaining a second test sample (e.g., a second plasma cfDNA sample) from the cancer patient at a second time point, and determining a second cancer prediction therefrom (as described herein).

In certain embodiments, the first time point is before a cancer treatment (e.g., before a resection surgery or a therapeutic intervention), and the second time point is after a cancer treatment (e.g., after a resection surgery or therapeutic intervention), and the classifier is utilized to monitor the effectiveness of the treatment. For example, if the second cancer prediction decreases compared to the first cancer prediction, then the treatment is considered to have been successful. However, if the second cancer prediction increases compared to the first cancer prediction, then the treatment is considered to have not been successful. In other embodiments, both the first and second time points are before a cancer treatment (e.g., before a resection surgery or a therapeutic intervention). In still other embodiments, both the first and the second time points are after a cancer treatment (e.g., after a resection surgery or a therapeutic intervention). In still other embodiments, cfDNA samples may be obtained from a cancer patient at a first and second time point and analyzed. e.g., to monitor cancer progression, to determine if a cancer is in remission (e.g., after treatment), to monitor or detect residual disease or recurrence of disease, or to monitor treatment (e.g., therapeutic) efficacy.

The test samples can be obtained from a cancer patient over any set of time points and analyzed in accordance with the methods of the invention to monitor a cancer state in the patient. In some embodiments, the first and second time points are separated by an amount of time that ranges from about 15 minutes up to about 30 years, such as about 30 minutes, such as about 1, 2, 3, 4, 5, 6, 7, 8, 9, 10, 11, 12, 13, 14, 15, 16, 17, 18, 19, 20, 21, 22, 23, or about 24 hours, such as about 1, 2, 3, 4, 5, 10, 15, 20, 25 or about 30 days, or such as about 1, 2, 3, 4, 5, 6, 7, 8, 9, 10, 11, or 12 months, or such as about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5 or about 30 years. In other embodiments, test samples can be obtained from the patient at least once every 3 months, at least once every 6 months, at least once a year, at least once every 2 years, at least once every 3 years, at least once every 4 years, or at least once every 5 years.

IV.C. Treatment

In still another embodiment, the cancer prediction can be used to make or influence a clinical decision (e.g., diagnosis of cancer, treatment selection, assessment of treatment effectiveness, etc.). For example, in one embodiment, if the cancer prediction (e.g., for cancer or for a particular cancer type) exceeds a threshold, a physician can prescribe an appropriate treatment (e.g., a resection surgery, radiation therapy, chemotherapy, and/or immunotherapy).

A classifier (as described herein) can be used to determine a cancer prediction that a sample feature vector is from a subject that has cancer. In one embodiment, an appropriate treatment (e.g., resection surgery or therapeutic) is prescribed when the cancer prediction exceeds a threshold. For example, in one embodiment, if the cancer prediction is greater than or equal to 60 one or more appropriate treatments are prescribed. In another embodiment, if the cancer prediction is greater than or equal to 65, greater than or equal to 70, greater than or equal to 75, greater than or equal to 80, greater than or equal to 85, greater than or equal to 90, or greater than or equal to 95, one or more appropriate treatments are prescribed. In other embodiments, the cancer prediction can indicate the severity of disease. An appropriate treatment matching the severity of the disease may then be prescribed.

In some embodiments, the treatment is one or more cancer therapeutic agents selected from the group consisting of a chemotherapy agent, a targeted cancer therapy agent, a differentiating therapy agent, a hormone therapy agent, and an immunotherapy agent. For example, the treatment can be one or more chemotherapy agents selected from the group consisting of alkylating agents, antimetabolites, anthracyclines, anti-tumor antibiotics, cytoskeletal disruptors (taxans), topoisomerase inhibitors, mitotic inhibitors, corticosteroids, kinase inhibitors, nucleotide analogs, platinum-based agents and any combination thereof. In some embodiments, the treatment is one or more targeted cancer therapy agents selected from the group consisting of signal transduction inhibitors (e.g. tyrosine kinase and growth factor receptor inhibitors), histone deacetylase (HDAC) inhibitors, retinoic receptor agonists, proteosome inhibitors, angiogenesis inhibitors, and monoclonal antibody conjugates. In some embodiments, the treatment is one or more differentiating therapy agents including retinoids, such as tretinoin, alitretinoin and bexarotene. In some embodiments, the treatment is one or more hormone therapy agents selected from the group consisting of anti-estrogens, aromatase inhibitors, progestins, estrogens, anti-androgens, and GnRH agonists or analogs. In one embodiment, the treatment is one or more immunotherapy agents selected from the group comprising monoclonal antibody therapies such as rituximab (RITUXAN) and alemtuzumab (CAMPATH), non-specific immunotherapies and adjuvants, such as BCG, interleukin-2 (IL-2), and interferon-alfa, immunomodulating drugs, for instance, thalidomide and lenalidomide (REVLIMID). It is within the capabilities of a skilled physician or oncologist to select an appropriate cancer therapeutic agent based on characteristics such as the type of tumor, cancer stage, previous exposure to cancer treatment or therapeutic agent, and other characteristics of the cancer.

V. Example Results of Cancer Classifier

V.A. Sample Collection and Processing

Study design and samples: CCGA (NCT02889978) is a prospective, multi-center, case-control, observational study with longitudinal follow-up. De-identified biospecimens were collected from approximately 15,000 participants from 142 sites. Samples were divided into training (1,785) and test (1,015) sets; samples were selected to ensure a prespecified distribution of cancer types and non-cancers across sites in each cohort, and cancer and non-cancer samples were frequency age-matched by gender.

Whole-genome bisulfite sequencing: cfDNA was isolated from plasma, and whole-genome bisulfite sequencing (WGBS; 30× depth) was employed for analysis of cfDNA. cfDNA was extracted from two tubes of plasma (up to a combined volume of 10 ml) per patient using a modified QIAamp Circulating Nucleic Acid kit (Qiagen; Germantown, MD). Up to 75 ng of plasma cfDNA was subjected to bisulfite conversion using the EZ-96 DNA Methylation Kit (Zymo Research, D5003). Converted cfDNA was used to prepare dual indexed sequencing libraries using Accel-NGS Methyl-Seq DNA library preparation kits (Swift BioSciences; Ann Arbor, MI) and constructed libraries were quantified using KAPA Library Quantification Kit for Illumina Platforms (Kapa Biosystems; Wilmington, MA). Four libraries along with 10% PhiX v3 library (Illumina, FC-110-3001) were pooled and clustered on an Illumina NovaSeq 6000 S2 flow cell followed by 150-bp paired-end sequencing (30×).

For each sample, the WGBS fragment set was reduced to a small subset of fragments having an anomalous methylation pattern. Additionally, hyper or hypomethylated cfDNA fragments were selected. cfDNA fragments selected for having an anomalous methylation pattern and being hyper or hypermethylated, i.e., UFXM. Fragments occurring at high frequency in individuals without cancer, or that have unstable methylation, are unlikely to produce highly discriminatory features for classification of cancer status. We therefore produced a statistical model and a data structure of typical fragments using an independent reference set of 108 non-smoking participants without cancer (age: 58±14 years, 79 [73%] women) (i.e., a reference genome) from the CCGA study. These samples were used to train a Markov-chain model (order 3) estimating the likelihood of a given sequence of CpG methylation statuses within a fragment as described above in Section II.B. This model was demonstrated to be calibrated within the normal fragment range (p-value>0.001) and was used to reject fragments with a p-value from the Markov model as >=0.001 as insufficiently unusual.

As described above, further data reduction step selected only fragments with at least 5 CpGs covered, and average methylation either >0.9 (hyper methylated) or <0.1 (hypomethylated). This procedure resulted in a median (range) of 2,800 (1,500-12,000) UFXM fragments for participants without cancer in training, and a median (range) of 3,000 (1,200-220,000) UFXM fragments for participants with cancer in training. As this data reduction procedure only used reference set data, this stage was only required to be applied to each sample once.

V.B. Genomic Region Modeling with Shallow Neural Networks

Figure 10:
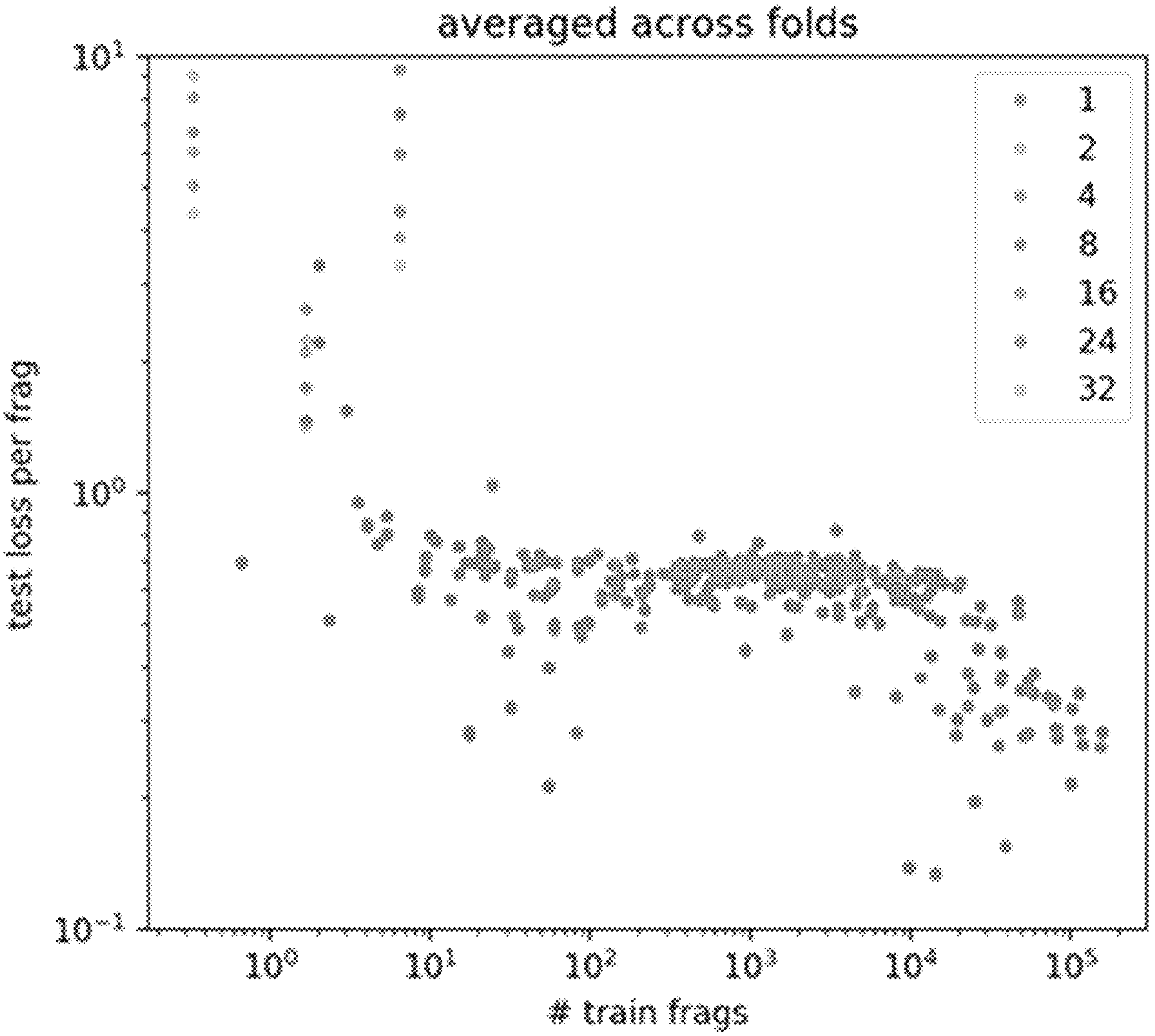
FIG. 10 illustrates the number of nucleic acid fragments in each genomic region used during training of the region models, in an example implementation.

FIG. 10 illustrates the number of nucleic acid fragments in each genomic region used during training of the region models, in an example implementation. A plurality of shallow neural networks having a single hidden layer was trained on a training dataset of cfDNA fragments, and the performances of the trained models are indicated by a measure of loss generated for each nucleic acid methylation fragment in a test dataset (e.g., "test loss per frag"). Each genomic region is represented by a data point in the figure, which illustrates the wide variation in the number of methylation fragments that map to each respective genomic region in the training dataset (e.g., "#train frags"). The figure indicates that model-fitting is challenging in very small regions (e.g., for regions comprising fewer than 10 mapped methylation fragments), suggesting that these regions can be either excluded from consideration or that further optimization is required (e.g., smaller models and/or different numbers of hidden nodes per hidden layer). Various numbers of hidden nodes used in the hidden layer of the various shallow neural networks are indicated in the accompanying legend (e.g., 1, 2, 3, 4, 8, 16, 24, 32).

Figure 11:
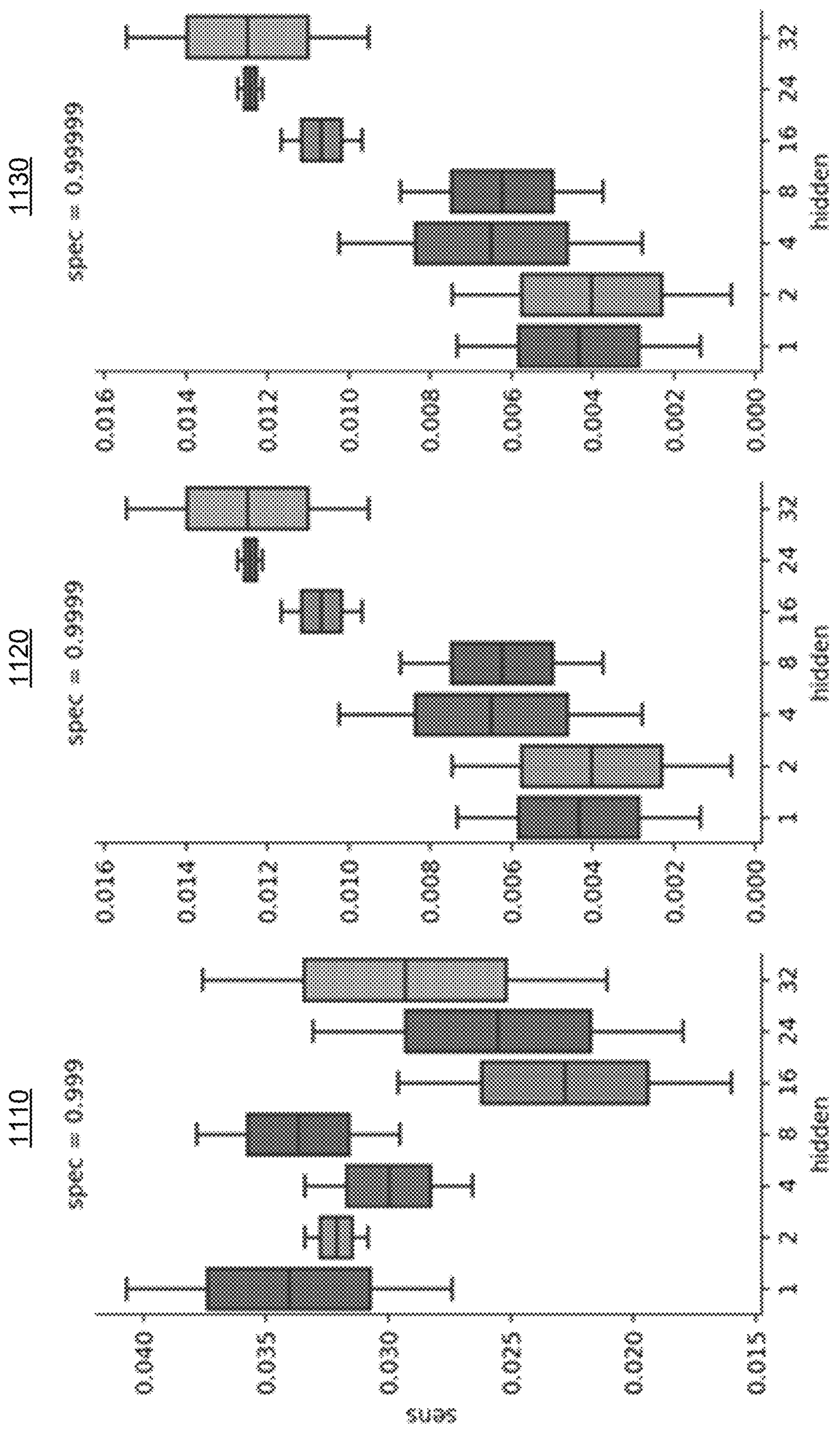
FIG. 11 illustrates the performance of neural networks of varying size and at varying specificity thresholds, each neural network trained with over 30,000 DNA fragments, according to example implementations.

FIG. 11 illustrates the performance of neural networks of varying size and at varying specificity thresholds, each neural network trained with over 30,000 DNA fragments, according to example implementations. The neural networks were trained for binary classification of fragments (e.g., between cancer and non-cancer) with over 30,000 DNA fragments overlapping each region, approximately 200 genomic regions were evaluated. The left panel 1110 illustrates the performance of the neural networks trained to a specificity threshold of 0.999, the middle panel 1120 showing performance when trained to a specificity threshold of 0.9999, and the right panel 1130 showing performance when trained to a specificity threshold 0.99999.

The stringency of the specificity threshold indicates the position of the illustrated output probabilities (e.g., fragment probability fitting) within a probability distribution; thus, high specificity thresholds are used to examine tail probability features. Interestingly, referring to panels 1120 and 1130, models with more hidden nodes provided improved performance in modeling tail probabilities (e.g., features that satisfy high specificity thresholds). Conversely, as illustrated in the left panel 1110, the neural network performance is not observably dependent upon the size of the model. Consequently, neural networks having more hidden nodes do not provide a noticeable advantage for model-fitting over neural networks with less hidden nodes.

The improved resolution of data points at the tail ends of the fragment probability distribution is more noticeable for datasets with large numbers of nucleic acid methylation fragments. This may be due to the saturation of tail features resulting from one or more nonlinear transformations by activation functions (e.g., tanh and/or sigmoid functions). In some such cases, greater numbers of nodes provide greater learning capacity for otherwise saturated features. In some alternative cases, such saturation can be reduced depending on the choice of activation function to be employed in the neural network.

The improved quality of fragment probability fitting in binary classification tasks by larger models is more evident when using regions with high numbers of fragments (e.g., at least 30,000) compared to regions with lower numbers of fragments (e.g., around 10,000).

Figure 12:
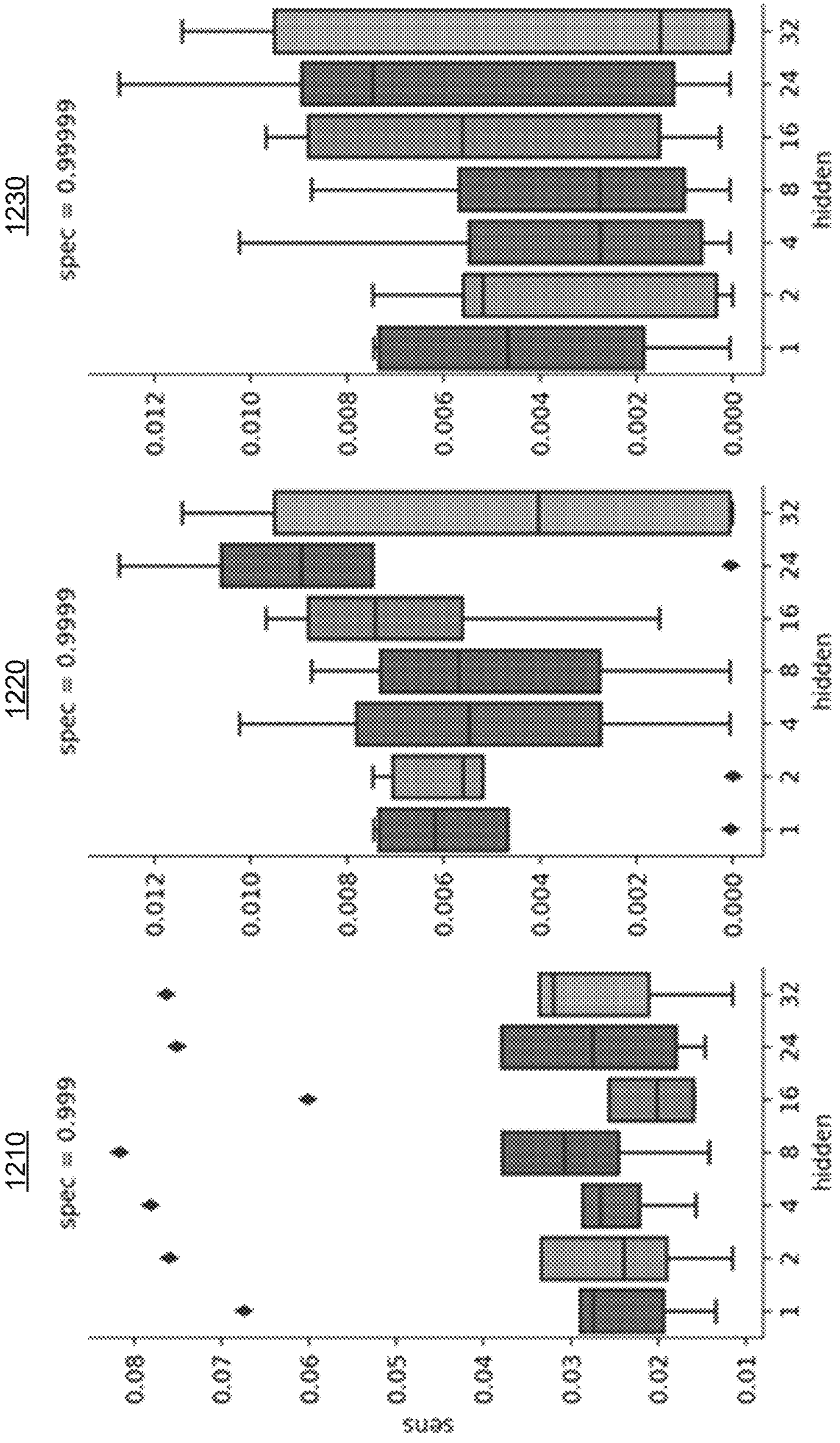
FIG. 12 illustrates the performance of neural networks of varying size and at varying specificity thresholds, each neural network trained with over 10,000 DNA fragments, according to example implementations.

FIG. 12 illustrates the performance of neural networks of varying size and at varying specificity thresholds, each neural network trained with over 10,000 DNA fragments, according to example implementations. As with FIG. 11, the neural networks have a single hidden layer and are trained to generate binary predictions for whether a fragment is derived from a cancer biological sample. Panel 1210 shows performance when trained to a specificity threshold of 0.999; panel 1220 shows performance when trained to a specificity threshold of 0.9999; and panel 1230 shows performance when trained to a specificity threshold of 0.99999. In contrast to FIG. 11, the plots show that an increased number of hidden nodes in the hidden layer of the neural networks do not improve the performance, regardless of the specificity threshold, when training with genomic regions with 10,000 overlapping DNA fragments. FIGS. 11 and 12 illustrate that the optimal size and parameters of shallow neural network models can vary depending on the conditions specific to the data to be fitted, and in some cases will need to be experimentally determined.

Mixture Model Compared with SNN.

Table 1 lists the performance in specificity of a shallow neural network model with fixed or randomized weight initialization compared to a mixture model, at sensitivity thresholds of 95%, 98%, or 99%. All runs were performed using an evaluator configuration asco_2019_1_tm (no tissue). A total of 333 arbitrary regions out of 99931 were excluded for offline hyperparameter tuning.

TABLE 1

Comparison of Performance between Mixture Model and Shallow Neural Network

| | Sens@95 | Sens@98 | Sens@99 |
|---|---|---|---|
| Mixture model 6x3 | 0.588 | 0.555 | 0.532 |
| Shallow NN 6x1 1/8 p < 0.001 (fixed seed) | 0.565 | 0.523 | 0.469 |
| Shallow NN 6x1 1/8 p < 0.001 | 0.56 ± 0.01 | 0.51 ± 0.02 | 0.47 ± 0.04 |

The mixture model and the shallow neural networks were trained using k-fold cross-validation. For example, using 6-fold cross-validation, 6 bins were created from the training data. For each of 6 training runs, one bin was removed as a validation bin and the remaining k−1 bins were used for training. The process was repeated until each bin has been used as a validation bin (e.g., 6×1). The mixture model was further trained by randomly shuffling the data and repeating the process 2 additional times, for a total of 3 cross-validation training runs (e.g., 6×3).

The architecture of the shallow neural networks included either 1 or 8 hidden units (e.g., nodes) in the hidden layer (e.g., ⅛). A p-value threshold of 0.001 was used for selecting anomalous nucleic acid methylation fragments from the dataset prior to input into the shallow neural network models for training.

An initial SNN run using fixed seed weight initialization was performed as a baseline for statistical comparison with subsequent runs using randomized weight initialization.

Fixed seed describes how the weights were initialized. For example, for fixed seed initialization, weights are initialized using a predetermined set of values selected from a particular random distribution using a truncated normal distribution. Thus, weights initialized using fixed seed initialization will be random but have a small magnitude close to zero for optimal backpropagation.

Subsequent (e.g., not fixed seed) SNN runs were performed using randomized weight initialization. Multiple runs and the estimated range of the performance following multiple runs are listed in Table 1, where the range shows the variation between runs. The results presented in Table 1 indicate that the performance of a shallow neural network is comparable to the performance of a mixture model.

V.C. Genomic Region Modeling with Pooled-End-to-End Training

Figure 13:
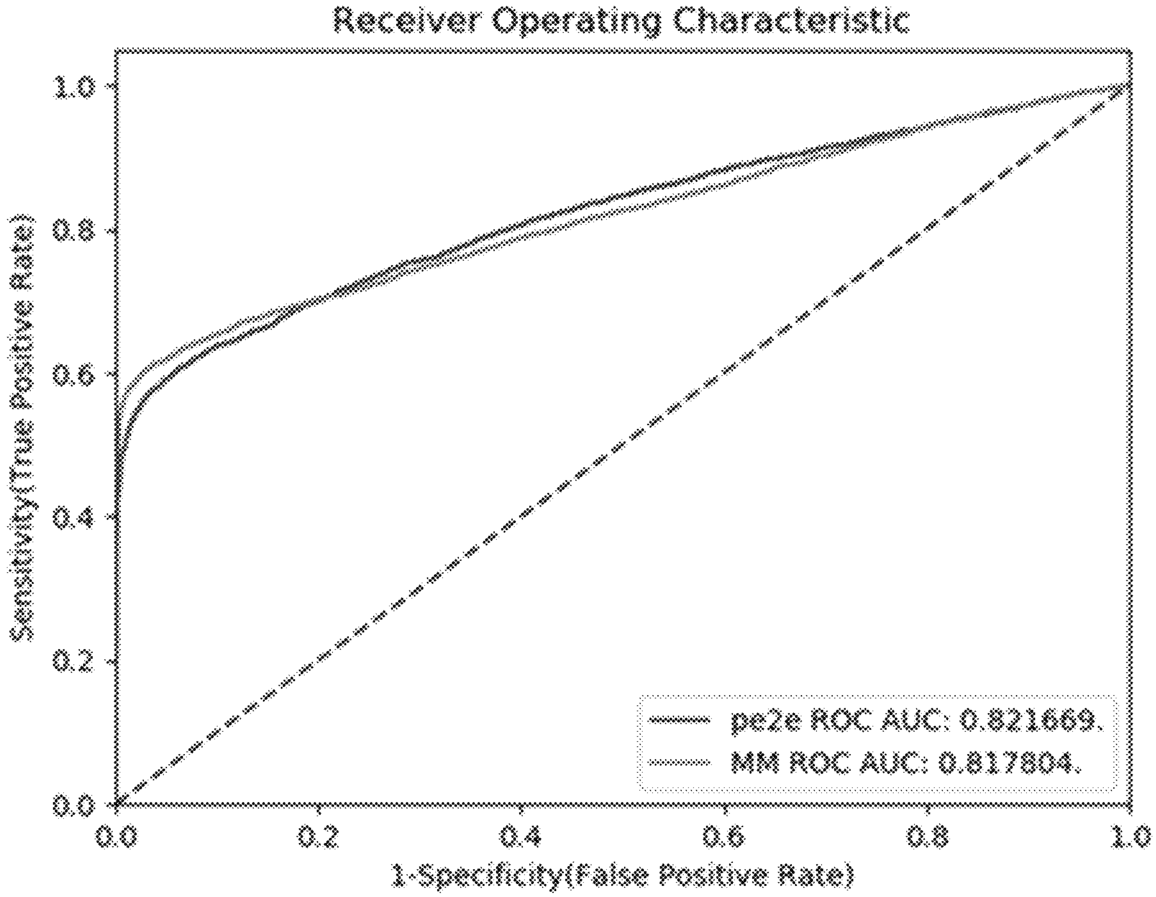
FIG. 13 illustrates the performance of a cancer classification process implementing pooled-end-to-end training, according to an example implementation.

FIG. 13 illustrates the performance of a cancer classification process implementing pooled-end-to-end training, according to an example implementation. According to this implementation, a cancer classifier was trained concurrently with a featurization module, region models, and a methylation embedding model. Each region model is configured to generate a region embedding for an input methylation embedding of a DNA fragment overlapping the genomic region, for which the region model is trained. The featurization module is configured to perform two pooling steps-a first pooling step to pool region embeddings to generate an aggregate region vector for each genomic region, and a second pooling step to pool aggregate region vectors of the genomic regions into a feature vector (e.g., as described in FIGS. 7 and 8). The cancer classifier was evaluated against a holdout set and performed with an overall area under the curve (also referred to as "AUC") of 0.821669, which was a slight improvement over a leading cancer classifier. As a general note, AUC of 0.5 represents a model that effectively has no discrimination capacity between a positive label and a negative label, and an AUC of 1 represents a model that has perfect accuracy in discriminating between the positive label and the negative label.

Figure 14A:
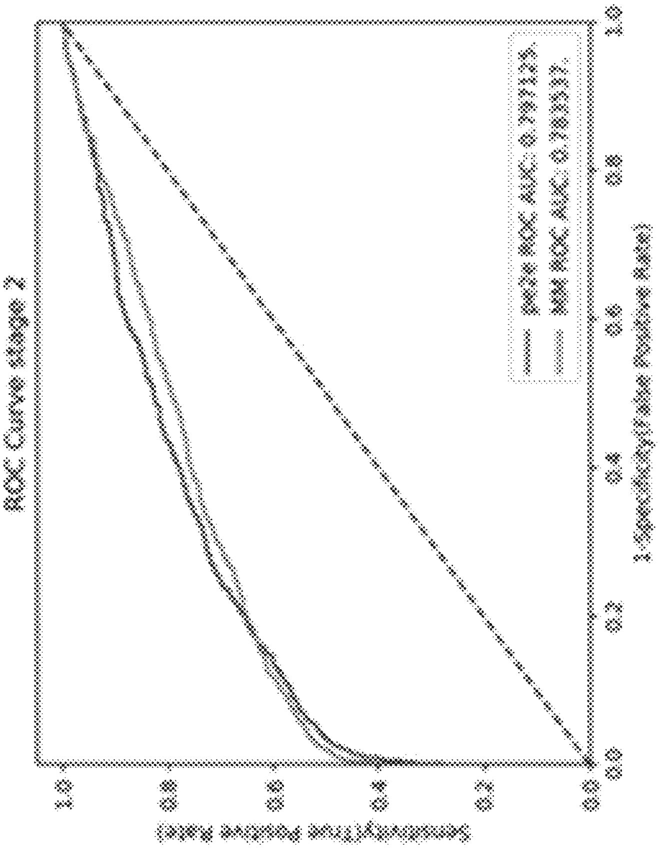
FIGS. 14A and 14B illustrate the performance of the cancer classification implementing pooled-end-to-end training, at various stages of cancer, according to an example implementation.
Figure 14A:
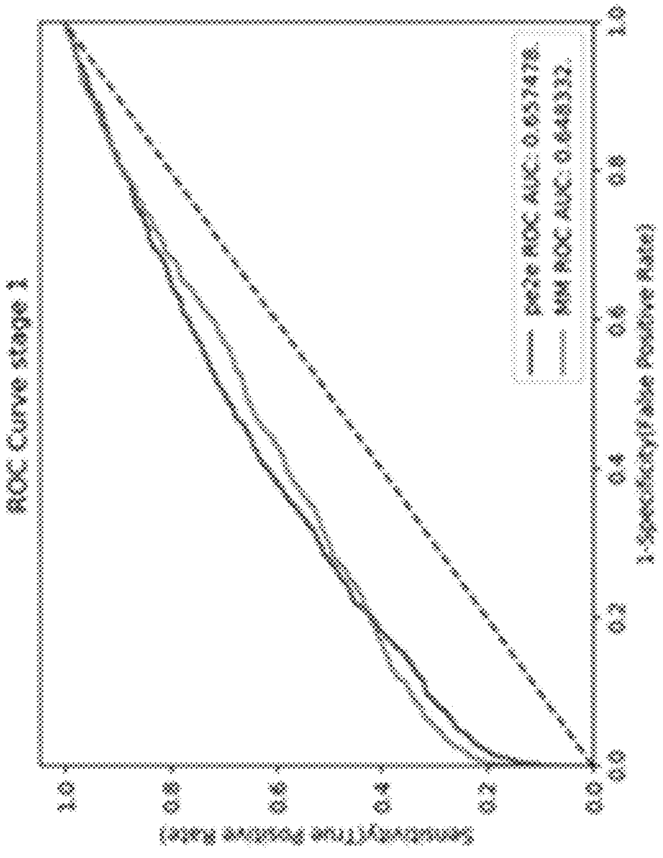
Figure 14B:
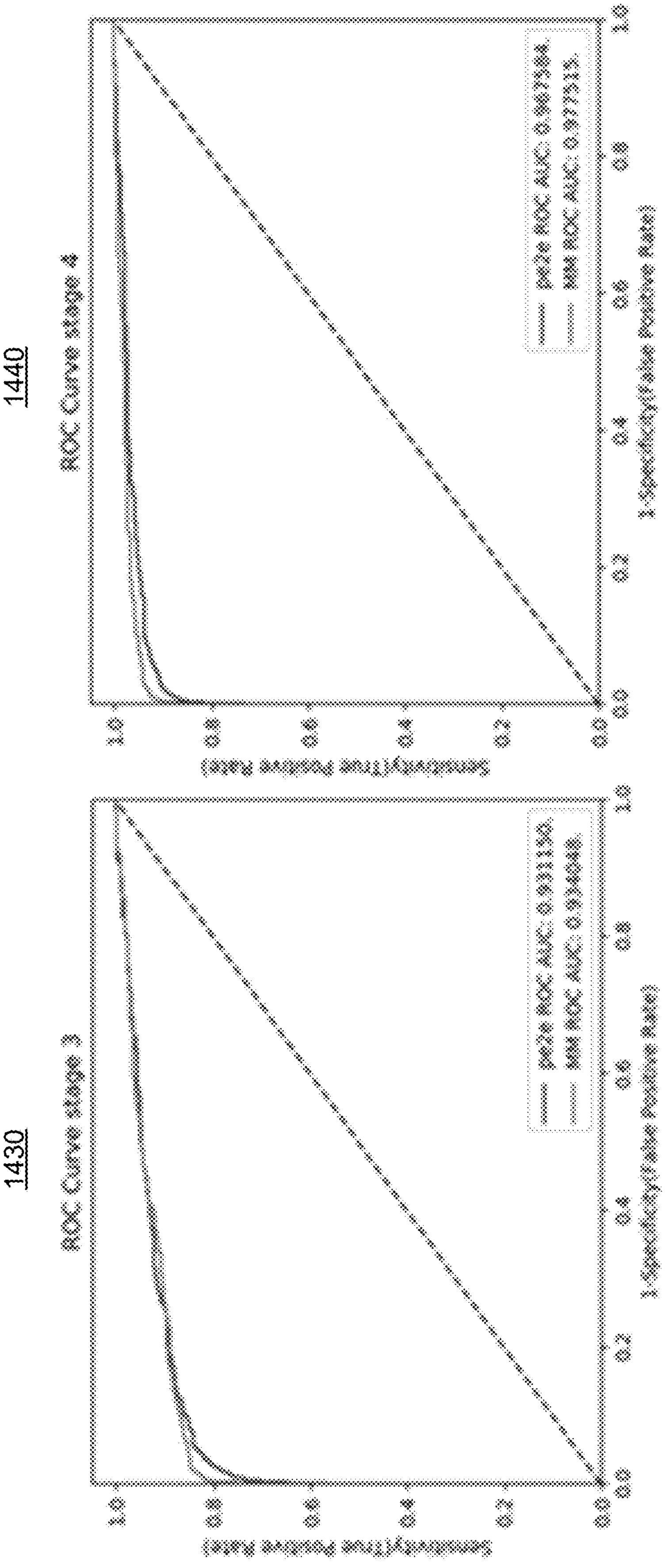

FIGS. 14A and 14B illustrate the performance of the cancer classification implementing pooled-end-to-end training, at various stages of cancer, according to the example implementation in FIG. 13. Holdout sets for each stage of cancer were used to evaluate the performance over the various stages of cancer. The pooled-end-to-end cancer classifier is labeled as "pe2e" in the following graphs. Graph 1410 shows AUC of 0.657478 for stage 1 cancer prediction. Graph 1420 shows AUC of 0.797125 for stage 2 cancer prediction. Graph 1430 shows AUC of 0.931150 for stage 3 cancer prediction. Graph 1440 shows AUC of 0.967584 for stage 4 cancer prediction. Overall, the cancer classifier implementing pooled-end-to-end training performed comparably with the leading cancer classifier. Noticeably, the cancer classifier's prediction steadily improved over later and later stages of cancer. The cancer classifier performed slightly better in stages 1 and 2 compared to the leading classifier, but performed slightly worse in stages 3 and 4 compared to the leading classifier.

VI. Claimable Subject Matter

In one aspect, a method for detecting cancer comprises receiving sequencing data for a biological sample comprising a plurality of cfDNA fragments, each cfDNA fragment overlapping at least one genomic region of a plurality of genomic regions; for each cfDNA fragment of the biological sample, determining a first score for the genomic region that the cfDNA fragment overlaps, the first score for a genomic region determined by inputting the cfDNA fragment into a neural network trained for the genomic region, the neural network configured to generate the first score representative of a likelihood that the cfDNA fragment is derived from a cancer biological sample; generating a feature vector for the biological sample, each feature of the feature vector corresponding to a genomic region of the plurality of genomic regions and generated according to a count of cfDNA fragments having a score for the genomic region above a threshold score; and inputting the feature vector into a trained model to generate a cancer prediction for the biological sample.

In another aspect, a method for detecting cancer comprises receiving sequencing data for a biological sample comprising a plurality of cfDNA fragments, each cfDNA fragment overlapping at least one genomic region of a plurality of genomic regions; for each cfDNA fragment of the biological sample, generating a methylation embedding by inputting the cfDNA fragment into a trained embedding model, the trained embedding model configured to generate a methylation embedding based on an input cfDNA fragment; for each cfDNA fragment of the biological sample, generating a region embedding for the genomic region that the cfDNA fragment overlaps, the region embedding for a genomic region determined by inputting the methylation embedding of the cfDNA fragment into a region model trained for the genomic region, the region model configured to generate a region embedding based on an input methylation embedding; for each genomic region, determining an aggregate region vector by pooling one or more region embeddings of one or more cfDNA fragments overlapping the genomic region; determining a feature vector by pooling the aggregate region vectors of the genomic regions; and inputting the feature vector into a classification model to generate a cancer prediction for the biological sample.

In yet another aspect, genomic datasets can be obtained for a plurality of training subjects, each dataset having a cancer state label (e.g., cancer and/or non-cancer) and nucleic acid methylation fragments. Each nucleic acid methylation fragment can have a methylation pattern of CpG methylation states, determined by methylation sequencing of nucleic acids in a biological sample. Untrained neural networks (e.g., genomic region model and/or model provided by featurization module) can be trained for a plurality of genomic regions using the genomic datasets. Each untrained neural network can independently correspond to a respective genomic region, can comprise a plurality of weights, and score nucleic acid methylation fragments that map to the genomic region. The training can update the weights (e.g., using backpropagation) based on a comparison of the scores to the cancer state label of the training subjects originating the nucleic acid methylation fragments (e.g., determined using a loss function). Features (or feature vectors) can be identified for each genomic region by using the trained neural network to score nucleic acid methylation fragments mapping to the genomic region. For example, a score obtained by a trained neural network comprises a probability that the respective nucleic acid methylation fragment originates from a training subject with a particular cancer state label. Features can comprise one or more counts of nucleic acid methylation fragments that satisfy a probability threshold for the respective cancer state label (e.g., a ratio of the count of nucleic acid methylation fragments that satisfy a probability threshold for cancer over the count of nucleic acid methylation fragments that satisfy a probability threshold for non-cancer).

Features obtained using the systems and methods disclosed herein can be used as input for downstream supervised models (e.g., cancer classifier) for further classification of cancer states, including cancer type, stage, or tissue-of-origin. Such features can increase the discriminatory power of downstream classifiers (e.g., supervised models) by selecting highly aberrant nucleic acid methylation fragments for input (e.g., fragments scored with a high probability for one or more cancer states), while removing less informative fragments that fail to satisfy one or more probability thresholds for one or more respective cancer states. The method disclosed herein can thus improve upon the selection of nucleic acid methylation fragments from a plurality of genomic datasets for input into downstream classifiers, and further improve the efficiency and performance of training and using a supervised model to determine a cancer state of a subject.

Another aspect of the present disclosure provides a method for obtaining a plurality of features for determining a cancer state of a subject. The method can be performed at a computer system comprising at least one processor and a memory storing at least one program comprising instructions for execution by the at least one processor. The method can comprise obtaining a plurality of genomic datasets. Each respective genomic dataset in the plurality of genomic datasets can be for a respective training subject in a plurality of training subjects. Each respective genomic dataset can comprise (e.g., in electronic form) a corresponding label for the cancer state of the respective training subject and a corresponding plurality of nucleic acid methylation fragments. Each respective nucleic acid methylation fragment in the corresponding plurality of nucleic acid methylation fragments can comprise a corresponding methylation pattern comprising a methylation state of each CpG site in a corresponding plurality of CpG sites of the respective nucleic acid methylation fragment. The corresponding plurality of nucleic acid methylation fragments can be determined by methylation sequencing of nucleic acids in a biological sample obtained from the respective training subject.

The method can further comprise training, for each respective genomic region in a plurality of genomic regions and based on the plurality of genomic datasets from each training subject of the plurality of training subjects, a corresponding untrained neural network in a plurality of untrained neural networks, thus obtaining a corresponding trained neural network in a plurality of trained neural networks. The corresponding untrained neural network (and the resulting corresponding trained neural network) can independently correspond to the respective genomic region. The corresponding untrained neural network can comprise a corresponding plurality of weights. The corresponding untrained neural network can score respective nucleic acid methylation fragments, in each corresponding plurality of nucleic acid methylation fragments, that map to the respective genomic region represented by the corresponding untrained neural network thus obtaining a corresponding plurality of training scores. The training can update a corresponding value of each weight in the corresponding plurality of weights in the corresponding untrained neural network based on a comparison of the corresponding plurality of training scores to the corresponding label for the cancer state of the respective training subjects originating the respective nucleic acid methylation fragments (e.g., through back-propagation techniques) thus obtaining the corresponding trained neural network.

The method can further comprise performing feature identification (e.g., generating a feature vector), for each respective genomic region in the plurality of genomic regions. For each training subject in the plurality of training subjects, a respective feature of the genomic region for the respective training subject can be obtained by using the trained neural network that corresponds to the respective genomic region to score respective nucleic acid methylation fragments in the plurality of nucleic acid methylation fragments corresponding to the respective training subject that map to the respective genomic region for the cancer state, thereby obtaining a plurality of features.

In some embodiments, the corresponding trained neural network computes a separate probability for each cancer state in a plurality of cancer states as well as the noncancer state upon inputting the respective nucleic acid methylation fragment into the corresponding trained neural network. In some embodiments, the plurality of cancer states comprises adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, and/or leukemia.

In some embodiments, the training is performed through K-fold cross-validation. In some embodiments, the cancer state is absence or presence of cancer and a first subset of the plurality of training subjects have cancer and a second subset of the plurality of training subjects are free of cancer. In some embodiments, the at least one program further comprises instructions for training a downstream supervised model using, for each respective genomic region in the plurality of genomic regions, each respective feature of the respective genomic regions computed by the feature identification (or feature module) and the corresponding label for the cancer state of the respective training subject associated with the respective feature.

In some such embodiments, the training, the feature identification, and the training the downstream supervised model are performed in a combined training that jointly trains the plurality of neural networks and the downstream supervised model. In some such embodiments, the downstream model accepts as input a vector, where the vector is associated with a respective training subject in the plurality of training subjects and each element of the vector is a respective feature of a different genomic region in the plurality of genomic regions computed by the feature identification using respective nucleic acid methylation fragments in the plurality of nucleic acid methylation fragments corresponding to the respective training subject that map to the different genomic region.

In some such embodiments, the at least one program further comprises instructions for obtaining a plurality of test nucleic acid methylation fragments. Each respective test nucleic acid methylation fragment in the corresponding plurality of test nucleic acid methylation fragments comprises a corresponding methylation pattern comprising a methylation state of each CpG site in a corresponding plurality of CpG sites of the respective test nucleic acid methylation fragment, where the plurality of test nucleic acid methylation fragments is determined by a methylation sequencing of nucleic acids in a biological sample obtained from the test subject. The at least one program further comprises instructions for performing test feature identification, for each respective genomic region in the plurality of genomic regions. A respective test feature of the genomic region for the test subject is obtained by using the trained neural network that corresponds to the respective genomic region to score respective test nucleic acid methylation fragments in the plurality of test nucleic acid methylation fragments corresponding to the test subject that map to the respective genomic region for the cancer state, thereby obtaining a plurality of test features that includes a test feature for each genomic region in the plurality of genomic regions. The at least one program further comprises instructions for applying the plurality of test features to the downstream supervised model to determine whether the test subject has the cancer state.

In some embodiments, the plurality of genomic regions comprises between 100 and 100,000 genomic regions. In some embodiments, the plurality of genomic regions comprises between 500 and 2,000 genomic regions. In some embodiments, an average length of a corresponding plurality of nucleic acid methylation fragments is between 140 and 280 nucleotides.

In some embodiments, the respective nucleic acid methylation fragment fails to satisfy a selection criterion in the one or more selection criteria when an output p-value provided by a trained Markov model, responsive to input of the methylation pattern of the nucleic acid methylation fragment, fails to satisfy a p-value threshold. The trained Markov model can be trained, at least in part, based upon evaluation of a methylation state of each CpG site in the corresponding plurality of CpG sites of the respective nucleic acid methylation fragment across those nucleic acid methylation fragments, in a healthy noncancer cohort dataset, that have the corresponding plurality of CpG sites. In some embodiments, the p-value threshold is between 0.01 and 0.10. In some embodiments, the p-value threshold is between 0.03 and 0.06. In some embodiments, the respective nucleic acid methylation fragment fails to satisfy a selection criterion in the one or more selection criteria when the respective nucleic acid methylation fragment has less than a threshold number of CpG sites. In some embodiments, the threshold number of CpG sites is 4, 5, 6, 7, 8, 9, or 10.

In some embodiments, the respective nucleic acid methylation fragment fails to satisfy a selection criterion in the one or more selection criteria when a genomic start position and a genomic end position of the respective nucleic acid methylation fragment indicates that the respective nucleic acid methylation fragment represents less than a threshold number of nucleotides in a human genome reference sequence. In some embodiments, the threshold number of residues is a fixed value between 20 and 90. In some embodiments, the filtering removes a nucleic acid methylation fragment in the corresponding plurality of nucleic acid methylation fragments that has the same corresponding methylation pattern and the same corresponding genomic start position and genomic end position as another nucleic acid methylation fragment in the corresponding plurality of nucleic acid methylation fragments.

In some embodiments, the method further comprises, prior to training the neural network, removing a subset of methylation fragments from the plurality of methylation fragments based on mutual information filtering of the respective methylation fragments against the cancer state across the plurality of training subjects.

In some embodiments, the methylation state of a CpG site in the corresponding plurality of CpG sites in the respective nucleic acid methylation fragment is methylated when the CpG site is determined by the methylation sequencing to be methylated, and unmethylated when the CpG site is determined by the methylation sequencing to not be methylated. In some embodiments, the methylation state of each CpG site in the corresponding plurality of CpG sites for a respective nucleic acid methylation fragment is one-hot encoded in a corresponding two-dimensional vector that is applied to the corresponding untrained neural network that corresponds to the respective genomic region that the respective nucleic acid methylation fragment maps to in the training.

In some embodiments, the cancer state is absence or presence of cancer. In some embodiments, the cancer state is absence or presence of a type of cancer. In some embodiments, the type of cancer (or cancer type, specified cancer) comprises adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, leukemia, or a combination thereof. In some embodiments, the cancer state is a stage of a specified cancer.

In some embodiments, the methylation sequencing of nucleic acids in the biological sample obtained from the respective training subject is methylation sequencing of cell-free nucleic acids in the biological sample. In some embodiments, the biological sample is a blood sample. In some embodiments, the respective biological sample of a training subject in the plurality of training subjects is homogenous for the cancer state. In some embodiments, the respective biological sample of a training subject in the plurality of training subjects is a tumor sample that is homogenous for the cancer state.

In some embodiments, the one or more corresponding neural network outputs of a corresponding trained neural network in the plurality of trained neural networks is a single neural network output that provides a probability that the training subject has the cancer state. In some embodiments, the one or more corresponding neural network outputs of a corresponding trained neural network in the plurality of trained neural networks is a plurality of neural network outputs, wherein each neural network output in the plurality of neural network outputs provides a probability that the training subject has a corresponding cancer type in a plurality of cancer types.

In some embodiments, a multi-genomic region consists of a subset of the plurality of genomic regions, and the performing feature identification makes use of a multi-genomic region neural network that accepts, as input, an output of each trained neural network corresponding to a genomic region in the subset of the plurality of genomic regions in order to obtain a respective feature of each genomic region in the subset of the plurality of genomic regions for the respective training subject or a single feature for the subset of the plurality of genomic regions.

In some embodiments, the methylation sequencing of nucleic acids in the biological sample obtained from the respective training subject is methylation sequencing of cell-free nucleic acids in the biological sample. In some such embodiments, the method further comprises training a corresponding untrained neural network in the plurality of trained neural networks, at least in part, using methylation data for nucleic acid methylation fragments obtained from one or more tumor samples representative of the cancer state.

Another aspect of the present disclosure provides a method for determining a cancer state of a subject. The method can be performed at a computer system comprising at least one processor and a memory storing at least one program comprising instructions for execution by the at least one processor. The method can comprise obtaining, in electronic form, a plurality of nucleic acid methylation fragments. Each respective nucleic acid methylation fragment in the plurality of nucleic acid methylation fragments can comprise a corresponding methylation pattern comprising a methylation state of each CpG site in a corresponding plurality of CpG sites of the respective nucleic acid methylation fragment. The plurality of nucleic acid methylation fragments can be determined by a methylation sequencing of nucleic acids in a biological sample obtained from the subject.

The method can further comprise performing feature identification, for each respective genomic region in a plurality of genomic regions. A respective feature of the genomic region for the subject can be obtained by using a trained neural network in a plurality of trained neural networks that corresponds to the respective genomic region to score respective nucleic acid methylation fragments in the plurality of nucleic acid methylation fragments that map to the respective genomic region for the cancer state, thereby obtaining a plurality of features. Each respective feature in the plurality of features can be for a corresponding genomic region in the plurality of genomic regions. The method can further comprise, responsive to inputting the plurality of features to a downstream supervised model, obtaining a determination as to whether the test subject has the cancer state as output of the downstream supervised model.

Another aspect of the present disclosure provides a method for obtaining a plurality of features for determining a cancer state of a subject, the method comprising: at a computer system comprising at least one processor and a memory storing at least one program for execution by the at least one processor, the at least one program comprising instructions for: A) obtaining a plurality of genotypic datasets, each respective genotypic dataset in the plurality of genotypic datasets for a respective training subject in a plurality of training subjects, wherein the respective genotypic dataset comprises, in electronic form, (i) a corresponding label for the cancer state of the respective training subject and (ii) a corresponding plurality of nucleic acid methylation fragments, wherein each respective nucleic acid methylation fragment in the corresponding plurality of nucleic acid methylation fragments comprises a corresponding methylation pattern comprising a methylation state of each CpG site in a corresponding plurality of CpG sites of the respective nucleic acid methylation fragment, and wherein the corresponding plurality of nucleic acid methylation fragments is determined by a methylation sequencing of nucleic acids in a biological sample obtained from the respective training subject; B) training, for each respective genomic region in a plurality of genomic regions and based on the plurality of genotypic datasets from each training subject of the plurality of training subjects, a corresponding untrained neural network in a plurality of untrained neural networks, thereby obtaining a corresponding trained neural network in a plurality of trained neural networks, wherein: the corresponding untrained neural network independently corresponds to the respective genomic region, the corresponding untrained neural network comprises a corresponding plurality of weights, the corresponding untrained neural network scores respective nucleic acid methylation fragments, in each corresponding plurality of nucleic acid methylation fragments, that map to the respective genomic region thereby obtaining a corresponding plurality of training scores, the training updates a corresponding value of each weight in the corresponding plurality of weights in the corresponding untrained neural network based on a comparison of the corresponding plurality of training scores to the corresponding label for the cancer state of the respective training subjects originating the respective nucleic acid methylation fragments thereby obtaining the corresponding trained neural network; and C) performing feature identification by, for each respective genomic region in the plurality of genomic regions, for each training subject in the plurality of training subjects: obtaining a respective feature of the genomic region for the respective training subject by using the trained neural network that corresponds to the respective genomic region to score respective nucleic acid methylation fragments in the plurality of nucleic acid methylation fragments corresponding to the respective training subject that map to the respective genomic region for the cancer state, thereby obtaining a plurality of features.

In some embodiments, the respective feature of the genomic region for the respective training subject is a count of respective nucleic acid methylation fragments in the plurality of nucleic acid methylation fragments corresponding to the respective training subject that map to the respective genomic region for the cancer state that satisfy the condition: log((P(cancer state))/(P(noncancer state)))> threshold, wherein: P(cancer state) is a probability that the respective nucleic acid methylation fragment is associated with the cancer state, wherein the probability is provided by the corresponding trained neural network that corresponds to the respective genomic region upon inputting the respective nucleic acid methylation fragment into the corresponding trained neural network, P(noncancer state)=1−P(cancer state), threshold is a fixed value, and the corresponding trained neural network computes only P(cancer state).

In some embodiments, the respective feature of the genomic region for the respective training subject is a count of respective nucleic acid methylation fragments in the plurality of nucleic acid methylation fragments corresponding to the respective training subject that map to the respective genomic region for the cancer state that satisfy the condition: log((P(cancer state))/(P(noncancer state))) >threshold, wherein: P(cancer state) is a first probability that the respective nucleic acid methylation fragment is associated with the cancer state, wherein the first probability is provided by the corresponding trained neural network that corresponds to the respective genomic region upon inputting the respective nucleic acid methylation fragment into the corresponding trained neural network, P(noncancer state) is a second probability that the respective nucleic acid methylation fragment is associated with the noncancer state, wherein the second probability is provided by the corresponding trained neural network that corresponds to the respective genomic region upon inputting the respective nucleic acid methylation fragment into the corresponding trained neural network, and threshold is a fixed value.

In some embodiments, the corresponding trained neural network computes a separate probability for each cancer state in a plurality of cancer states as well as the noncancer state upon inputting the respective nucleic acid methylation fragment into the corresponding trained neural network.

In some embodiments, the plurality of cancer states comprises adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, and/or leukemia.

In some embodiments, the B) training is performed through K-fold cross-validation.

In some embodiments, the cancer state is absence or presence of cancer and a first subset of the plurality of training subjects have cancer and a second subset of the plurality of training subjects are free of cancer.

In some embodiments, the at least one program further comprises instructions for: D) training a downstream supervised model using, for each respective genomic region in the plurality of genomic regions each respective feature of the respective genomic regions computed by C) and the corresponding label for the cancer state of the respective training subject associated with the respective feature.

In some embodiments, the B) training, the C) performing, and the D) training are performed in a combined training that jointly trains the plurality of neural networks and the downstream supervised model.

In some embodiments, the downstream model accepts as input a vector, wherein the vector is associated with a respective training subject in the plurality of training subjects and each element of the vector is a respective feature of a different genomic region in the plurality of genomic regions computed by the C) performing using respective nucleic acid methylation fragments in the plurality of nucleic acid methylation fragments corresponding to the respective training subject that map to the different genomic region.

In some embodiments, the downstream supervised model is logistic regression.

In some embodiments, the downstream supervised model is a neural network algorithm, a support vector machine algorithm, a Naive Bayes algorithm, a nearest neighbor algorithm, a boosted trees algorithm, a random forest algorithm, a decision tree algorithm, a multinomial logistic regression algorithm, a linear model, or a linear regression algorithm.

In some embodiments, the at least one program further comprises instructions for: E) obtaining a plurality of test nucleic acid methylation fragments, wherein each respective test nucleic acid methylation fragment in the corresponding plurality of test nucleic acid methylation fragments comprises a corresponding methylation pattern comprising a methylation state of each CpG site in a corresponding plurality of CpG sites of the respective test nucleic acid methylation fragment, and wherein the plurality of test nucleic acid methylation fragments is determined by a methylation sequencing of nucleic acids in a biological sample obtained from the test subject; F) performing test feature identification by, for each respective genomic region in the plurality of genomic regions, obtaining a respective test feature of the genomic region for the test subject by using the trained neural network that corresponds to the respective genomic region to score respective test nucleic acid methylation fragments in the plurality of test nucleic acid methylation fragments corresponding to the test subject that map to the respective genomic region for the cancer state, thereby obtaining a plurality of test features that includes a test feature for each genomic region in the plurality of genomic regions; and G) applying the plurality of test features to the downstream supervised model to determine whether the test subject has the cancer state.

In some embodiments, the corresponding plurality of nucleic acid methylation fragments comprises one thousand or more, ten thousand or more, 100 thousand or more, one million or more, ten million or more, 100 million or more, 500 million or more, one billion or more, two billion or more, three billion or more, four billion or more, five billion or more, six billion or more, seven billion or more, eight billion or more, nine billion or more, or 10 billion or more nucleic acid methylation fragments.

In some embodiments, there are more than 10,000 CpG sites, more than 25,000 CpG sites, more than 50,000 CpG sites, or more than 80,000 CpG sites across the plurality of genomic regions.

In some embodiments, a first genomic region consists of a first number of CpG sites and a second genomic region in the plurality of genomic regions consists of a second number of CpG sites that is different than the first number of CpG sites.

In some embodiments, the plurality of genomic regions comprises between 100 and 100,000 genomic regions.

In some embodiments, the plurality of genomic regions comprises between 500 and 2,000 genomic regions.

In some embodiments, an average length of a corresponding plurality of nucleic acid methylation fragments is between 140 and 280 nucleotides.

In some embodiments, each genomic region in the plurality of genomic regions represents between 500 base pairs and 10,000 base pairs of a human genome reference sequence.

In some embodiments, each genomic region in the plurality of genomic regions represents between 500 base pairs and 2,000 base pairs of a human genome reference sequence.

In some embodiments, each genomic region in the plurality of genomic regions represents a different portion of a human genome reference sequence.

In some embodiments 3, the A) obtaining further comprises filtering the corresponding plurality of nucleic acid methylation fragments by removing, from the corresponding plurality of nucleic acid methylation fragments, each respective nucleic acid methylation fragment that fails to satisfy one or more selection criteria.

In some embodiments, the respective nucleic acid methylation fragment fails to satisfy a selection criterion in the one or more selection criteria when the corresponding methylation pattern of the respective nucleic acid methylation fragment has an output p-value that fails to satisfy a p-value threshold, and the output p-value of the respective nucleic acid methylation fragment is determined, at least in part, based upon a comparison of the corresponding methylation pattern of the respective nucleic acid methylation fragment to a corresponding distribution of methylation patterns of those nucleic acid methylation fragments in a healthy noncancer cohort dataset that have the corresponding plurality of CpG sites of the respective nucleic acid methylation fragment.

In some embodiments, the respective nucleic acid methylation fragment fails to satisfy a selection criterion in the one or more selection criteria when an output p-value provided by a trained Markov model, responsive to input of the methylation pattern of the nucleic acid methylation fragment, fails to satisfy a p-value threshold, and the trained Markov model is trained, at least in part, based upon evaluation of a methylation state of each CpG site in the corresponding plurality of CpG sites of the respective nucleic acid methylation fragment across those nucleic acid methylation fragments in a healthy noncancer cohort dataset that have the corresponding plurality of CpG sites.

In some embodiments, the p-value threshold is between 0.01 and 0.10.

In some embodiments, the p-value threshold is between 0.03 and 0.06.

In some embodiments, the respective nucleic acid methylation fragment fails to satisfy a selection criterion in the one or more selection criteria when the respective nucleic acid methylation fragment has less than a threshold number of CpG sites.

In some embodiments, the threshold number of CpG sites is 4, 5, 6, 7, 8, 9, or 10.

In some embodiments, the respective nucleic acid methylation fragment fails to satisfy a selection criterion in the one or more selection criteria when a genomic start position and a genomic end position of the respective nucleic acid methylation fragment indicates that the respective nucleic acid methylation fragment represents less than a threshold number of nucleotides in a human genome reference sequence.

In some embodiments, the threshold number of residues is a fixed value between 20 and 90.

In some embodiments, the filtering removes a nucleic acid methylation fragment in the corresponding plurality of nucleic acid methylation fragments that has the same corresponding methylation pattern and the same corresponding genomic start position and genomic end position as another nucleic acid methylation fragment in the corresponding plurality of nucleic acid methylation fragments.

In some embodiments, the method further comprises, prior to the training B), removing a subset of methylation fragments from the plurality of methylation fragments based on mutual information filtering of the respective methylation fragments against the cancer state across the plurality of training subjects.

In some embodiments, the methylation state of a CpG site in the corresponding plurality of CpG sites in the respective nucleic acid methylation fragment is: methylated when the CpG site is determined by the methylation sequencing to be methylated, and unmethylated when the CpG site is determined by the methylation sequencing to not be methylated.

In some embodiments, the methylation state of each CpG site in the corresponding plurality of CpG sites for a respective nucleic acid methylation fragment is one-hot encoded in a corresponding two-dimensional vector that is applied to the corresponding untrained neural network that corresponds to the respective genomic region that the respective nucleic acid methylation fragment maps to in the training B).

In some embodiments, the methylation sequencing is i) whole-genome methylation sequencing or ii) targeted DNA methylation sequencing using a plurality of nucleic acid probes.

In some embodiments, the methylation sequencing detects one or more 5-methylcytosine (5mC) and/or 5-hydroxymethylcytosine (5hmC) in respective nucleic acid methylation fragments.

In some embodiments, the methylation sequencing comprises conversion of one or more unmethylated cytosines or one or more methylated cytosines, in respective nucleic acid methylation fragments, to a corresponding one or more uracils.

In some embodiments, the one or more uracils are detected during the methylation sequencing as one or more corresponding thymines.

In some embodiments, the conversion of one or more unmethylated cytosines or one or more methylated cytosines comprises a chemical conversion, an enzymatic conversion, or combinations thereof.

In some embodiments, the cancer state is absence or presence of cancer.

In some embodiments, the cancer state is absence or presence of a type of cancer.

In some embodiments, the type of cancer is adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, leukemia, or a combination thereof.

In some embodiments, the cancer state is a stage of a specified cancer.

In some embodiments, the specified cancer is adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, leukemia, or a combination thereof.

In some embodiments, the methylation sequencing of nucleic acids in the biological sample obtained from the respective training subject is methylation sequencing of cell-free nucleic acids in the biological sample.

In some embodiments, the biological sample is a blood sample.

In some embodiments, the biological sample comprises blood, whole blood, plasma, serum, urine, cerebrospinal fluid, fecal, saliva, sweat, tears, pleural fluid, pericardial fluid, or peritoneal fluid of the respective training subject.

In some embodiments, the respective biological sample of a training subject in the plurality of training subjects is homogenous for the cancer state.

In some embodiments, the respective biological sample of a training subject in the plurality of training subjects is a tumor sample that is homogenous for the cancer state.

In some embodiments, each corresponding trained neural network in the plurality of trained neural networks comprises: a corresponding plurality of inputs, wherein each input in the corresponding plurality of inputs is for a methylation state in the respective genomic region represented by the corresponding neural network, a corresponding first hidden layer comprising a corresponding plurality of hidden neurons, wherein each hidden neuron in the corresponding plurality of hidden neurons (i) is fully connected to each input in the plurality of inputs, (ii) is associated with a first activation function type, and (iii) is associated with a corresponding weight in the corresponding plurality of weights for the corresponding trained neural network, and one or more corresponding neural network outputs, wherein each respective neural network output in the corresponding one or more neural network outputs (i) directly or indirectly receives, as input, an output of each hidden neuron in the corresponding plurality of hidden neurons, and (ii) is associated with a second activation function type.

In some embodiments, each corresponding trained neural network in the plurality of trained neural networks is a fully connected neural network.

In some embodiments, the first activation function type is tanh, sigmoid, softmax, Gaussian, Boltzmann-weighted averaging, absolute value, linear, rectified linear unit (ReLU), bounded rectified linear, soft rectified linear, parameterized rectified linear, average, max, min, sign, square, square root, multiquadric, inverse quadratic, inverse multiquadric, polyharmonic spline, or thin-plate spline.

In some embodiments, the second activation function type is Softmax.

In some embodiments, the corresponding plurality of hidden neurons consists of between two neurons and forty-eight neurons.

In some embodiments, the corresponding plurality of hidden neurons consists of between four neurons and twenty-four neurons.

In some embodiments, a first corresponding trained neural network has a different number of neurons in the corresponding first hidden layer than a second corresponding trained neural network in the plurality of trained neural networks.

In some embodiments, a number of hidden layers in each corresponding trained neural network in the plurality of trained neural networks is limited to the corresponding first hidden layer.

In some embodiments, a number of hidden layers in each corresponding trained neural network in the plurality of trained neural networks consists of between two and five hidden layers.

In some embodiments, the one or more corresponding neural network outputs of a corresponding trained neural network in the plurality of trained neural networks is a single neural network output that provides a probability that the training subject has the cancer state.

In some embodiments, the one or more corresponding neural network outputs of a corresponding trained neural network in the plurality of trained neural networks is a plurality of neural network outputs, wherein each neural network output in the plurality of neural network outputs provides a probability that the training subject has a corresponding cancer type in a plurality of cancer types.

In some embodiments, the plurality of cancer types comprises any combination of adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, and leukemia.

In some embodiments, each genomic region in the plurality of genomic regions is represented by a single corresponding neural network in the plurality of trained neural networks.

In some embodiments, each genomic region in the plurality of genomic regions is represented by between two and five corresponding trained neural networks in the plurality of trained neural networks, and a value of a first corresponding weight in the corresponding first hidden layer is different in each of the between two and five corresponding trained neural networks.

In some embodiments, each genomic region in the plurality of genomic regions is represented by between two and five corresponding neural networks in the plurality of trained neural networks, and a value of each corresponding weight in the first hidden layer is independent in each of the between two and five corresponding trained neural networks.

In some embodiments, the B) training uses a regularization on the corresponding weight of each hidden neuron in the corresponding plurality of hidden neurons.

In some embodiments, the regularization includes an L1 or L2 penalty.

In some embodiments, each corresponding plurality of nucleic acid methylation fragments comprises more than 100 nucleic acid methylation fragments.

In some embodiments, an average number of nucleic acid methylation fragments across each corresponding plurality of nucleic acid methylation fragments comprises 1000 or more nucleic acid methylation fragments, 5000 or more nucleic acid methylation fragments, 10,000 or more nucleic acid methylation fragments, 20,000 or more nucleic acid methylation fragments, or 30,000 or more nucleic acid methylation fragments.

In some embodiments, an average number of nucleic acid methylation fragments across each corresponding plurality of nucleic acid methylation fragments is between 10,000 nucleic acid methylation fragments and 50,000 nucleic acid methylation fragments.

In some embodiments, a multigenomic region consists of a subset of the plurality of genomic regions, and the C) performing makes use of a multi-genomic region neural network that accepts, as input, an output of each trained neural network corresponding to a genomic region in the subset of the plurality of genomic regions in order to obtain a respective feature of each genomic region in the subset of the plurality of genomic regions for the respective training subject or a single feature for the subset of the plurality of genomic regions.

In some embodiments, the C) performing uses only those respective nucleic acid methylation fragments for feature identification that, when evaluated by the corresponding trained neural network, have a collective specificity across the plurality of training subjects that exceeds a specificity threshold value.

In some embodiments, the specificity threshold value is a value between 0.9500 and 0.99999.

In some embodiments, the specificity threshold value is 0.999, 0.9999, or 0.99999.

In some embodiments, the methylation sequencing of nucleic acids in the biological sample obtained from the respective training subject is methylation sequencing of cell-free nucleic acids in the biological sample, and the method further comprises training a corresponding untrained neural network in the plurality of trained neural networks, at least in part, using methylation data for nucleic acid methylation fragments obtained from one or more tumor samples representative of the cancer state.

In some embodiments, the B) training uses K-fold cross-validation to adjust a learning rate of the corresponding plurality of weights for the corresponding trained neural network.

In some embodiments, the B) training uses a regularization on the corresponding weight of each hidden neuron in the corresponding plurality of hidden neurons and wherein the B) training uses K-fold cross-validation to adjust a penalty associated with the regularization.

In some embodiments, the corresponding untrained neural network includes a number of hidden layers and the B) training uses K-fold cross-validation to adjust the number of hidden layers in the corresponding untrained neural network.

In some embodiments, the B) training uses K-fold cross-validation to adjust the number of weights in the corresponding plurality of weights.

In some embodiments, the B) training uses K-fold cross-validation to adjust the number of untrained neural networks in the plurality of untrained neural networks.

In some embodiments, the B) training uses K-fold cross-validation to adjust the number of trained neural networks in the plurality of trained neural networks.

In some embodiments, the B) training uses K-fold cross-validation to adjust an initialization of the corresponding trained neural network.

According to another aspect of the present disclosure provides a computer system for obtaining a plurality of features for determining a cancer state of a subject, the computer system comprising: at least one processor; and a memory storing at least one program for execution by the at least one processor, the at least one program comprising instructions for: A) obtaining a plurality of genotypic datasets, each respective genotypic dataset in the plurality of genotypic datasets for a respective training subject in a plurality of training subjects, wherein the respective genotypic dataset comprises, in electronic form, (i) a corresponding label for the cancer state of the respective training subject and (ii) a corresponding plurality of nucleic acid methylation fragments, wherein each respective nucleic acid methylation fragment in the corresponding plurality of nucleic acid methylation fragments comprises a corresponding methylation pattern comprising a methylation state of each CpG site in a corresponding plurality of CpG sites of the respective nucleic acid methylation fragment, and wherein the corresponding plurality of nucleic acid methylation fragments is determined by a methylation sequencing of nucleic acids in a biological sample obtained from the respective training subject; B) training, for each respective genomic region in a plurality of genomic regions, an untrained corresponding untrained neural network in a plurality of untrained neural networks, thereby obtaining a corresponding trained neural network in a plurality of trained neural networks, wherein: the corresponding untrained neural network independently corresponds to the respective genomic region, the corresponding untrained neural network comprises a corresponding plurality of weights, the corresponding untrained neural network scores respective nucleic acid methylation fragments in each corresponding plurality of nucleic acid methylation fragments that map to the respective genomic region thereby obtaining a corresponding plurality of training scores, the training updates a corresponding value of each weight in the corresponding plurality of weights in the corresponding untrained neural network based on a comparison of the corresponding plurality of training scores to the corresponding label for the cancer state of the respective training subjects originating the respective nucleic acid methylation fragments thereby obtaining the corresponding trained neural network; and C) performing feature identification by, for each respective genomic region in the plurality of genomic regions, for each training subject in the plurality of training subjects: obtaining a respective feature of the genomic region for the respective training subject by using the trained neural network that corresponds to the respective genomic region to score respective nucleic acid methylation fragments in the plurality of nucleic acid methylation fragments corresponding to the respective training subject that map to the respective genomic region for the cancer state, thereby obtaining a plurality of features for each genomic region in the plurality of genomic regions.

Another aspect of the present disclosure provides a non-transitory computer-readable storage medium having stored thereon program code instructions that, when executed by a processor, cause the processor to perform a method of obtaining a plurality of features for determining a cancer state of a subject, the method comprising: at a computer system comprising at least one processor and a memory storing at least one program for execution by the at least one processor, the at least one program comprising instructions for: A) obtaining a plurality of genotypic datasets, each respective genotypic dataset in the plurality of genotypic datasets for a respective training subject in a plurality of training subjects, wherein the respective genotypic dataset comprises, in electronic form, (i) a corresponding label for the cancer state of the respective training subject and (ii) a corresponding plurality of nucleic acid methylation fragments, wherein each respective nucleic acid methylation fragment in the corresponding plurality of nucleic acid methylation fragments comprises a corresponding methylation pattern comprising a methylation state of each CpG site in a corresponding plurality of CpG sites of the respective nucleic acid methylation fragment, and wherein the corresponding plurality of nucleic acid methylation fragments is determined by a methylation sequencing of nucleic acids in a biological sample obtained from the respective training subject; B) training, for each respective genomic region in a plurality of genomic regions, an untrained corresponding untrained neural network in a plurality of untrained neural networks, thereby obtaining a corresponding trained neural network in a plurality of trained neural networks, wherein: the corresponding untrained neural network independently corresponds to the respective genomic region, the corresponding untrained neural network comprises a corresponding plurality of weights, the corresponding untrained neural network scores respective nucleic acid methylation fragments in each corresponding plurality of nucleic acid methylation fragments that map to the respective genomic region thereby obtaining a corresponding plurality of training scores, the training updates a corresponding value of each weight in the corresponding plurality of weights in the corresponding untrained neural network based on a comparison of the corresponding plurality of training scores to the corresponding label for the cancer state of the respective training subjects originating the respective nucleic acid methylation fragments thereby obtaining the corresponding trained neural network; and C) performing feature identification by, for each respective genomic region in the plurality of genomic regions, for each training subject in the plurality of training subjects: obtaining a respective feature of the genomic region for the respective training subject by using the trained neural network that corresponds to the respective genomic region to score respective nucleic acid methylation fragments in the plurality of nucleic acid methylation fragments corresponding to the respective training subject that map to the respective genomic region for the cancer state, thereby obtaining a plurality of features for each genomic region in the plurality of genomic regions.

Another aspect of the present disclosure provides a method for determining a cancer state of a subject, the method comprising: at a computer system comprising at least one processor and a memory storing at least one program for execution by the at least one processor, the at least one program comprising instructions for: A) obtaining, in electronic form, a plurality of nucleic acid methylation fragments, wherein each respective nucleic acid methylation fragment in the plurality of nucleic acid methylation fragments comprises a corresponding methylation pattern comprising a methylation state of each CpG site in a corresponding plurality of CpG sites of the respective nucleic acid methylation fragment, and wherein the plurality of nucleic acid methylation fragments is determined by a methylation sequencing of nucleic acids in a biological sample obtained from the subject; B) performing feature identification by, for each respective genomic region in a plurality of genomic regions, obtaining a respective feature of the genomic region for the subject by using a trained neural network in a plurality of trained neural networks that corresponds to the respective genomic region to score respective nucleic acid methylation fragments in the plurality of nucleic acid methylation fragments that map to the respective genomic region for the cancer state, thereby obtaining a plurality of features, wherein each respective feature in the plurality of features is for a corresponding genomic region in the plurality of genomic regions; and C) responsive to inputting the plurality of features to a downstream supervised model, obtaining a determination as to whether the test subject has the cancer state as output of the downstream supervised model.

Another aspect of the present disclosure provides a computer system for determining a cancer state of a subject, the computer system comprising: at least one processor; and a memory storing at least one program for execution by the at least one processor, the at least one program comprising instructions for: A) obtaining, in electronic form, a plurality of nucleic acid methylation fragments, wherein each respective nucleic acid methylation fragment in the plurality of nucleic acid methylation fragments comprises a corresponding methylation pattern comprising a methylation state of each CpG site in a corresponding plurality of CpG sites of the respective nucleic acid methylation fragment, and wherein the plurality of nucleic acid methylation fragments is determined by a methylation sequencing of nucleic acids in a biological sample obtained from the subject; B) performing feature identification by, for each respective genomic region in a plurality of genomic regions, obtaining a respective feature of the genomic region for the subject by using a trained neural network in a plurality of trained neural networks that corresponds to the respective genomic region to score respective nucleic acid methylation fragments in the plurality of nucleic acid methylation fragments that map to the respective genomic region for the cancer state, thereby obtaining a plurality of features, wherein each respective feature in the plurality of features is for a corresponding genomic region in the plurality of genomic regions; and C) responsive to inputting the plurality of features to a downstream supervised model, obtaining a determination as to whether the test subject has the cancer state as output of the downstream supervised model.

Another aspect of the present disclosure provides a non-transitory computer-readable storage medium having stored thereon program code instructions that, when executed by a processor, cause the processor to perform a method of determining a cancer state of a subject, the method comprising: at a computer system comprising at least one processor and a memory storing at least one program for execution by the at least one processor, the at least one program comprising instructions for: A) obtaining, in electronic form, a plurality of nucleic acid methylation fragments, wherein each respective nucleic acid methylation fragment in the plurality of nucleic acid methylation fragments comprises a corresponding methylation pattern comprising a methylation state of each CpG site in a corresponding plurality of CpG sites of the respective nucleic acid methylation fragment, and wherein the plurality of nucleic acid methylation fragments is determined by a methylation sequencing of nucleic acids in a biological sample obtained from the subject; B) performing feature identification by, for each respective genomic region in a plurality of genomic regions, obtaining a respective feature of the genomic region for the subject by using a trained neural network in a plurality of trained neural networks that corresponds to the respective genomic region to score respective nucleic acid methylation fragments in the plurality of nucleic acid methylation fragments that map to the respective genomic region for the cancer state, thereby obtaining a plurality of features, wherein each respective feature in the plurality of features is for a corresponding genomic region in the plurality of genomic regions; and C) responsive to inputting the plurality of features to a downstream supervised model, obtaining a determination as to whether the test subject has the cancer state as output of the downstream supervised model.

Another aspect of the present disclosure provides computer systems for performing any of the methods described in this present disclosure. For example, the computer system performs the method of obtaining a plurality of features for determining a cancer state of a subject and/or computer systems for determining a cancer state of a subject. Such computer systems can comprise at least one processor and a memory storing at least one program comprising instructions for execution by the at least one processor. In some embodiments, the at least one program comprises instructions for performing any of the methods and embodiments disclosed herein, and/or any combinations thereof. In some embodiments, the at least one program is configured for execution by a computer.

Another aspect of the present disclosure provides a non-transitory computer-readable storage medium having stored thereon program code instructions that, when executed by a processor, cause the processor to perform any of the methods described in this present disclosure. For example, the storage medium causes the processor to perform a method of obtaining a plurality of features for determining a cancer state of a subject and/or a method of determining a cancer state of a subject. In some embodiments, the program code instructions comprise instructions for performing any of the methods and embodiments disclosed herein, and/or any combinations thereof. In some embodiments, the program code instructions are configured for execution by a computer.

VII. Additional Considerations

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Any of the steps, operations, or processes described herein as being performed by the analytics system may be performed or implemented with one or more hardware or software modules of the apparatus, alone or in combination with other computing devices. In one embodiment, a software module is implemented with a computer program product comprising a computer-readable medium containing computer program code, which can be executed by a computer processor for performing any or all of the steps, operations, or processes described.

What is claimed is:

1. A method comprising:

performing, by a sequencing device, a sequencing assay with a targeted panel targeting a plurality of genomic regions, wherein the targeted panel includes, for each genomic region, one or more hybridization probes for capturing cfDNA fragments originating from the genomic region, wherein the sequencing assays yields sequencing data for a biological sample comprising a plurality of sequence reads representing cfDNA fragments, each sequence read overlapping at least one genomic region of a plurality of genomic regions;

for each cfDNA fragment of the biological sample, determining, by a computer processor, a first score for the genomic region that the cfDNA fragment overlaps, the first score for a genomic region determined by inputting the sequence read for the cfDNA fragment into a shallow neural network trained for the genomic region, the shallow neural network configured to generate the first score representative of a likelihood that the cfDNA fragment is derived from a cancer biological sample, each shallow neural network of a plurality of shallow neural networks spanning the plurality of genomic regions comprises no more than three hidden layers and is trained by:

accessing a first plurality of sequence reads obtained from cancer samples and a second plurality of sequence reads obtained from non-cancer samples, wherein the first plurality of sequence reads and the second plurality of sequence reads overlap the genomic region, and training the shallow neural network with the first plurality of sequence reads and the second plurality of sequence reads;

generating, by the computer processor, a feature vector for the biological sample, each feature of the feature vector corresponding to a genomic region of the plurality of genomic regions and generated according to a count of cfDNA fragments having a score for the genomic region above a threshold score; and inputting, by the computer processor, the feature vector into a trained machine-learning model to generate a cancer prediction for the biological sample, the trained model trained by:

accessing sequencing data for a plurality of cancer samples and a plurality of non-cancer samples, generating a feature vector for each cancer sample and for each non-cancer sample by applying the shallow neural networks to the sequencing data of each sample, and training the trained model with the feature vectors for the cancer samples and the non-cancer samples.

2. The method of claim 1, wherein each shallow neural network consists of one hidden layer.

3. The method of claim 2, wherein the hidden layer in each shallow neural network comprises no more than one of: 8 nodes, 9 nodes, 10 nodes, 11 nodes, 12 nodes, 16 nodes, 20 nodes, 24 nodes, 28 nodes, and 32 nodes.

4. The method of claim 1, wherein each shallow neural network consists of two hidden layers.

5. The method of claim 1, wherein a first genomic region comprises a first number of CpG sites and a second genomic region in the plurality of genomic regions comprises a second number of CpG sites that is different than the first number of CpG sites.

6. The method of claim 1, wherein each shallow neural network outputs the first score that corresponds to a likelihood that a cfDNA fragment is derived from a biological sample of a first cancer type and a second score that corresponds to a likelihood that the cfDNA fragment is derived from a biological sample of a second cancer type different than the first cancer type.

7. The method of claim 1, wherein each feature of the feature vector is generated according to a normalization of the count of cfDNA fragments having a score for the genomic region above the threshold score.

8. The method of claim 1, wherein each cfDNA fragment is an anomalous fragment, the method further comprising:

filtering an initial set of cfDNA fragments with p-value filtering to generate the set of anomalous fragments, the filtering comprising removing fragments from the initial set having below a threshold p-value with respect to other fragments to produce the set of anomalous fragments.

9. The method of claim 1, wherein the trained machine-learning model is a neural network algorithm, a support vector machine algorithm, a Naive Bayes algorithm, a nearest neighbor algorithm, a boosted trees algorithm, a random forest algorithm, a decision tree algorithm, a multinomial logistic regression algorithm, a linear model, or a linear regression algorithm.

10. A method for training a machine-learning cancer prediction model, comprising:

performing, by a sequencing device on a plurality of cancer samples and a plurality of non-cancer samples, a sequencing assay with a targeted panel targeting a plurality of genomic regions, wherein the targeted panel includes, for each genomic region, one or more hybridization probes for capturing cfDNA fragments originating from the genomic region, wherein the sequencing assays yields sequencing data for each sample comprising a plurality of sequence reads representing the cfDNA fragments, with each sequence read overlapping at least one genomic region of a plurality of genomic regions;

for each sequence read in each sample, determining, by a computer processor, a first score for the genomic region that the sequence read overlaps, the first score for a genomic region determined by inputting the sequence read into a shallow neural network trained for the genomic region, the shallow neural network configured to generate the first score representative of a likelihood that the sequence read is derived from a cancer biological sample, each shallow neural network of a plurality of shallow neural networks spanning the plurality of genomic regions comprises no more than three hidden layers and is trained by:

accessing a first plurality of sequence reads obtained from cancer samples and a second plurality of sequence reads obtained from non-cancer samples, wherein the first plurality of sequence reads and the second plurality of sequence reads overlap the genomic region, and training the shallow neural network with the first plurality of sequence reads and the second plurality of sequence reads;

generating, by the computer processor, a feature vector for each sample, each feature of the feature vector corresponding to a genomic region of the plurality of genomic regions and generated according to a count of sequence reads having a score for the genomic region above a threshold score; and training, by the computer processor, the machine-learning cancer prediction model with the feature vectors for the cancer samples and the non-cancer samples, wherein the trained cancer prediction model is configured to generate a cancer prediction for a biological sample.

11. The method of claim 10, wherein each shallow neural network consists of one hidden layer.

12. The method of claim 11, wherein each hidden layer in each shallow neural network comprises no more than one of: 8 nodes, 9 nodes, 10 nodes, 11 nodes, 12 nodes, 16 nodes, 20 nodes, 24 nodes, 28 nodes, and 32 nodes.

13. The method of claim 10, wherein a first genomic region comprises a first number of CpG sites and a second genomic region in the plurality of genomic regions comprises a second number of CpG sites that is different than the first number of CpG sites.

14. The method of claim 10, wherein each shallow neural network outputs the first score that corresponds to a likelihood that the sequence read is derived from a biological sample of a first cancer type and a second score that corresponds to a likelihood that the sequence read is derived from a biological sample of a second cancer type different than the first cancer type.

15. The method of claim 10, wherein each feature of the feature vector is generated according to a normalization of the count of sequence reads having a score for the genomic region above the threshold score.

* * * * *